(12) United States Patent
Nantz et al.

(10) Patent No.: US 10,342,870 B2
(45) Date of Patent: Jul. 9, 2019

(54) NANOPARTICLES FOR DRUG DELIVERY

(71) Applicant: UNIVERSITY OF LOUISVILLE RESEARCH FOUNDATION, INC., Louisville, KY (US)

(72) Inventors: Michael H. Nantz, Louisville, KY (US); Ralph Knipp, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 98 days.

(21) Appl. No.: 15/502,131

(22) PCT Filed: Aug. 6, 2015

(86) PCT No.: PCT/US2015/044080
§ 371 (c)(1),
(2) Date: Feb. 6, 2017

(87) PCT Pub. No.: WO2016/022845
PCT Pub. Date: Feb. 11, 2016

(65) Prior Publication Data
US 2017/0224839 A1    Aug. 10, 2017

Related U.S. Application Data

(60) Provisional application No. 62/034,059, filed on Aug. 6, 2014.

(51) Int. Cl.
*A61K 41/00*    (2006.01)
*A61K 47/69*    (2017.01)

(52) U.S. Cl.
CPC .......... *A61K 41/0028* (2013.01); *A61K 41/00* (2013.01); *A61K 47/6923* (2017.08); *A61K 47/6929* (2017.08)

(58) Field of Classification Search
CPC ............................... A61K 47/54; A61K 47/55
See application file for complete search history.

(56) References Cited

U.S. PATENT DOCUMENTS

| | | |
|---|---|---|
| 9,849,193 B2 | 12/2017 | Nantz et al. |
| 2011/0130616 A1 | 6/2011 | Seeney et al. |
| 2012/0302516 A1 | 11/2012 | Nantz et al. |
| 2013/0302408 A1 | 11/2013 | Weaver |
| 2015/0374849 A1* | 12/2015 | Knipp ................ A61K 41/0028 424/490 |

FOREIGN PATENT DOCUMENTS

| WO | 2011049972 A1 | 4/2011 |
|---|---|---|
| WO | 2014124329 A1 | 8/2014 |

OTHER PUBLICATIONS

Aryal, et al., "Doxorubicin conjugated gold nanoparticles as water-soluble and pH-responsive anticancer drug nanocarriers", J Mater Chem 19, 7879-7884 (2009).
Bulte, et al., "Iron oxide MR contrast agents for molecular and cellular imaging", NMR Biomed 17(7), 484-499 (2004).
Carrey, et al., "Simple models for dynamic hysteresis loop calculations of magnetic single-domain nanoparticles: Application to magnetic hyperthermia optimization", J Appl Phys 109, 083921 (2011).
Choi, et al., "A photochemical approach for controlled drug release in targeted drug delivery", Bioorg Med Chem 20(3), 1281-1290 (2012).
Kievit, et al., "Surface engineering of iron oxide nanoparticles for targeted cancer therapy", Acc Chem Res 44 (10), 853-862 (2011).
Kim, et al., "Designed Fabrication of a Multifunctional Polymer Nanomedical Platform for Simultaneous Cancer-Targeted Imaging and Magnetically Guided Drug Delivery", Advanced Materials vol. 20 (3), 478-483 (2008).
Lee, et al., "Uniform mesoporous dye-doped silica nanoparticles decorated with multiple magnetite nanocrystals for simultaneous enhanced magnetic resonance imaging, fluorescence imaging, and drug delivery", J Am Chem Soc 132(2), 552-557 (2010).
Liu, et al., "Instantaneous drug delivery of magnetic/thermally sensitive nanospheres by a high-frequency magnetic field", Langmuir 24 (23), 13306-13311 (2008).
Liu, et al., "Magnetically Sensitive Alginate-Templated Polyelectrolyte Multilayer Microcapsules for Controlled Release of Doxorubicin", Journal of Physical Chemistry C vol. 114 (17), 7673-7679 (2010).
Meng, et al., "Engineered design of mesoporous silica nanoparticles to deliver doxorubicin and P-glycoprotein siRNA to overcome drug resistance in a cancer cell line", ACS Nano 4 (8), 4539-4550 (2010).
Meng, et al., "Iron oxide-based nanomagnets in nanomedicine: fabrication and applications", Nano Reviews 1, 4883, 17 pages (2010).
Meyers, et al., "Experimental approach in the use and magnetic control of metallic iron particles in the lymphatic and vascular system of dogs as a contrast and isotopic agent", Am J Roentgenol Radium Ther Nucl Med 90, 1068-1077 (1963).
Patent Cooperation Treaty, International Searching Authority, Search Report and Written Opinion for PCT/US2015/044080, 9 pages, dated Nov. 3, 2015.
Rahimi, et al., "In vitro evaluation of novel polymer-coated magnetic nanoparticles for controlled drug delivery", Nanomedicine 6 (5), 672-680 (2010).
Yang, et al., "Fe3O4 nanostructures: synthesis, growth mechanism, properties and applications", Chem Commun (Camb.) 47(18), 5130-5141 (2011).
Yu, et al. "Drug-loaded superparamagnetic iron oxide nanoparticles for combined cancer imaging and therapy in vivo", Angew Chem Int Ed Engl 47 (29), 5362-5365 (2008).
Zhang, et al., "Uptake of folate-conjugated albumin nanoparticles to the SKOV3 cells", Int J Pharm 287 (1-2), 155-162 (2004).

* cited by examiner

*Primary Examiner* — Kyle A Purdy
(74) *Attorney, Agent, or Firm* — Viksnins Harris Padys Malen LLP

(57) ABSTRACT

The invention provides therapeutic magnetic nanoparticles containing a therapeutic agent connected to a magnetic nanoparticle core through a stable functional group and a linker that can be induced to release the therapeutic agent from the core, through hydrolysis of the functional group. Also provided are methods for making nanoparticles, and methods for using nanoparticles.

19 Claims, 24 Drawing Sheets

NANOPARTICLES FOR DRUG DELIVERY

RELATED APPLICATION

This application claims priority to U.S. Provisional Patent Application No. 62/034,059 filed Aug. 6, 2014, the entirety of which is incorporated herein by reference.

BACKGROUND

An important attribute of a drug delivery system is its ability to allow for spatial and temporal regulated drug release, thereby minimizing side effects and improving therapeutic efficacy of conventional pharmaceuticals. Iron oxide nanoparticles (NPs), specifically $Fe_3O_4$ nanoparticles, possess many appropriate qualities that make them a viable choice for drug delivery. $Fe_3O_4$ NPs are biocompatible (Kievit, F. M., et al., *Accounts of Chemical Research* 2011, 44 (10), 853-862), have low cytotoxicity (Bulte, J. W. M., et al., *NMR in Biomedicine* 2004, 17, 484-499), and provide multiple means for surface modification. Though these attributes are needed in a drug delivery vehicle, there are multiple different NPs that possess similar qualities including gold and silica. $Fe_3O_4$ is set apart from these NPs due to its paramagnetic or superparamagnetic (SPM) qualities (Yang, C., et al., *Chemical Communications* 2011, 47, 5130-5141). The SPM properties of $Fe_3O_4$ NPs have been used for a variety of applications. A basic utilization of SPM capability is to induce non-invasive hyperthermia within cancer cells. Alternating electromagnetic field (AMF)-induced $Fe_3O_4$ NPs heat body tissue to temperatures as high as 45° C., and this causes cell death. In addition, when functionalized either by ionic interactions or through entrapment via a polymer gel coating, drugs can be guided to tumor regions through the use of a magnet, as first demonstrated by Meyers in 1963 (Meyers, P. H., et al., *American Journal of Roentgenology, Radium Therapy, and Nuclear Medicine* 1963, 90, 1068-1077). Through more advanced methods, $Fe_3O_4$ NPs are now extensively functionalized with complex delivery mechanisms and can be directed by taking advantage of tumor folate receptors (Kim, J., et al., *Advanced Materials* 2008, 20, 478-483, Zhang, Z., et al., *Biomaterials* 2007, 28 (10), 1889-1899, Zhang, L., et al., *International Journal of Pharmaceutics* 2004, 287 (1-2), 155-162). Finally, iron oxide also can be used as a magnetic resonance imaging contrast agent, so delivery systems based on this material can be visualized (Lee, J. E.; et al., *Journal of the American Chemical Society* 2010, 132, 552-557).

Some of the most common methods of functionalization or attachment of drug payloads to $Fe_3O_4$ NPs involve the use of ionic attraction (Nantz, M. H., et al., *PCT Int. Appl.* 2011, WO 2011049972 A1 20110428), the addition of a mesoporous silica shell around the $Fe_3O_4$ NPs followed by further functionalization of the silica (Meng, H., et al., A. E., *ACS Nano* 2010, 4 (8), 4539-4550, Lin, Meng M., et al., *Nano Reviews* 2010, 1, 4883) or the use of a polymer coating around the $Fe_3O_4$ NPs (Yu, M. K., et al., *Angewandte Chemie International Edition* 2008, 47 (29), 5362-5365, Rahimi, M., et al., *Nanomedicine: Nanotechnology, Biology, and Medicine* 2010, 6, 672-680). Once the NPs reach target (e.g., cancerous) tissue, a release mechanism is initiated so that the drug payloads are available only to the target tissue. One of the most common release methods involves use of a pH sensitive trigger, such as when using a hydrazone linkage (Aryal, S., et al., *Journal of Materials Chemistry* 2009, 19, 7879-7884). For example, when the loaded NP enters into a tumor, the reduced pH of the tumor can hydrolyze the hydrazone linkage to unmask the drug (a carbonyl-based drug). Another method of release is photochemical. By adding a photolabile group into a linker, usually an aromatic ring with a nitro-group ortho to a leaving group, the drug can be released upon exposure to a specific wavelength of light (Choi, S. K., et al., *Bioorganic & Medicinal Chemistry* 2012, 20, 1281-1290).

Another method to release the drug involves the use of an alternating electromagnetic field (AMF). An AMF, similar to an AC current, switches the poles of the magnetic current at a quick pace, and this causes resident iron oxide NPs to heat as they struggle to stay aligned with the applied magnetic field (Carrey, J., et al., *Journal of Applied Physics* 2011, 109, 083921). AMF-mediated drug delivery has a distinct advantage over the pH sensitive linker approach in that drug release relies on a controllable external stimulus whereas the acid labile linker requires a stimulus within the patient that cannot be easily controlled. If the tumor is not sufficiently acidic, then the linker-bound drug will not be released. In the same way, if certain healthy cells happen to be overly acidic, then the drug is released and can exert its pharmacological effect on healthy cells. In contrast, AMF exposure allows for the controlled release in a specific region and at a specific time without the need for precise, and often unpredictable, internal conditions. Thus AMF-mediated delivery systems offer the advantages of spatial and temporal control.

Despite the advantages in controlled release using an AMF trigger, many present NP drug delivery systems have a problem of premature drug release (i.e., leakage). In these instances, drugs are slowly released prior to application of the external stimulus. This is largely due to the inability of the drugs in these delivery systems to be covalently retained until the stimulus is applied. For example, AMF-induced NP heating commonly is used to reduce ionic interactions and/or hydrogen bonding interactions (Biswas, S. Functionalized Nanoparticles for AMF-Induced Gene and Drug Delivery. University of Louisville, Louisville, Ky., 2011), or to cause a polymer shell to squeeze out the drug payload (Liu, T.-Y., et al., *Langmuir* 2008, 24, 13306-13311) or to expand and allow the drug payload to diffuse away (Liu, J., et al., *Journal of Physical Chemistry C* 2010, 114, 7673-7679). In these cases, the ambient heat or biological milieu of a living system can reduce the ionic/hydrogen bonding interactions between NP and drug, or cause polymer contractions or expansions. Premature drug release occurs since the drug is not covalently attached to the NP carrier.

Patent application publication WO2014/124329 describes therapeutic magnetic nanoparticles which include a therapeutic agent connected to a magnetic nanoparticle through a linker and functional group. These nanoparticles include a linker that will undergo an intramolecular cyclization with the functional group thereby releasing the therapeutic agent from the magnetic nanoparticle core.

There is a need for alternative drug delivery systems with reduced premature release of its drug payload and that can optionally target the drug spatially, temporally, or both spatially and temporally.

SUMMARY OF INVENTION AND CERTAIN EMBODIMENTS

It has been discovered that therapeutic magnetic nanoparticles that connect a therapeutic agent to a magnetic nanoparticle core through a stable functional group and a linker can be induced to release the therapeutic agent from the core (e.g., through hydrolysis of the functional group).

The release of the therapeutic agent can occur without the linker and functional group undergoing intramolecular cyclization.

It has also been discovered that therapeutic magnetic nanoparticles that connect a therapeutic agent to a magnetic nanoparticle core through a linker and functional group which include a linker comprising a protected amine moiety at a specified distance from the functional group can undergo deprotection of the protected amine followed by intramolecular cyclization with the functional group to release the therapeutic agent.

Accordingly, one embodiment provides a therapeutic magnetic nanoparticle, or a salt thereof, comprising a magnetic nanoparticle covalently bonded to one or more -L-D groups wherein D is a residue of a therapeutic agent (e.g., a residue of a therapeutic agent, a residue of a prodrug of a therapeutic agent or a residue of a functional group derivative of a therapeutic agent) and L is a linker, wherein:

L is -$L^1$-$L^2$-;

each $L^1$ is covalently bonded to the magnetic nanoparticle and is independently a branched or unbranched chain or cyclic group or a combination of chain and cyclic groups that comprises 1-200 atoms; and each $L^2$ is independently a group capable of releasing a therapeutic agent; and wherein L is not capable of undergoing intramolecular cyclization to release the therapeutic agent.

One embodiment provides a therapeutic magnetic nanoparticle, or a salt thereof, comprising a magnetic nanoparticle covalently bonded to one or more -L-D groups wherein;

D is a residue of a therapeutic agent (e.g., a residue of a therapeutic agent, a residue of a prodrug of a therapeutic agent or a residue of a functional group derivative of a therapeutic agent);

L is a linker -$L^1$-$L^2$-;

each $L^1$ is covalently bonded to the magnetic nanoparticle and is independently a branched or unbranched chain or cyclic group or a combination of chain and cyclic groups that comprises 1-250 atoms; and each $L^2$ is independently a group capable of releasing a therapeutic agent; and wherein L is not capable of undergoing intramolecular cyclization to release the therapeutic agent.

One embodiment provides a therapeutic magnetic nanoparticle, or a salt thereof, comprising a magnetic nanoparticle covalently bonded to one or more -L-D groups wherein D is a residue of a therapeutic agent (e.g., a residue of a therapeutic agent, a residue of a prodrug of a therapeutic agent or a residue of a functional group derivative of a therapeutic agent) and L is a linker, wherein:

L is -$L^1$-$L^2$-;

each $L^1$ is covalently bonded to the magnetic nanoparticle (e.g., the magnetic nanoparticle and/or the coating of a coated magnetic nanoparticle) and is independently a branched or unbranched chain or cyclic group or a combination of chain and cyclic groups that comprises 1-50 atoms; and each $L^2$ is independently a group capable of releasing a therapeutic agent.

In certain embodiments $L^2$ can be hydrolyzed to release the therapeutic agent.

In certain embodiments $L^2$ can release the therapeutic agent by application of an alternating electromagnetic field to the magnetic nanoparticle.

In certain embodiments $L^2$ is:

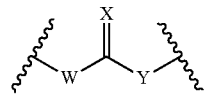

W is absent, —O—, —S— or —$NR^b$—;
X is O, S or $NR^c$;
Y is absent, —O—, —S— or —$NR^d$—;
$R^b$ is H, $(C_1-C_6)$alkyl, $(C_2-C_6)$alkenyl or $(C_2-C_6)$alkynyl;
$R^c$ is H, $(C_1-C_6)$alkyl, $(C_2-C_6)$alkenyl or $(C_2-C_6)$alkynyl;
$R^d$ is H, $(C_1-C_6)$alkyl, $(C_2-C_6)$alkenyl or $(C_2-C_6)$alkynyl; and wherein D together with Y of $L^2$ or D together with W—C(=X)—Y of $L^2$ is the moiety:

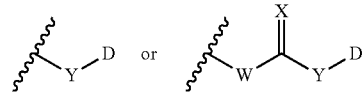

wherein the moiety is a residue of a therapeutic agent.

In certain embodiments the atoms of $L^1$ are selected from carbon, oxygen, nitrogen, sulfur and silicon.

In certain embodiments $L^1$ does not include an —NH—, —$NH_2$ or —NHR group wherein R is $(C_1-C_6)$alkyl.

In certain embodiments $L^1$ does not include a hydrazone group.

In certain embodiments $L^1$ does not include an oxime ether group.

In certain embodiments $L^1$ comprises 2-20 atoms.
In certain embodiments $L^1$ comprises 2-10 atoms.
In certain embodiments $L^1$ comprises 4-50 atoms.
In certain embodiments $L^1$ comprises 4-40 atoms.
In certain embodiments $L^1$ comprises 4-30 atoms.
In certain embodiments $L^1$ comprises 4-20 atoms.
In certain embodiments $L^1$ comprises 4-15 atoms.
In certain embodiments $L^1$ comprises 7-20 atoms.
In certain embodiments $L^1$ comprises 7-15 atoms.
In certain embodiments $L^1$ comprises 6-15 atoms.
In certain embodiments $L^1$ comprises 12-150 atoms.
In certain embodiments $L^1$ comprises 12-120 atoms.
In certain embodiments $L^1$ comprises 12-90 atoms.
In certain embodiments $L^1$ comprises 12-60 atoms.
In certain embodiments $L^1$ comprises 12-45 atoms.
In certain embodiments $L^1$ comprises 21-150 atoms.
In certain embodiments $L^1$ comprises 21-90 atoms.
In certain embodiments $L^1$ includes 1-200 atoms.
In certain embodiments $L^1$ includes 1-100 atoms.
In certain embodiments $L^1$ includes 21-60 atoms.
In certain embodiments $L^1$ includes 2-20 atoms.
In certain embodiments $L^1$ includes 2-10 atoms.
In certain embodiments $L^1$ includes 4-50 atoms.
In certain embodiments $L^1$ includes 4-40 atoms.
In certain embodiments $L^1$ includes 4-30 atoms.
In certain embodiments $L^1$ includes 4-20 atoms.
In certain embodiments $L^1$ includes 4-15 atoms.
In certain embodiments $L^1$ includes 7-20 atoms.
In certain embodiments $L^1$ includes 7-15 atoms.
In certain embodiments $L^1$ includes 6-15 atoms.
In certain embodiments $L^1$ includes 12-150 atoms.
In certain embodiments $L^1$ includes 12-120 atoms.
In certain embodiments $L^1$ includes 12-90 atoms.
In certain embodiments $L^1$ includes 12-60 atoms.
In certain embodiments $L^1$ includes 12-45 atoms.

In certain embodiments L¹ includes 21-150 atoms.
In certain embodiments L¹ includes 21-90 atoms.
In certain embodiments L¹ includes 21-60 atoms.
In certain embodiments L¹ comprises a branched or unbranched chain.

In certain embodiments L¹ comprises a branched or unbranched chain comprising carbon atoms.

In certain embodiments L¹ is $(C_1-C_{15})$alkylene, $(C_1-C_{15})$heteroalkylene, $(C_2-C_{15})$alkenylene or $(C_2-C_{15})$alkynylene, wherein any $(C_1-C_{15})$alkylene, $(C_1-C_{15})$heteroalkylene, $(C_2-C_{15})$alkenylene or $(C_2-C_{15})$alkynylene of L¹ is optionally substituted with one or more halogen.

In certain embodiments L¹ is $(C_1-C_{15})$alkylene, $(C_2-C_{15})$alkenylene or $(C_2-C_{15})$alkynylene, wherein any $(C_1-C_{15})$alkylene, $(C_2-C_{15})$alkenylene or $(C_2-C_{15})$alkynylene of L¹ is optionally substituted with one or more halogen.

In certain embodiments L¹ comprises $(C_1-C_{15})$alkylene, $(C_1-C_{15})$heteroalkylene, $(C_2-C_{15})$alkenylene or $(C_2-C_{15})$alkynylene, wherein any $(C_1-C_{15})$alkylene, $(C_1-C_{15})$heteroalkylene, $(C_2-C_{15})$alkenylene or $(C_2-C_{15})$alkynylene of L¹ is optionally substituted with one or more halogen.

In certain embodiments L¹ comprises $(C_1-C_{15})$alkylene, $(C_2-C_{15})$alkenylene or $(C_2-C_{15})$alkynylene, wherein any $(C_1-C_{15})$alkylene, $(C_2-C_{15})$alkenylene or $(C_2-C_{15})$alkynylene of L¹ is optionally substituted with one or more halogen.

In certain embodiments L¹ is covalently bonded to the magnetic nanoparticle through a silicon or sulfur atom.

In certain embodiments the magnetic nanoparticle further comprises a coating.

In certain embodiments the coating comprises gold.
In certain embodiments the coating comprises silica.
In certain embodiments the magnetic nanoparticle comprises iron.
In certain embodiments the magnetic nanoparticle comprises iron oxide.
In certain embodiments the magnetic nanoparticle is an iron oxide nanoparticle coated with silica.
In certain embodiments a magnetic nanoparticle is an iron oxide nanoparticle or a coated iron oxide nanoparticle.
In certain embodiments the magnetic nanoparticle is an iron alloy.
In certain embodiments the magnetic nanoparticle is an iron oxide alloy.
In certain embodiments the magnetic nanoparticle is a coated iron oxide nanoparticle.
In certain embodiments the magnetic nanoparticle is an iron oxide nanoparticle.
In certain embodiments the coated iron oxide nanoparticle is an iron oxide nanoparticle coated with silica.
In certain embodiments the coated iron oxide nanoparticle is an iron oxide nanoparticle coated with gold.
In certain embodiments the magnetic nanoparticle is an iron oxide nanoparticle coated with silica.
In certain embodiments the magnetic nanoparticle is an iron oxide nanoparticle coated with gold.

Certain embodiments provide a therapeutic magnetic nanoparticle, or a salt thereof comprising a magnetic nanoparticle covalently bonded to one or more -L-D groups wherein each -L-D independently has the following formula I:

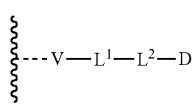

wherein:
V is $-OSi(G)_2-$, and the dashed line represents a covalent bond between the oxygen atom of $-OSi(G)_2-$ and the magnetic nanoparticle; or V is $-S-$, and the dashed line represents a covalent bond between $-S-$ and the magnetic nanoparticle;

L¹ is $(C_1-C_{15})$alkylene, $(C_1-C_{15})$heteroalkylene, $(C_2-C_{15})$alkenylene or $(C_2-C_{15})$alkynylene, wherein any $(C_1-C_{15})$alkylene, $(C_1-C_{15})$heteroalkylene, $(C_2-C_{15})$alkenylene or $(C_2-C_{15})$alkynylene of L¹ is optionally substituted with one or more halogen;

L² is:

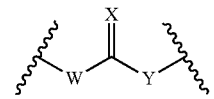

W is absent, $-O-$, $-S-$ or $-NR^b-$;
X is O, S or $NR^c$;
Y is absent, $-O-$, $-S-$ or $-NR^d-$;
each G is independently $-OR^{a1}$, $-OR^{a2}$ or $(C_1-C_6)$alkyl;
$R^{a1}$ is a covalent bond between the oxygen atom of $-OR^{a1}$ and the magnetic nanoparticle;
each $R^{a2}$ is independently H or $(C_1-C_6)$alkyl; or two $-OR^{a2}$ groups of two adjacent L-D groups together form $-O-$;
$R^b$ is H, $(C_1-C_6)$alkyl, $(C_2-C_6)$alkenyl or $(C_2-C_6)$alkynyl;
$R^c$ is H, $(C_1-C_6)$alkyl, $(C_2-C_6)$alkenyl or $(C_2-C_6)$alkynyl;
$R^d$ is H, $(C_1-C_6)$alkyl, $(C_2-C_6)$alkenyl or $(C_2-C_6)$alkynyl; and wherein D (a) together with Y of L² or (b) together with W—C(=Z)—Y of L² is the moiety:

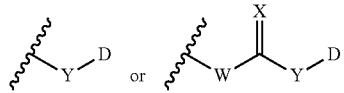

wherein the moiety is a residue of a therapeutic agent.

Certain embodiments provide a therapeutic magnetic nanoparticle, or a salt thereof comprising a magnetic nanoparticle covalently bonded to one or more -L-D groups wherein each -L-D independently has the following formula I:

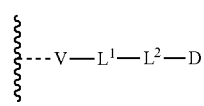

wherein:
V is $-OSi(G)_2-$, and the dashed line represents a covalent bond between the oxygen atom of $-OSi(G)_2-$ and the magnetic nanoparticle; or V is $-S-$, and the dashed line represents a covalent bond between $-S-$ and the magnetic nanoparticle;

L¹ is $(C_1-C_{15})$alkylene, $(C_1-C_{15})$heteroalkylene, $(C_2-C_{15})$alkenylene or $(C_2-C_{15})$alkynylene, wherein any $(C_1-C_{15})$alkylene, $(C_1-C_{15})$heteroalkylene, $(C_2-C_{15})$alkenylene or $(C_2-C_{15})$alkynylene of L¹ is optionally substituted with one or more halogen and wherein the $(C_1-C_{15})$heteroalkylene does not include nitrogen;

$L^2$ is:

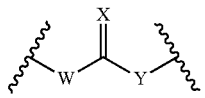

W is absent, —O—, —S— or —NR$^b$—;
X is O, S or NR';
Y is absent, —O—, —S— or —NR$^d$—;
each G is independently —OR$^{a1}$, —OR$^{a2}$ or (C$_1$-C$_6$)alkyl;
R$^{a1}$ is a covalent bond between the oxygen atom of —OR$^{a1}$ and the magnetic nanoparticle;
each R$^{a2}$ is independently H or (C$_1$-C$_6$)alkyl; or two —OR$^{a2}$ groups of two adjacent L-D groups together form —O—;
R$^b$ is H, (C$_1$-C$_6$)alkyl, (C$_2$-C$_6$)alkenyl or (C$_2$-C$_6$)alkynyl;
R$^c$ is H, (C$_1$-C$_6$)alkyl, (C$_2$-C$_6$)alkenyl or (C$_2$-C$_6$)alkynyl;
R$^d$ is H, (C$_1$-C$_6$)alkyl, (C$_2$-C$_6$)alkenyl or (C$_2$-C$_6$)alkynyl; and
wherein D (a) together with Y of $L^2$ or (b) together with W—C(=Z)—Y of $L^2$ is the moiety:

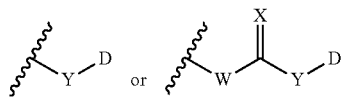

wherein the moiety is a residue of a therapeutic agent.

In certain embodiments V is —OSi(G)$_2$-, the magnetic nanoparticle is optionally coated with silica, and the dashed line represents a covalent bond between the oxygen atom of —OSi(G)$_2$- and the magnetic nanoparticle optionally coated with silica; or V is —S—, the magnetic nanoparticle is magnetic nanoparticle coated with gold, and the dashed line represents a covalent bond between —S— and the magnetic nanoparticle coated with gold.

In certain embodiments V is —OSi(G)$_2$-, the magnetic nanoparticle is coated with silica, and the dashed line represents a covalent bond between the oxygen atom of —OSi(G)$_2$- and the magnetic nanoparticle coated with silica.

In certain embodiments V is —OSi(G)$_2$-, the magnetic nanoparticle is an iron oxide nanoparticle coated with silica, and the dashed line represents a covalent bond between the oxygen atom of —OSi(G)$_2$- and the iron oxide nanoparticle coated with silica.

In certain embodiments -L-D has the following formula Ia:

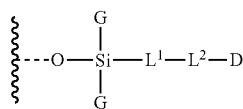

wherein the dashed bond represents a covalent bond to the magnetic nanoparticle.

In certain embodiments the therapeutic magnetic nanoparticle is further coated with silica and -L-D has the following formula Ia:

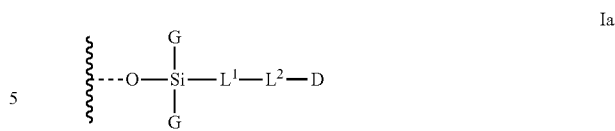

wherein the dashed bond represents a covalent bond to the magnetic nanoparticle further coated with silica.

In certain embodiments each G is —OR$^{a1}$.
In certain embodiments each G is —OR$^{a2}$, wherein each —OR$^{a2}$ together with another —OR$^{a2}$ group on an adjacent L-D group forms an —O—.
In certain embodiments each G is —OR$^{a1}$ or —OR$^{a2}$, wherein each —OR$^{a2}$ together with another —OR$^{a2}$ group on an adjacent L-D group form an —O—.

In certain embodiments V is —S—, the magnetic nanoparticle is coated in gold, and the dashed line represents a covalent bond between —S— and the magnetic nanoparticle coated in gold.

In certain embodiments V is —S—, the magnetic nanoparticle is coated in gold, and the dashed line represents a covalent bond between —S— and a gold atom of the magnetic nanoparticle coated in gold.

In certain embodiments -L-D has the following formula Ib:

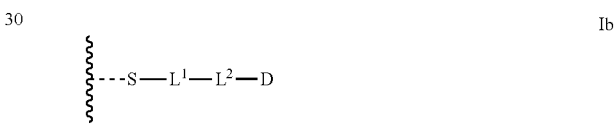

wherein the dashed bonds represent a covalent bond to the magnetic nanoparticle.

In certain embodiments $L^1$ is (C$_2$-C$_{12}$)alkylene optionally substituted with one or more halogen.
In certain embodiments $L^1$ is (C$_2$-C$_{12}$)alkylene.
In certain embodiments $L^1$ is (C$_2$-C$_8$)alkylene optionally substituted with one or more halogen.
In certain embodiments $L^1$ is (C$_2$-C$_6$)alkylene.
In certain embodiments $L^1$ is —(CH$_2$)$_6$—, —(CH$_2$)$_3$— or —(CH$_2$)$_4$—.
In certain embodiments $L^1$ is —(CH$_2$)$_3$— or —(CH$_2$)$_6$—.
In certain embodiments W is —O— or —NR$^b$—.
In certain embodiments X is O.
In certain embodiments Y is —O— or —NR$^d$—.
In certain embodiments $L^2$ is:

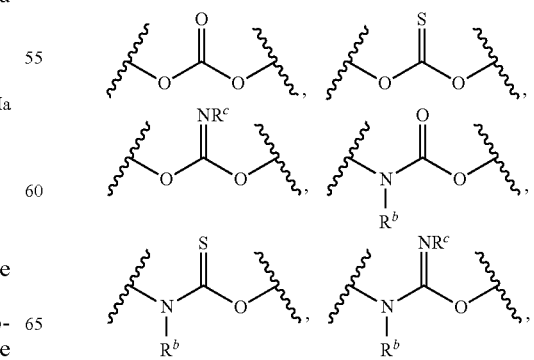

-continued

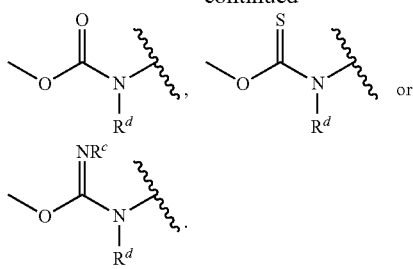

In certain embodiments L² is:

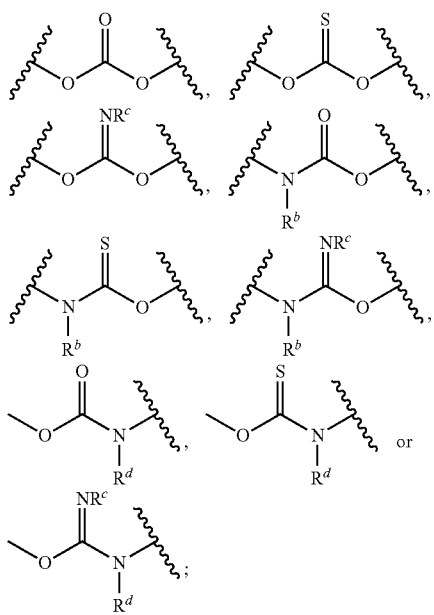

wherein D together with the —O— or —N(R$^d$)— of L² to which it is attached is the moiety:

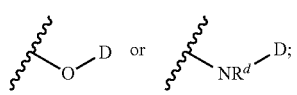

wherein the moiety is a residue of a therapeutic agent.
In certain embodiments R$^b$, R$^c$ and R$^d$ are each H.
In certain embodiments L² is:

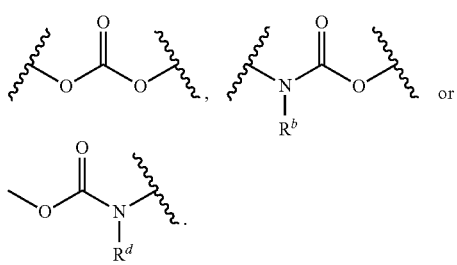

In certain embodiments L² is:

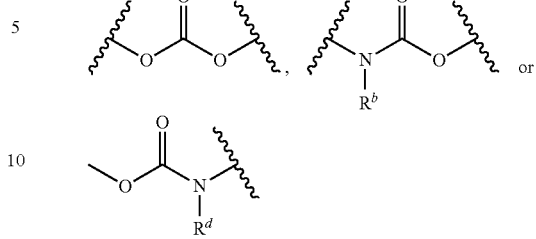

wherein D together with the —O— or —N(R$^d$)— of L² to which it is attached is the moiety:

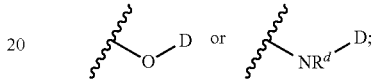

wherein the moiety is a residue of a therapeutic agent.
In certain embodiments -L¹-L²-D is selected from;

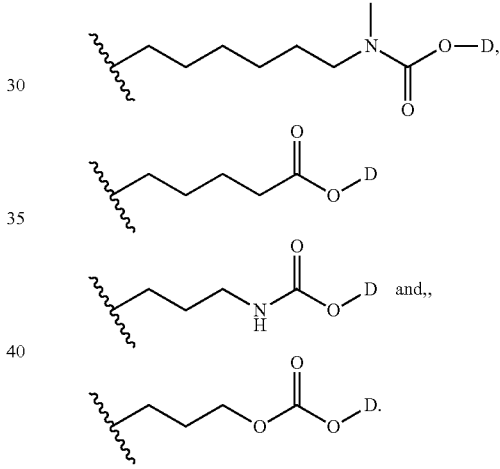

In certain embodiments -L¹-L²-D is selected from;

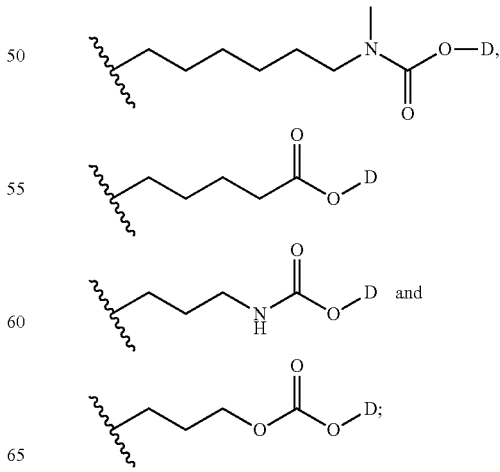

wherein D together with the —O— to which it is attached is the moiety:

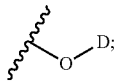

wherein the moiety is a residue of a therapeutic agent.

It is to be understood that two or more of the embodiments discussed herein above and below may be combined.

In certain embodiments the therapeutic nanoparticle further comprises a targeting element.

One embodiment provides a pharmaceutical composition comprising a therapeutic magnetic nanoparticle or a pharmaceutically acceptable salt thereof (e.g., a magnetic nanoparticle covalently bonded to one or more -L-D groups or a pharmaceutically acceptable salt thereof as described herein) and a pharmaceutically acceptable carrier.

One embodiment provides a method for administering a therapeutic agent to an animal (e.g., a mammal such as a human) comprising administering a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), to the animal.

One embodiment provides a method for treating cancer, a bacterial infection, a fungal infection, a parasitic infection or an antiviral infection in an animal (e.g., a mammal such as a human) in need thereof comprising administering an effective amount of a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), comprising providing conditions to release the therapeutic agent (D) from the therapeutic magnetic nanoparticle wherein the therapeutic agent is effective to treat cancer, a bacterial infection, a fungal infection, a parasitic infection or an antiviral infection.

One embodiment provides a method for treating cancer, a bacterial infection, a fungal infection, a parasitic infection or an antiviral infection in an animal (e.g., a mammal such as a human) comprising treating the animal with a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), to the animal wherein the therapeutic agent (D) is effective to treat cancer, a bacterial infection, a fungal infection, a parasitic infection or an antiviral infection.

One embodiment provides a method for treating cancer, a bacterial infection, a fungal infection, a parasitic infection or an antiviral infection in an animal (e.g., a mammal such as a human) in need thereof, comprising treating the animal with an effective amount of a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), to the animal.

Certain embodiments provide magnetically targeting the therapeutic magnetic nanoparticle to a specific location in the animal (e.g., a mammal such as a human).

Certain embodiments provide delivering a source of heat to the therapeutic magnetic nanoparticle to induce deprotection of a protected amine in the linker and cyclization of the linker thereby releasing the therapeutic agent from the therapeutic magnetic nanoparticle.

Certain embodiments provide applying an alternating electromagnetic field to the therapeutic magnetic nanoparticle to induce deprotection of a protected amine in the linker and cyclization of the linker thereby releasing the therapeutic agent from the therapeutic nanoparticle (e.g., a mammal).

Certain embodiments provide for further treating the animal (e.g., a mammal) with one or more additional therapeutic agents.

In certain embodiments the additional therapeutic agent is iron oxide nanoparticle.

One embodiment provides a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), for use in medical therapy.

One embodiment provides the use of a therapeutic magnetic or a pharmaceutically acceptable salt thereof (e.g., a magnetic nanoparticle covalently bonded to one or more -L-D groups, or a pharmaceutically acceptable salt thereof as described herein), to prepare a medicament for treating cancer, a bacterial infection, a fungal infection, a parasitic infection or an antiviral infection in an animal (e.g., a mammal such as a human).

One embodiment provides a therapeutic magnetic nanoparticle or a pharmaceutically acceptable salt thereof (e.g., a magnetic nanoparticle covalently bonded to one or more -L-D groups, or a pharmaceutically acceptable salt thereof as described herein), for the therapeutic or prophylactic treatment of cancer, a bacterial infection, a fungal infection, a parasitic infection or an antiviral infection.

As described in Example 1 and 2 a ketone or aldehyde of a therapeutic agent has been converted to a prodrug of the therapeutic agent as shown in formula IIIa which prodrug is attached to the linker. Accordingly, one embodiment provides a therapeutic agent which is a prodrug of the therapeutic agent and is represented by formula IIIa:

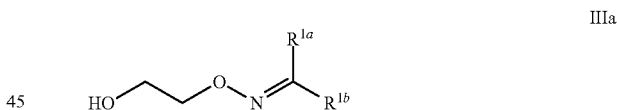

IIIa wherein $R^{1a}$ and $R^{1b}$ together with the remainder of formula IIIa are the prodrug of the therapeutic agent. It is to be understood that the prodrug of formula IIIa represents a therapeutic agent of formula IIIb (wherein $R^{1a}$ and $R^{1b}$ and the carbonyl to which they are attached represent a therapeutic agent):

IIIb wherein the ketone or aldehyde of the therapeutic agent of formula IIIb has been condensed with the aminooxy moiety of $HO-(CH_2)_2-O-NH_2$ to arrive at the prodrug of the therapeutic agent of formula IIIa.

In one embodiment a residue of a therapeutic agent (which is a residue of a prodrug of a therapeutic agent) (D or —Z-$D^1$) is a represented by formula IIIc:

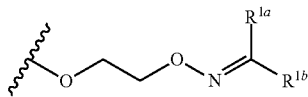

wherein $R^{1a}$ and $R^{1b}$ together with the remainder of formula IIIc are the residue of the therapeutic agent (D or —Z-$D^1$).

One embodiment provides a therapeutic agent which is a prodrug of the therapeutic agent and is represented by formula IIId:

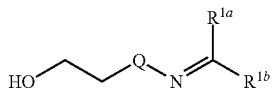

wherein Q is —O— or —NH— and $R^{1a}$ and $R^{1b}$ together with the remainder of formula IIId are the prodrug of the therapeutic agent. It is to be understood that the prodrug of formula IIId represents a therapeutic agent of formula IIIb (wherein $R^{1a}$ and $R^{1b}$ and the carbonyl to which they are attached represent a therapeutic agent):

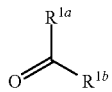

wherein the ketone or aldehyde of the therapeutic agent of formula IIIb has been condensed with the moiety of HO—$(CH_2)_2$-Q-$NH_2$ to arrive at the prodrug of the therapeutic agent of formula IIId.

In one embodiment a residue of a therapeutic agent (which is a residue of a prodrug of a therapeutic agent) (D or —Z-$D^1$) is a represented by formula IIIe:

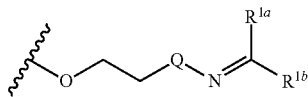

wherein Q is —O— or —NH— and $R^{1a}$ and $R^{1b}$ together with the remainder of formula IIIe are the residue of the therapeutic agent (D or —Z-$D^1$).

In one embodiment -L-D is a represented by the formula:

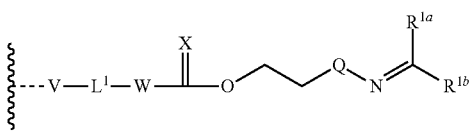

wherein V, $L^1$, W and X have the values described herein and Q is —O— or —NH— and $R^{1a}$ and $R^{1b}$ together with —O—$(CH_2)_2$-Q-N=C are the residue of the prodrug of the therapeutic agent.

In one embodiment -L-D is a represented by the formula:

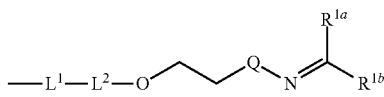

wherein $L^1$, $L^2$ have the values described herein and Q is —O— or —NH— and $R^{1a}$ and $R^{1b}$ together with —O—$(CH_2)_2$-Q-N=C are the residue of the prodrug of the therapeutic agent.

In one embodiment -L-D is a represented by the formula:

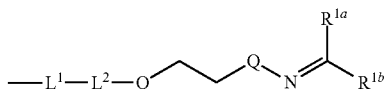

wherein $L^1$ has the values described herein, $L^2$ has the values described herein provided Y is absent and Q is —O— or —NH— and $R^{1a}$ and $R^{1b}$ together with —O—$(CH_2)_2$-Q-N=C are the residue of the prodrug of the therapeutic agent.

PBS:acetonitrile (0.75 mL) at pH 7.4 were irradiated with an AMF (501.6 amps, 204 kHz) for 5-minute bursts followed by 5-minute intervals. Vertical axis shows fluorescence intensity normalized to µmol of bound anthracene fluorophore as determined by thermogravimetric analysis.

Figure 16:
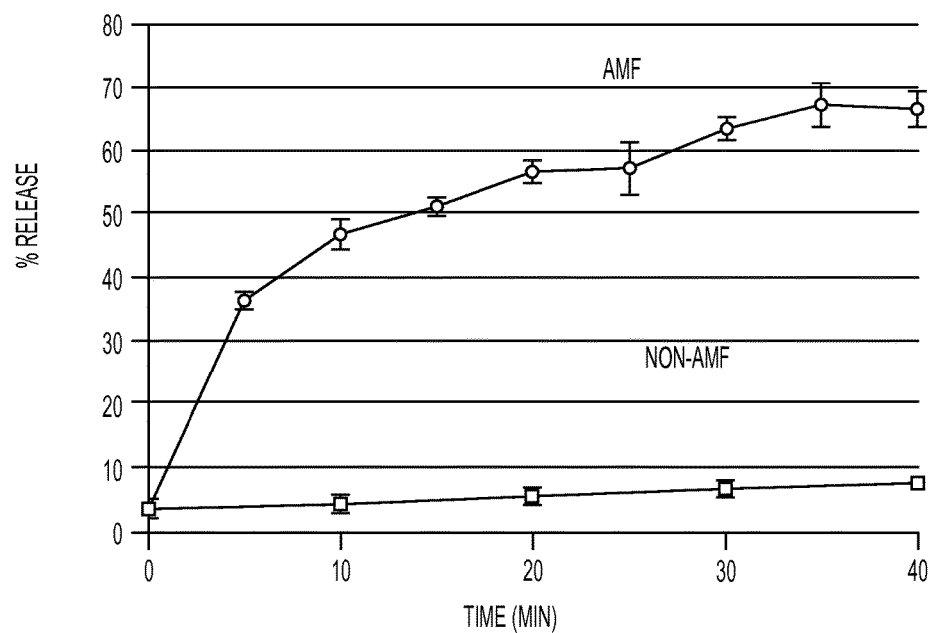

FIG. 16 AMF-induced release of 11 from FL@SiO$_2$@Fe$_3$O$_4$: NPs in PBS:acetonitrile were irradiated with an AMF (501.6 amps, 204 kHz) for 5-minute bursts followed by 5-minute intervals; release of 11 from FL@SiO$_2$@Fe$_3$O$_4$: NPs in PBS:acetonitrile were incubated at 37° C. for the indicated time. Vertical axis shows the percent of 11 released as determined by fluorescent measurements; n=3.

Figure 17:
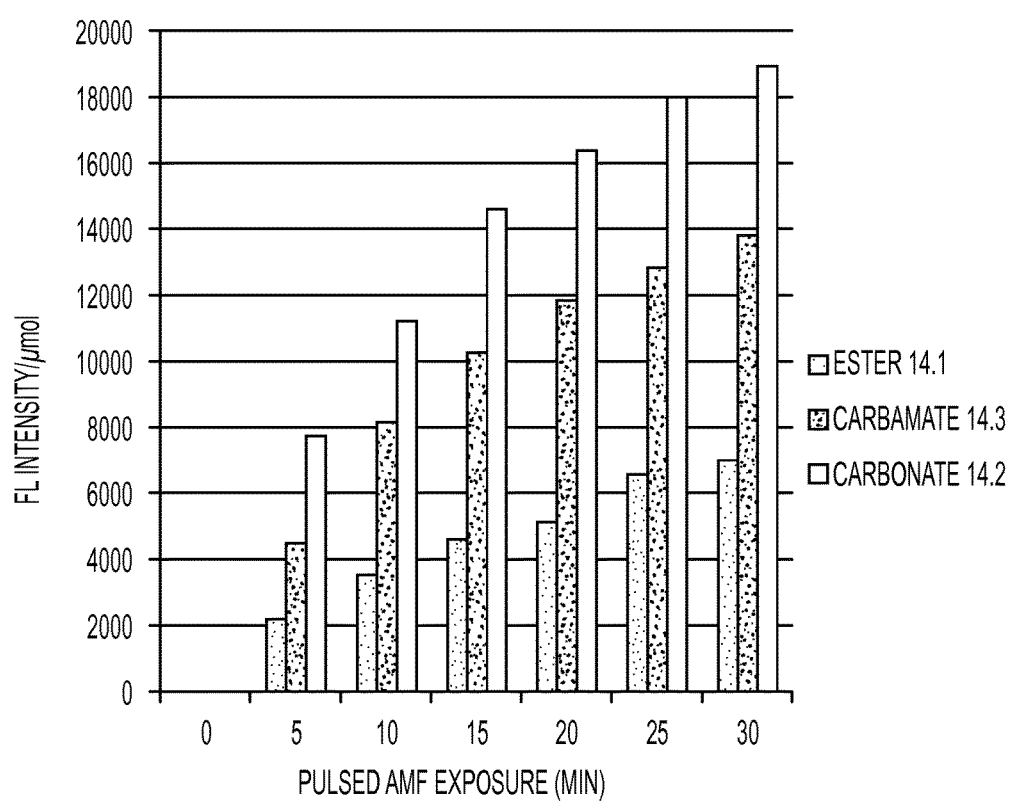

FIG. 17 illustrates the Pulsed AMF-induced hydrolysis of an ester (bar on left), carbamate (bar in the middle) and carbonate (bar on the right) bound to Fe$_3$O$_4$ NPs in 2:1 PBS:MeCN. AMF was set at 200 amps and 204 kHz.

Figure 18:
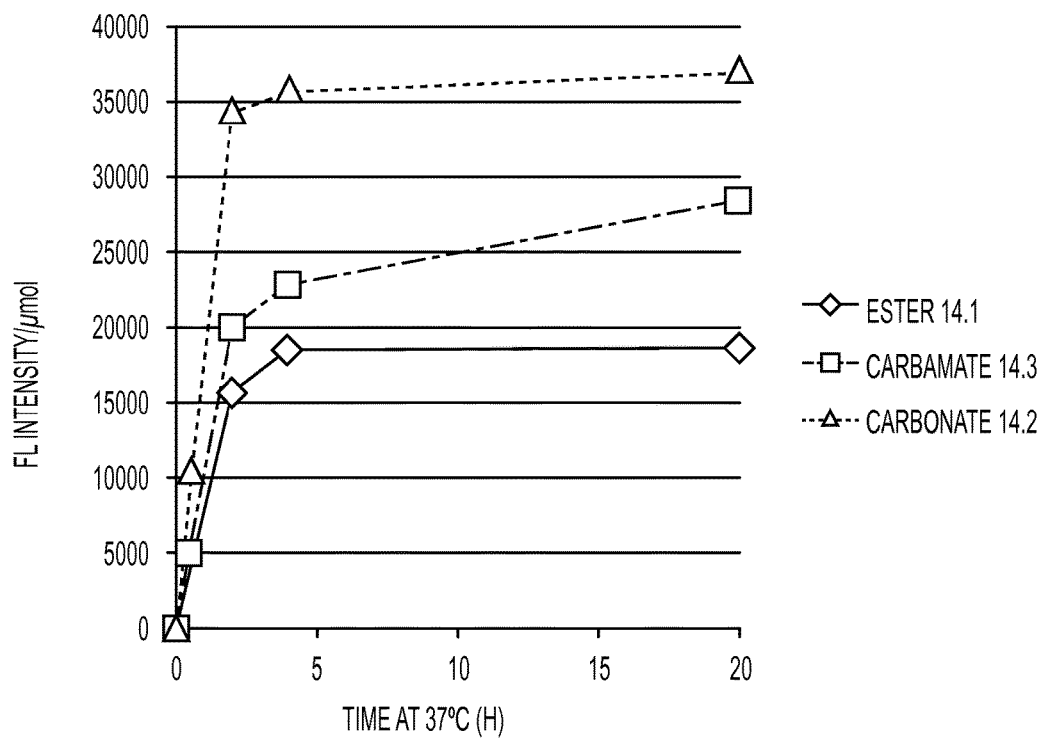

FIG. 18 illustrates the hydrolysis of an ester, carbamate and carbonate bound to Fe$_3$O$_4$ NPs without AMF. Functionalized NPs were incubated at 37° C. in 2:1 PBS:MeCN for 20 h.

Figure 19:
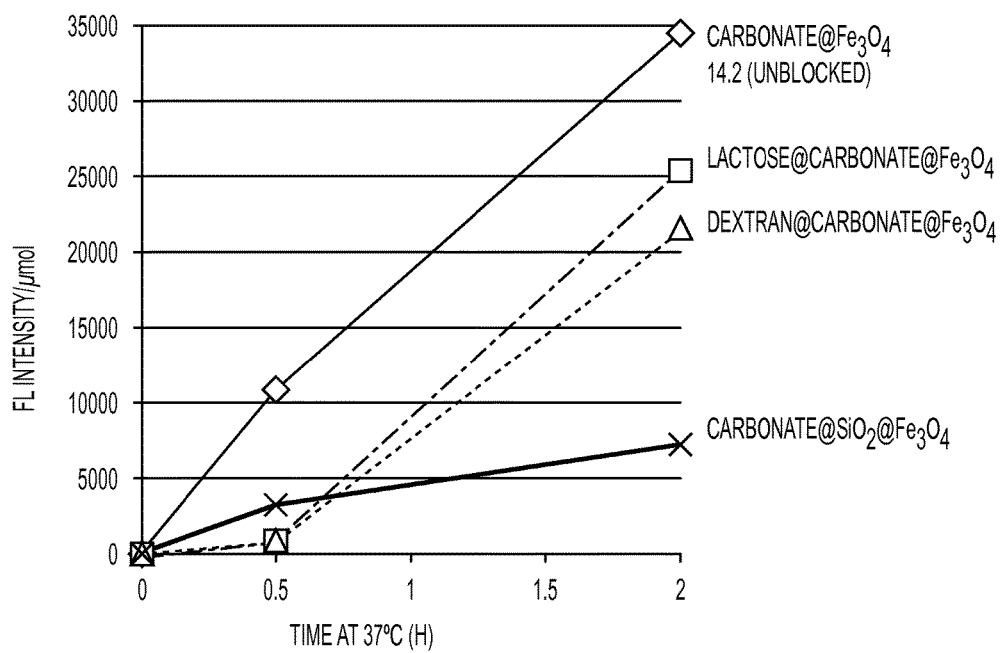

FIG. 19 illustrates the suppression of hydrolysis at 37° C. by restricting access to Fe$_3$O$_4$ core in 2:1 PBS:MeCN.

Figure 20A:
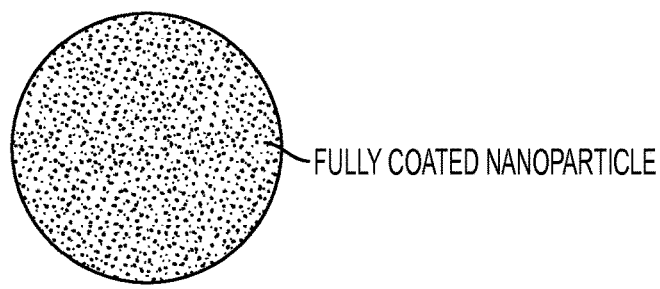
Figure 20B:
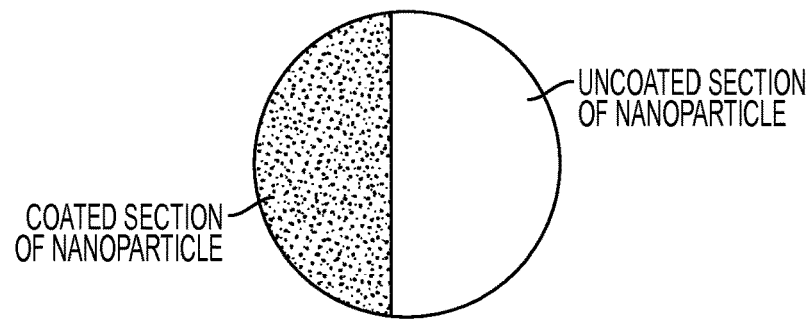
Figure 20C:
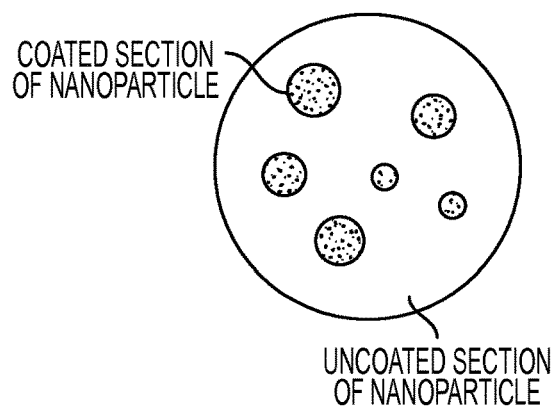

FIG. 20 illustrates a coated magnetic nanoparticle. FIG. 20A illustrates a fully coated magnetic nanoparticle; FIG. 20B illustrates a partially coated magnetic nanoparticle; and FIG. 20C illustrates a partially coated magnetic nanoparticle wherein the coating is non-contiguous (for example spotted).

Figure 21:
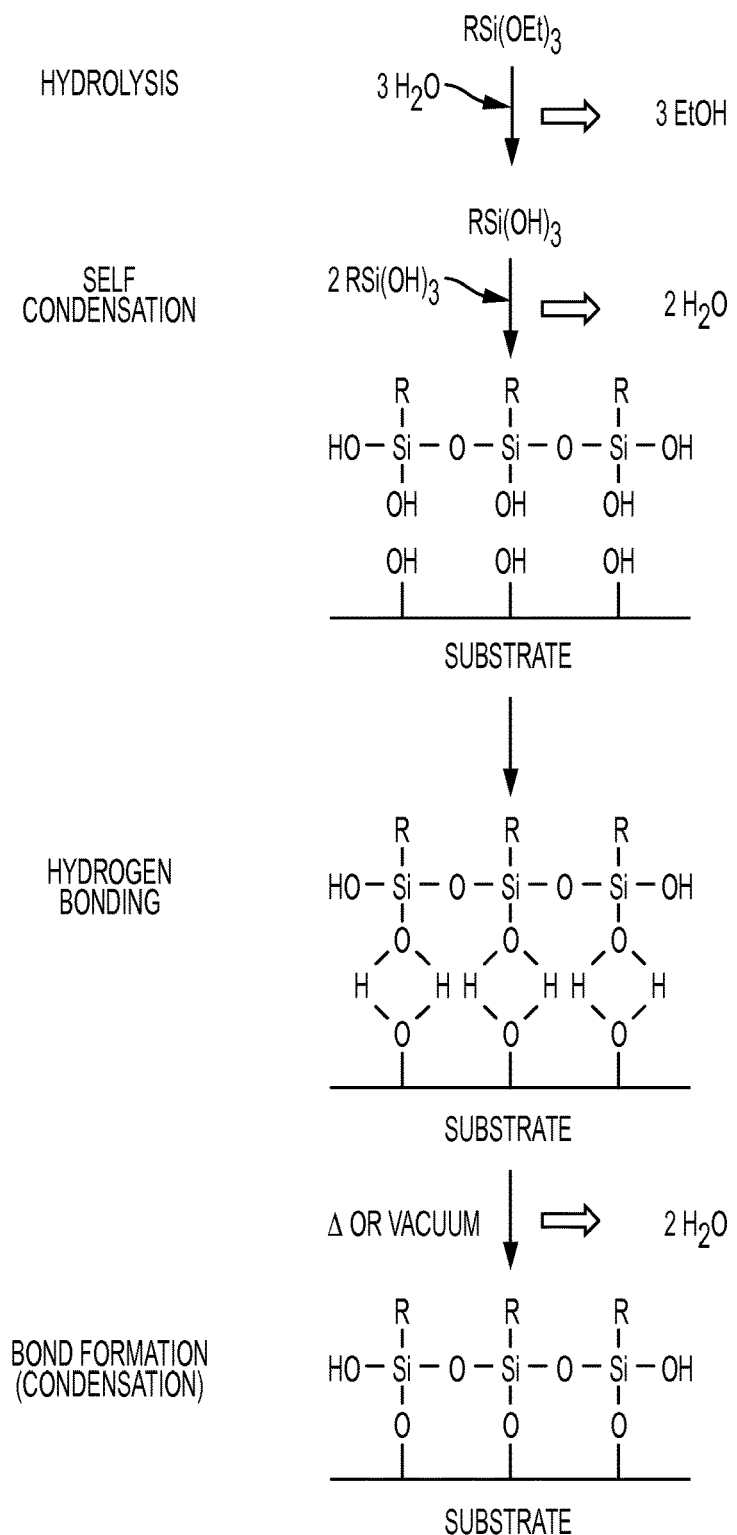

FIG. 21 illustrates the hydrolysis and condensation loading of alkoxysilane.

Figure 22:
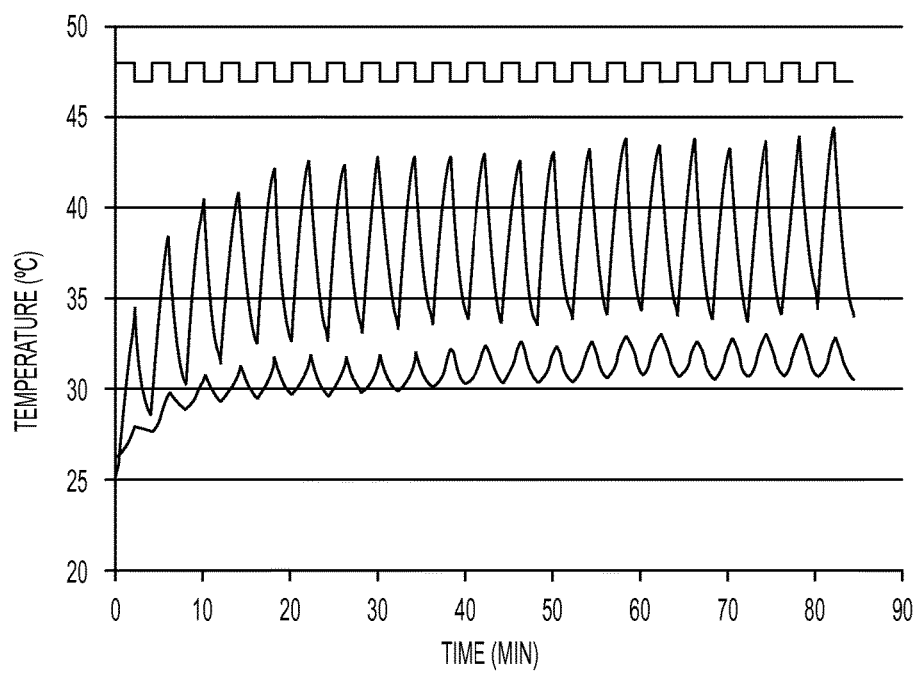

FIG. 22 illustrates the AMF-induced heating/cooling of 2:1 PBS:acetonitrile (0.75 mL) (bottom line), SiO$_2$@Fe$_3$O$_4$ NPs (7 mg) in 2:1 PBS:acetonitrile (0.75 mL) (middle line), AMF 2 min on/off sequence (top line). AMF conditions: 500 amps, 204 kHz.

Figure 23:
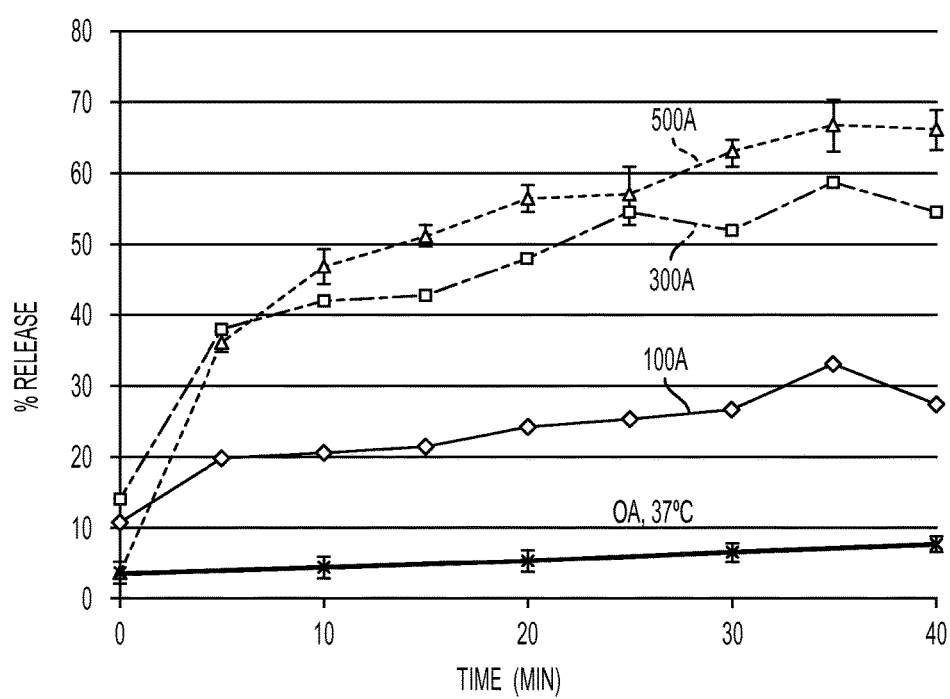

FIG. 23 illustrates the AMF-induced release, as determined by fluorescence measurements, of 11 from FL@SiO$_2$@Fe$_3$O$_4$ NPs in 2:1 PBS:acetonitrile at AMF amperages of 100.7 (n=1), 300.2 (n=1) or 501.6 (n=3). The control, incubated at 37° C. for the indicated time, received no AMF pulses.

Figure 24:
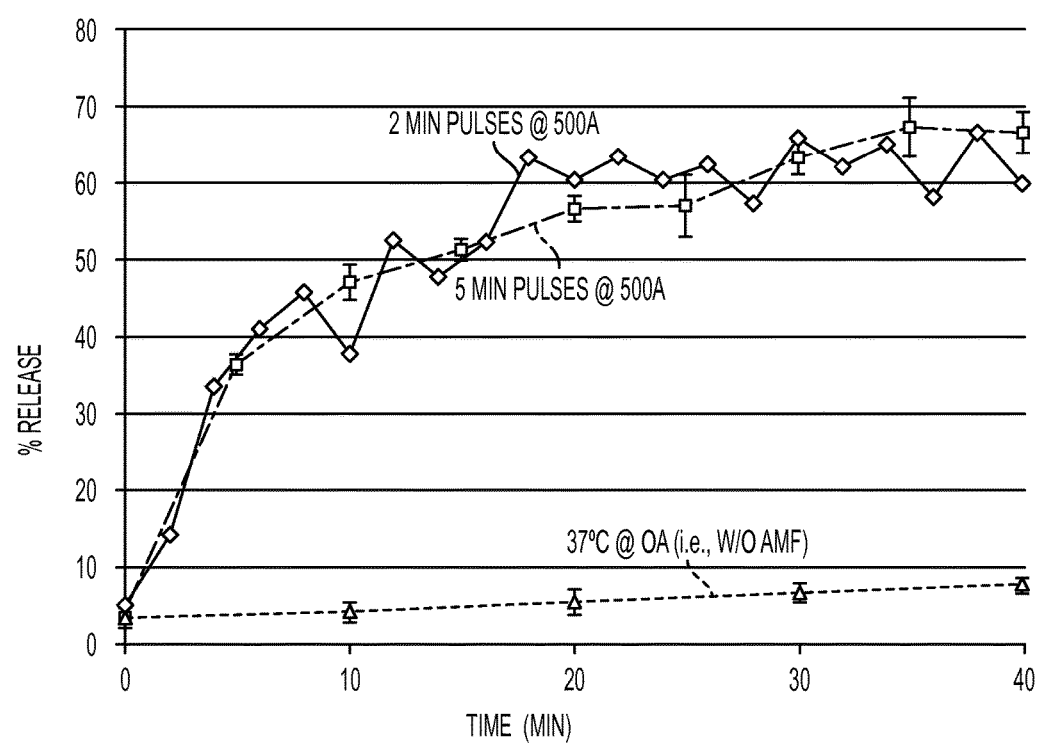

FIG. 24 illustrates AMF-induced release of 11 from FL@SiO$_2$@Fe$_3$O$_4$ NPs during 2 minute (n=1) or 5 minute (n=3) AMF pulses at 501.6 amps versus incubation at 37° C.

DETAILED DESCRIPTION

Described herein are therapeutic magnetic nanoparticle drug delivery systems that are designed to reduce the problem of payload leakage. Magnetic nanoparticles can be covalently attached to a molecular linker wherein the linker is also covalently bound to a therapeutic agent (e.g., drug) through a functional group such as but not limited to an ester, carbonate or carbamate functional group. It has been discovered that therapeutic magnetic nanoparticles that link a therapeutic agent to a magnetic nanoparticle through a linker and a stable functional group can be induced to release (e.g., hydrolysis of the functional group) the therapeutic agent. In one embodiment the heat generated by the magnetic nanoparticle on AMF exposure induces separation of the therapeutic agent from the linker (e.g., through breaking the bond(s) of the functional group that connects the linker to the therapeutic agent). In one embodiment the functional group is hydrolyzed (e.g., by water or hydroxide ion) thereby releasing the therapeutic agent from the linker. This release mechanism provides a platform for the purposes of drug delivery with both spatial and temporal control.

Also described herein is an alternative therapeutic magnetic nanoparticle drug delivery system that is designed to reduce the problem of payload leakage. Magnetic nanoparticles can be covalently attached to a molecular linker containing a protected amine wherein the linker is also covalently bound to a therapeutic agent (e.g., drug) through a functional group such as through an ester, carbonate or carbamate functional group. By placing the protected amine at a specified distance from the ester, carbonate or carbamate carbonyl functional group, the protected amine can undergo deprotection followed by intramolecular cyclization, thereby releasing the bound therapeutic agent. In one embodiment the heat generated by the magnetic nanoparticle on AMF exposure induces the deprotection and thereby the subsequent intramolecular cyclization. This release mechanism also provides a platform for the purposes of drug delivery with both spatial and temporal control.

It is possible to target the therapeutic magnetic nanoparticles to a specific location in a patient's body, e.g., by magnetically guiding the nanoparticles to the target tissue and/or by conjugating appropriate targeting elements (e.g., an antibody fragment, a small molecule ligand of a cellular receptor) to the therapeutic nanoparticle.

In certain embodiments, the nanoparticles can be magnetically guided to the desired location in the body of the patient. This delivery system provides a method for delivering therapeutic agents including agents that are toxic when administered systemically by allowing for targeting of the drug to a specific location. Thus, this system is particularly useful for delivering drugs that are beneficially delivered to a specific location at a high concentration, e.g., anticancer, antibiotic, antifungal, antiparasitic, and antiviral drugs. An advantage of this delivery system is the delivery of a therapeutic agent to a specific location and the release of the therapeutic agent at a specific time through the selective heating of the magnetic nanoparticle by exposure to an AMF.

The following definitions are used, unless otherwise described.

Magnetic Nanoparticle.

Magnetic nanoparticles include any nanoparticles that possess paramagnetic or superparamagnetic (SPM) properties such as those paramagnetic or SPM properties of nanoparticles that comprise iron (iron nanoparticles) which for example include nanoparticles that comprise iron oxide (e.g., iron oxide nanoparticles). The desirable paramagnetic or superparamagnetic (SPM) properties include properties that make the magnetic nanoparticle responsive to a magnetic field (e.g., the magnetic nanoparticles will heat when exposed to an AMF). Thus, magnetic nanoparticles include iron nanoparticles such as nanoparticles comprising iron oxide (e.g., Fe$_3$O$_4$, the partially oxidized preparations Fe$_2$O$_3$/Fe$_3$O$_4$ or the fully oxidized Fe$_2$O$_3$). Magnetic nanoparticles also include metal alloys that possess the desired paramagnetic or superparamagnetic (SPM) properties such as those paramagnetic and SPM properties of iron nanoparticles (e.g., iron oxide nanoparticles). Accordingly the term "magnetic nanoparticle" includes nanoparticle alloys, that possess magnetic properties such as but not limited to alloys of iron oxide (for a discussion on magnetic nanoparticle alloys see: Tang, Q., et al., Using Thermal Energy Produced by Irradiation of Mn—Zn Ferrite magnetic Nanoparticles (MZF-NPs) for Heat-Inducible Gene Expression. *Biomaterials* 2008, 29, 2673-2679 which reference is incorporated herein in its entirety). It is to be understood that the amount of magnetic material (such as iron) in a magnetic nanoparticle can vary as long as the nanoparticle possesses the desired magnetic properties. Magnetic nanoparticles also include magnetic nanoparticles that are coated (e.g., coated magnetic nanoparticles) by another substance or material such as but not limited to gold, graphene or silica. As used herein the term "coated magnetic nanoparticle" includes magnetic nanoparticles wherein the surface of the magnetic nanoparticle is coated (e.g., fully or partially) by the substance or material. It is to be understood the surface of the coated magnetic nanoparticle may be fully coated or partially coated and that when the coated magnetic nanoparticle is partially coated the coating may or may not be contiguous and the coating may be of any shape (e.g., spotted). In one embodiment the surface is at least 1%, at least 10%, at least 20%, at least 40%, at least 60%, at least 80%, at least 90% or completely covered by the substance or material. In one embodiment the core of a coated magnetic nanoparticle is magnetic but the coating may not be magnetic. In one embodiment the magnetic nanoparticle is coated with two or more different coatings. The size of the magnetic nanoparticle can vary. In one embodiment the size of the magnetic nanoparticle is about 1-750 nM in diameter. In one embodiment the size of the magnetic nanoparticle is about 1-500 nM in diameter. In one embodiment the size of the magnetic nanoparticle is about 1-250 nM in diameter. In one embodiment the size of the magnetic nanoparticle is about 1-150 nM in diameter. In one embodiment the size of the magnetic nanoparticle is about 1-50 nM in diameter. In one embodiment the size of the magnetic nanoparticle is about 5-750 nM in diameter. In one embodiment the size of the magnetic nanoparticle is about 5-500 nM in diameter. In one embodiment the size of the magnetic nanoparticle is about 5-250 nM in diameter. In one embodiment the size of the magnetic nanoparticle is about 5-150 nM in diameter. In one embodiment the size of the magnetic nanoparticle is about 5-50 nM in diameter.

Linker.

As described herein, the magnetic nanoparticles can be connected to a therapeutic agent through a linker. The linker can be (a) covalently bonded to the magnetic nanoparticle by at least one atom of the linker and (b) covalently bonded to a therapeutic agent at another atom of the linker. Thus, the linker can be covalently bonded to the magnetic nanoparticle or if the magnetic nanoparticle is coated it can be covalently bonded to the coating. It is also to be understood that if a magnetic nanoparticle is coated some of the linkers can be covalently bonded to the coating and some of the linkers can be covalently bonded to the magnetic nanoparticle. For example, the linker can be covalently bonded to the iron oxide magnetic nanoparticle through a silicon atom of the linker. The linker can also be bonded to a coated magnetic nanoparticle, such as a silica coated magnetic nanoparticle through a silicon atom of the linker. The linker can also be bonded to a coated magnetic nanoparticle, such as a gold-coated magnetic nanoparticle. For example, a sulfur atom of a linker can be covalently bonded to a gold atom of a gold-coated magnetic nanoparticle. The linker can be bonded to the magnetic nanoparticle wherein the magnetic nanoparticle is further coated; thus the magnetic nanoparticle is coated but the linker is bonded to the magnetic nanoparticle and not the coating.

In one embodiment the linker can be covalently bound to the therapeutic agent via a functional group (e.g., ester, amide, carbonate, carbamate, urea, thioester, thioamide, thiocarbonate, thiocarbamate, thiourea) that allows the therapeutic agent to be separated from linker when a bond connecting the functional group to therapeutic agent is broken (e.g., through the hydrolysis of the functional group). In one embodiment the linker is not capable of undergoing intramolecular cyclization. In one embodiment the hydrolysis is facilitated by heat. In one embodiment the hydrolysis is facilitated by AMF.

In one embodiment the linker can be covalently bound to the therapeutic agent via a functional group (e.g., ester, amide, carbonate, carbamate, urea, thioester, thioamide, thiocarbonate, thiocarbamate, thiourea) that allows the therapeutic agent to be cleaved from the functional group when the linker containing a protected amine undergoes deprotection and intramolecular cyclization as described herein (a protected amine is deprotected to provide a nucleophilic amine that undergoes intramolecular cyclization). The therapeutic agent is generally connected to a carbonyl or thiocarbonyl moiety of the functional group via a labile bond. Thus, when the linker undergoes intramolecular cyclization the bond connecting the therapeutic agent to the carbonyl or thiocarbonyl moiety (for example a bond such as an oxygen, nitrogen or sulfur bonded to either the carbonyl or thiocarbonyl) of the functional group is broken thereby releasing the therapeutic agent from the linker. In one embodiment, the linker, upon heating (e.g., upon AMF irradiation of the attached magnetic NP), undergoes amine deprotection and intramolecular cyclization thereby releasing the therapeutic agent from the linker. The intramolecular cyclization generally occurs through reaction of an amine nitrogen within the linker and the carbon of the carbonyl carbon or thiocarbonyl carbon of the functional group that connects the therapeutic agent to the linker.

The linkers described herein can vary in length and composition and be branched or non-branched. In one embodiment the linker is a chain (non-cyclic) that is branched or non-branched.

In one embodiment the linker comprises about 4-50 atoms in the linker. In one embodiment the linker comprises about 4-40 atoms in the linker. In one embodiment the linker comprises about 4-30 atoms in the linker. In one embodiment the linker comprises about 4-20 atoms in the linker. In one embodiment the linker comprises about 4-15 atoms in the linker. In one embodiment the linker comprises about 7-50 atoms in the linker. In one embodiment the linker comprises about 7-40 atoms in the linker. In one embodiment the linker comprises about 7-30 atoms in the linker. In one embodiment the linker comprises about 7-20 atoms in the linker. In one embodiment the linker comprises about 7-15 atoms in the linker. In one embodiment the linker comprises about 6-15 atoms in the linker. In one embodiment the linker comprises about 7-14 atoms in the linker. In one embodiment the linker comprises about 8-14 atoms in the linker. In one embodiment the linker comprises about 9-13 atoms in the linker. In one embodiment any of the above the atoms are independently selected from carbon, nitrogen, oxygen, sulfur and silicon. In one embodiment any of the above the atoms are independently selected from carbon, nitrogen, oxygen, sulfur and silicon provided the linker contains at least one protected amine and one group selected from (C=O) and (C=S). In one embodiment no oxygen, nitrogen, silicon or sulfur are directed bonded (e.g., adjacent) to another oxygen, nitrogen, silicon or sulfur. In one embodiment no oxygen, nitrogen or sulfur are directed bonded (e.g., adjacent) to another oxygen, nitrogen or sulfur. In one embodiment the linker is covalently attached to the magnetic nanoparticle or the coated magnetic nanoparticle by a silicon or sulfur atom. It is to be understood that the atoms that make up the linker include hydrogen atoms to fulfill the valency requirements of any carbon, nitrogen, oxygen, sulfur and silicon atom of the linker. Thus, any of the atoms of the linker are independently selected from carbon, nitrogen, oxygen, sulfur, silicon and hydrogen. In one embodiment the linker comprises about 12-150 atoms in the linker. In one embodiment the linker comprises about 12-120 atoms in the linker. In one embodiment the linker comprises about 12-90 atoms in the linker. In one embodiment the linker comprises about 12-60 atoms in the linker. In one embodiment the linker comprises about 12-45 atoms in the linker. In one embodiment the linker comprises about 21-150 atoms in the linker. In one embodiment the linker comprises about 21-120 atoms in the linker. In one embodiment the linker comprises about 21-90 atoms in the linker. In one embodiment the linker comprises about 21-60 atoms in the linker. In one embodiment the linker comprises about 14-45 atoms in the linker. In one embodiment the linker comprises about 18-45 atoms in the linker. In one embodiment the linker comprises about 21-42 atoms in the linker. In one embodiment the linker comprises about 24-42 atoms in the linker. In one embodiment the linker comprises about 27-39 atoms in the linker. In one embodiment, for any of the above embodiments the linker is the atom range specified.

It is to be understood that the magnetic nanoparticle may be bonded with multiple linker groups and that some of these groups are adjacent (e.g., in close proximity) to one another. In such situations it is possible that certain groups of the adjacent linkers may interact (e.g., be bonded to each other). One example of this would include linkers which comprise a silicon atom wherein the silicon atoms on adjacent linkers can be connected to one another via a bridging oxygen atom (e.g., —O—).

Therapeutic Agent

The term "therapeutic agent" includes agents that are useful for the treatment of a disease or a physiological condition in an animal (e.g., a mammal such as a human) and thus includes known drugs. Thus, the term "therapeutic agent" includes but is not limited to known drugs and/or drugs that have been approved for sale in the United States. For example, therapeutic agents include but are not limited to chemotherapeutic agents, antibiotic agents, antifungal agents, antiparasitic agents and antiviral agents. The term "therapeutic agent" also includes "prodrugs" of such therapeutic agents or drugs. The term "therapeutic agent" also includes functional group derivatives of such therapeutic agents or drugs. Such functional group derivatives include for example, but are not be limited to, alcohols of the corresponding ketone of a therapeutic agent. Accordingly, the term "therapeutic agent" includes a therapeutic agent, a prodrug of a therapeutic agent and a functional group derivative of therapeutic agent. It is to be understood that the bond between the therapeutic agent and the linker can be at any suitable atom of the therapeutic agent such as (a) the therapeutic agent itself, (b) the prodrug portion of the prodrug of a therapeutic agent or (c) the functional group derivative portion of the functional group derivative of a therapeutic agent.

The therapeutic agent can be connected to the linker described herein by the removal of a hydrogen atom from the therapeutic agent (e.g., a residue of a therapeutic agent) which provides the open valency to be connected to the linker. In one embodiment the term —Z-$D^1$ of formula I can be a residue of a therapeutic agent and the corresponding group H—Z-$D^1$ can be the corresponding therapeutic agent. In one embodiment the term D of formula I can be a residue of a therapeutic agent and the corresponding group H-D can be the corresponding therapeutic agent. In one embodiment the term D of formula I can be a residue of a prodrug of a therapeutic agent. Thus, one embodiment provides therapeutic agents comprising one or more hydroxyl (—OH), thiol (—SH) or amine (e.g., primary (—$NH_2$) or secondary (—NH—, —NH($C_1$-$C_6$)alkyl), groups which groups can be connected to the linker as described herein.

In one embodiment D together with Y of $L^2$ or D together with W—C(=X)—Y of $L^2$ is the moiety:

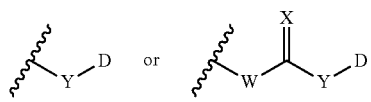

wherein the moiety is a residue of a therapeutic agent. In one embodiment the corresponding therapeutic agent of the residue of the therapeutic agent described in the preceding embodiment is a therapeutic agent of the formula

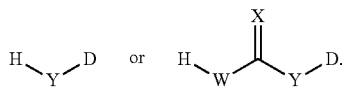

In one embodiment the therapeutic agent is a therapeutic agent (e.g., a drug) or a prodrug of the therapeutic agent.

In one embodiment the therapeutic agent is a therapeutic agent (e.g., drug) and not a prodrug and not a functional group derivative of the therapeutic agent.

In one embodiment the therapeutic agent is selected from Cladribine, Azacitidine, Abraxane, Adcetris, Doxorubicin, Afinitor, Vinblastine, Amifostine, Amifostine, Arabinosylcytosine, Cytarabine, Pamidronic Acid, Nelarabine, Bicalutamide, Blemycin, Bortezomib, Cabazitaxel, Irinotecan, Camptothecin, Capecitabine, Temsirolimus, Daunorubicin, Cortisone, Decitabine, Dasatinib, Dexamethasone, Prednisolone, Dexamethasone Acetate, Mitoxantrone, Docetaxel, Hydroxycarbamide, Methylprednisolone, Epirubicin, Curcumin, Estramustine, Eribulin, Etoposide, Everolimus, Raloxifene, Fulvestrant, Floxuridine, Fludarabine, Fluoxymesterone, Gemcitabine, Goserelin, Topotecan, Hydrocortisone, Hydrocortone Phosphate, Idarubicin, Ixabepilone, Vincristine, Leuprolide (Leuprorelin), Megestrol, Vinorelbine, Nelarabine, Pentostatin, Octreotide, Paclitaxel, Streptozotocin, Teniposide, Valrubicin, Vorinostat, Zoledronic Acid Cladribine, Azacitidine, Mecaptopurine, Tioguanine, Actinomycin D, Doxorubicin, Anagrelide, Pemetrexed, Vinblastine, Melphalan, Methotrexate, Amifostine, Aminoglutethimide, Arabinosylcytosine, Cytarabine, Pamidronic Acid, Nelarabine, Axitinib, Bleomycin, Bosutinib, Folinic Acid (Na or Ca), Leucovorin, Vandetanib, Lenalidomide, Daunorubicin, Crizotinib, Dacarbazine, Decitabine, Dasatinib, Mitoxantrone, Eribulin, Erlotinib, Fludarabine, Pralatrexate, Gefitinib, Gemcitabine, Imatinib, Goserelin, Idarubicin, Lapatinib, Vincristine, Leuprolide, Procarbazine, Methotrexate, Mitomycin, Vinorebine, Nelarabine, Nilotinib, Pentostatin, Octreotide, Pazopanib, Sunitinib, Abraxane, Actinomycin D, Doxorubicin, Afinitor, Exemestane, Carfilzomib, Daunorubicin, Cortisone, Prednisolone, Prednisone, Dexamethasone Acetate, Docetaxel, Methylprednisolone, Epirubicin, Curcumin, Everolimus, Fluoxymesterone, Hydrocortisone, Hydrocortone Phosphate, Idarubicin, Ixabepilone, Vincristine. Megestrol, Valrubicin, Mesna, 13-cis-Retinoic Acid, Isotretinoin, Alitretinoin, Melphalan, Tretinoin, Methotrexate, Anastrozole, Bendamustine, Bexarotene, Carmustine, Lomustine, Chlorambucil and IbritumomabTiuxetan.

In one embodiment the therapeutic agent is a chemotherapeutic agent, an antibiotic agent, an antifungal agent, an antiparasitic agent or an antiviral agent or a prodrug thereof.

In one embodiment the therapeutic agent is a chemotherapeutic agent, an antibiotic agent, an antifungal agent, an antiparasitic agent or an antiviral agent.

In one embodiment the therapeutic agent has at least one amine (e.g., —NH$_2$ or —NH(C$_1$-C$_6$)alkyl), hydroxy or a thiol group.

In one embodiment the therapeutic agent has at least one hydroxy (—OH), thiol (—SH) or amine (e.g., primary (—NH$_2$) or secondary (—NH—, —NH(C$_1$-C$_6$)alkyl)) group.

In one embodiment the therapeutic agent has at least one hydroxy (—OH), thiol (—SH) or amine (e.g., primary (—NH$_2$) or secondary (—NH—)) group.

In one embodiment the therapeutic agent has at least one hydroxy or thiol group.

In one embodiment the therapeutic agent has at least one hydroxy group.

In one embodiment the therapeutic agent has at least one amine (e.g., —NH$_2$ or —NH(C$_1$-C$_6$)alkyl), hydroxy (—OH) or a thiol group and is attached to the linker through the amine (e.g., —NH$_2$ or —NH(C$_1$-C$_6$)alkyl), hydroxy (—OH) or a thiol group of the therapeutic agent.

In one embodiment the therapeutic agent has at least one hydroxyl (—OH), thiol (—SH) or amine (e.g., primary (—NH$_2$) or secondary (—NH—, —NH(C$_1$-C$_6$)alkyl)) group and is attached to the linker through the hydroxyl (—OH), thiol (—SH) or amine (e.g., primary (—NH$_2$) or secondary (—NH—, —NH(C$_1$-C$_6$)alkyl)) group of the therapeutic agent.

In one embodiment the therapeutic agent has at least one hydroxy (—OH), thiol (—SH) or amine (e.g., primary (—NH$_2$) or secondary (—NH—)) group and is attached to the linker through the hydroxyl (—OH), thiol (—SH) or amine (e.g., primary (—NH$_2$) or secondary (—NH—)) group of the therapeutic agent.

In one embodiment the therapeutic agent has at least one hydroxy or thiol (—SH) group and is attached to the linker through the hydroxy (—OH) or thiol (—SH) group of the therapeutic agent.

In one embodiment the therapeutic agent has at least one hydroxy group (—OH) and is attached to the linker through the hydroxy (—OH) group of the therapeutic agent.

In one embodiment the therapeutic agent has at least one amine (e.g., primary (—NH$_2$) or secondary (—NH—)) and is attached to the linker through the amine (e.g., primary (—NH$_2$) or secondary (—NH—)) group of the therapeutic agent.

In one embodiment the therapeutic agent has at least one thiol (—SH) group and is attached to the linker through the thiol (—SH) group of the therapeutic agent.

In one embodiment the therapeutic agent has at least one ketone or aldehyde.

In one embodiment the therapeutic agent has at least one ketone or aldehyde and is attached to the linker through the ketone or aldehyde group (or the corresponding imine) of the therapeutic agent.

In one embodiment the therapeutic agent is selected from Cladribine, Azacitidine, Abraxane, Adcetris, Doxorubicin, Afinitor, Vinblastine, Amifostine, Amifostine, Arabinosylcytosine, Cytarabine, Pamidronic Acid, Nelarabine, Bicalutamide, Blemycin, Bortezomib, Cabazitaxel, Irinotecan, Camptothecin, Capecitabine, Temsirolimus, Daunorubicin, Cortisone, Decitabine, Dasatinib, Dexamethasone, Prednisolone, Dexamethasone Acetate, Mitoxantrone, Docetaxel, Hydroxycarbamide, Methylprednisolone, Epirubicin, Curcumin, Estramustine, Eribulin, Etoposide, Everolimus, Raloxifene, Fulvestrant, Floxuridine, Fludarabine, Fluoxymesterone, Gemcitabine, Goserelin, Topotecan, Hydrocortisone, Hydrocortone Phosphate, Idarubicin, Ixabepilone, Vincristine, Leuprolide (Leuprorelin), Megestrol, Vinorelbine, Nelarabine, Pentostatin, Octreotide, Paclitaxel, Streptozotocin, Teniposide, Valrubicin, Vorinostat and Zoledronic Acid.

In one embodiment the therapeutic agent is selected from Cladribine, Azacitidine, Mecaptopurine, Tioguanine, Actinomycin D, Doxorubicin, Anagrelide, Pemetrexed, Vinblastine, Melphalan, Methotrexate, Amifostine, Aminoglutethimide, Arabinosylcytosine, Cytarabine, Pamidronic Acid, Nelarabine, Axitinib, Bleomycin, Bosutinib, Folinic Acid (Na or Ca), Leucovorin, Vandetanib, Lenalidomide, Daunorubicin, Crizotinib, Dacarbazine, Decitabine, Dasatinib, Mitoxantrone, Eribulin, Erlotinib, Fludarabine, Pralatrexate, Gefitinib, Gemcitabine, Imatinib, Goserelin, Idarubicin, Lapatinib, Vincristine, Leuprolide, Procarbazine, Methotrexate, Mitomycin, Vinorebine, Nelarabine, Nilotinib, Pentostatin, Octreotide, Pazopanib and Sunitinib.

In one embodiment the therapeutic agent is selected from Abraxane, Actinomycin D, Doxorubicin, Afinitor, Exemestane, Carfilzomib, Daunorubicin, Cortisone, Prednisolone, Prednisone, Dexamethasone Acetate, Docetaxel, Methylprednisolone, Epirubicin, Curcumin, Everolimus, Fluoxymesterone, Hydrocortisone, Hydrocortone Phosphate, Idarubicin, Ixabepilone, Vincristine, Megestrol, Valrubicin and Mesna.

In one embodiment the therapeutic agent is selected from 13-cis-Retinoic Acid, Isotretinoin, Alitretinoin, Melphalan, Tretinoin, Methotrexate, Bendamustine, Bexarotene, Chlorambucil, and Ibritumomab Tiuxetan.

In one embodiment the therapeutic agent is selected from Carmustine, Lomustine, Chlorambucil and Bendamustine.

Targeting elements (e.g., an antibody fragment, a small molecule ligand of a cellular receptor) can be attached to the therapeutic nanoparticle at any suitable location including the magnetic nanoparticle (directly to nanoparticle or coating of nanoparticle), linker or therapeutic agent by any suitable means.

"Prodrug" of a therapeutic agent refers to a labile functional group which separates from the active compound during metabolism, systemically, inside a cell, by hydrolysis, enzymatic cleavage, or by some other process (Bundgaard, Hans, "Design and Application of Prodrugs" in A Textbook of Drug Design and Development (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug may include an active metabolite of drug itself.

"Alkyl" is a straight or branched saturated hydrocarbon. For example, an alkyl group can have 1 to 8 carbon atoms (i.e., (C$_1$-C$_8$)alkyl) or 1 to 6 carbon atoms (i.e., (C$_1$-C$_6$ alkyl) or 1 to 4 carbon atoms. "Alkylene" refers to an alkyl group having two monovalent radical centers derived by the removal of two hydrogen atoms from the same or two different carbon atoms of the alkyl.

"Alkenyl" is a straight or branched hydrocarbon with at least one (e.g., one or more) carbon-carbon double bond. For example, an alkenyl group can have 2 to 8 carbon atoms (i.e., $C_2$-$C_8$ alkenyl), or 2 to 6 carbon atoms (i.e., $C_2$-$C_6$ alkenyl). "Alkenylene" refers to an alkenyl group having two monovalent radical centers derived by the removal of two hydrogen atoms from the same or two different carbon atoms of the alkenyl.

"Alkynyl" is a straight or branched hydrocarbon with at least one (e.g., one or more) carbon-carbon, triple bond. For example, an alkynyl group can have 2 to 8 carbon atoms (i.e., $C_2$-$C_8$ alkyne), or 2 to 6 carbon atoms (i.e., $C_2$-$C_6$ alkynyl). "Alkynylene" refers to an alkynyl group having two monovalent radical centers derived by the removal of two hydrogen atoms from the same or two different carbon atoms of the alkyne.

The term "chain" includes any branched or unbranched arrangement of atoms that are bonded together but are not cyclic. Thus chains include by way of example but are not limited to alkyl, alkenyl, alkynyl and heteroalkyl groups.

The term "halo" or "halogen" as used herein refers to fluoro, chloro, bromo and iodo.

The term "carbocycle" or "carbocyclyl" refers to a single saturated (i.e., cycloalkyl) or a single partially unsaturated (e.g., cycloalkenyl, cycloalkadienyl, etc.) all carbon ring having 3 to 7 carbon atoms (i.e. ($C_3$-$C_7$)carbocycle). "Carbocyclene" refers to an carbocycle group having two monovalent radical centers derived by the removal of two hydrogen atoms from the same or two different carbon atoms of the carbocycle.

"Phenylene" refers to a phenyl group having two monovalent radical centers derived by the removal of two hydrogen atoms from two different carbon atoms of the phenyl.

The term "heteroalkyl" as used herein refers to an alkyl as defined herein, wherein one or more of the carbon atoms of the alkyl are replaced by an O, S, or $NR_q$, (or if the carbon atom being replaced is a terminal carbon with an OH, SH or $NR_{q2}$) wherein each $R_q$ is independently H or ($C_1$-$C_6$)alkyl. "Heteroalkylene" refers to a heteroalkyl group having two monovalent radical centers derived by the removal of two hydrogen atoms from a same or two different carbon atoms or an OH, SH or $NHR_q$ of the heteroalkyl.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur. Thus, the term includes 3, 4, 5, 6, 7 or 8-membered single saturated or partially unsaturated rings from about 1 to 7 carbon atoms and from about 1 to 4 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl.

The term "cyclic group" includes any arrangement of atoms that are bonded together that form a cyclic structure. Thus cyclic groups include by way of example but are not limited to carbocycle, phenyl and heterocycle.

Silica (silicon dioxide ($SiO_2$)) includes all forms of silica such as amorphous silica, silica gel, mesoporous silica and fumed silica.

Specific values listed below for radicals, substituents, and ranges are for illustration only; they do not exclude other defined values or other values within defined ranges for the radicals and substituents. It is to be understood that two or more values may be combined.

A specific group of compounds of formula I are compounds wherein V is —OSi(G)$_2$-, the magnetic nanoparticle is optionally coated with silica, and the dashed line represents a covalent bond between the oxygen atom of —OSi(G)$_2$- and the magnetic nanoparticle optionally coated with silica; or V is —S—, the magnetic nanoparticle is magnetic nanoparticle coated with gold, and the dashed line represents a covalent bond between —S— and the magnetic nanoparticle coated with gold.

A specific group of compounds of formula I are compounds wherein V is —OSi(G)$_2$-, the magnetic nanoparticle is coated with silica, and the dashed line represents a covalent bond between the oxygen atom of —OSi(G)$_2$- and the magnetic nanoparticle coated with silica.

A specific group of compounds of formula I are compounds wherein V is —OSi(G)$_2$-, the magnetic nanoparticle is an iron oxide nanoparticle coated with silica, and the dashed line represents a covalent bond between the oxygen atom of —OSi(G)$_2$- and the iron oxide nanoparticle coated with silica.

A specific group of compounds of formula I are compounds wherein V is —OSi(G)$_2$-, the magnetic nanoparticle is an iron oxide nanoparticle, and the dashed line represents a covalent bond between the oxygen atom of —OSi(G)$_2$- and the iron oxide nanoparticle.

A specific group of compounds of formula I are compounds wherein V is —OSi(G)$_2$-, the magnetic nanoparticle is an iron oxide nanoparticle optionally coated with silica, and the dashed line represents a covalent bond between the oxygen atom of —OSi(G)$_2$- and the iron oxide nanoparticle optionally coated with silica.

A specific group of compounds of formula I are compounds wherein V is —OSi(G)$_2$-, the magnetic nanoparticle is an iron oxide nanoparticle coated with silica, and the dashed line represents a covalent bond between the oxygen atom of —OSi(G)$_2$- and the iron oxide nanoparticle coated in silica.

One embodiment provides a therapeutic magnetic nanoparticle linked to a residue of the therapeutic agent with a linker wherein linker includes a protected amine as described in the embodiments E1-E59 below.

E1. A therapeutic magnetic nanoparticle, or a salt thereof, comprising a magnetic nanoparticle covalently bonded to one or more -L-D groups wherein D is a residue of a therapeutic agent and L is a linker that comprises a protected amine wherein the protected amine when deprotected provides an amine which amine is capable of undergoing an intramolecular cyclization.

E2. The therapeutic magnetic nanoparticle of E1, wherein the linker capable of undergoing an intramolecular cyclization is suitable to release a therapeutic agent from the linker upon intramolecular cyclization.

E3. The therapeutic magnetic nanoparticle of E1 or E2, wherein the linker capable of undergoing an intramolecular cyclization can form a 3-8 membered heterocyclic ring upon cyclization.

E4. The therapeutic magnetic nanoparticle of E3, wherein the 3-8 membered ring comprises a group selected from an amide, carbamate, urea, carbamothioate, thioamide, thiocarbamate, thiourea and carbamodithioate.

E5. The therapeutic magnetic nanoparticle of any one of E1-E4, wherein the magnetic nanoparticle further comprises a coating.

E6. The therapeutic of magnetic nanoparticle of any one of E1-E5, wherein the protected amine is an amide, carbamate or urea.

E7. The therapeutic magnetic nanoparticle of any one of E1-E6, wherein the protected amine is an amide, urea or carbamate and the amine of the protected amine is a primary amine or secondary amine.

E8. The therapeutic magnetic nanoparticle of any one of E1-E7, wherein the protected amine is an amide, urea or carbamate and the amine of the protected amine is a primary amine or secondary amine.

E9. The magnetic nanoparticle of E5, wherein the coating is gold.

E10. The magnetic nanoparticle of E5, wherein the coating is silica.

E11. The therapeutic magnetic nanoparticle of any one of E1-E10, wherein the magnetic nanoparticle comprises iron.

E12. The therapeutic magnetic nanoparticle of any one of E1-E11, wherein the magnetic nanoparticle is an iron oxide nanoparticle coated with silica.

E13. The therapeutic magnetic nanoparticle of any one E1-E12, wherein the deprotection of the protected amine can be induced by heating the magnetic nanoparticle.

E14. The therapeutic magnetic nanoparticle of any one of E1-E12, wherein the deprotection of the protected amine occurs prior to the heating the magnetic nanoparticle.

E15. The therapeutic magnetic nanoparticle of any one of E1-E14, wherein the cyclization can be induced by heating the magnetic nanoparticle.

E16. The therapeutic magnetic nanoparticle of any one of E1-E12, wherein deprotection of the protected amine can be induced by application of an alternating electromagnetic field to the magnetic nanoparticle.

E17. The therapeutic magnetic nanoparticle of any one of E1-E12, wherein the deprotection of the protected amine occurs prior to the application of an alternating electromagnetic field to the magnetic nanoparticle.

E18. The therapeutic magnetic nanoparticle of any one of E1-E17, wherein the cyclization can be induced by application of an alternating electromagnetic field to the magnetic nanoparticle.

E19. The therapeutic magnetic nanoparticle of any one of E1-E18, wherein the linker comprises about 4-50 atoms.

E20. The therapeutic magnetic nanoparticle of any one of E1-E18, wherein the linker comprises about 4-20 atoms.

E21. The therapeutic magnetic nanoparticle of E19 or E20, wherein the atoms are independently selected from silicon, carbon, nitrogen, oxygen and sulfur.

E22. The therapeutic magnetic nanoparticle of any one of E1-E21, wherein the linker is covalently bonded to the magnetic nanoparticle through a silicon or sulfur atom.

E23. The therapeutic magnetic nanoparticle of any one of E1-E21, wherein the linker does not include a t-butoxycarbonyl (BOC) protected amine.

E24. The therapeutic magnetic nanoparticle, or a salt thereof, of any one of E1-E23, wherein each -L-D independently has the following formula I:

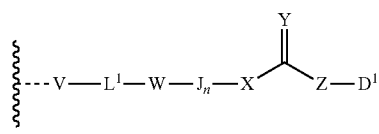

II wherein

V is $-\text{OSi(G)}_2\text{-}$, and the dashed line represents a covalent bond between the oxygen atom of $-\text{OSi(G)}_2\text{-}$ and the magnetic nanoparticle; or V is $-\text{S}-$, and the dashed line represents a covalent bond between $-\text{S}-$ and the magnetic nanoparticle;

$L^1$ is $(C_1\text{-}C_6)$alkylene, $(C_1\text{-}C_6)$heteroalkylene, $(C_2\text{-}C_6)$alkenylene, $(C_2\text{-}C_6)$alkynylene, phenylene or $(C_3\text{-}C_7)$carbocyclene, wherein $(C_1\text{-}C_6)$alkylene, $(C_1\text{-}C_6)$heteroalkylene, $(C_2\text{-}C_6)$alkenylene, $(C_2\text{-}C_6)$alkynylene, phenylene or $(C_3\text{-}C_7)$carbocyclene are optionally substituted with one or more halogen;

each J is $C(R^b)_2$ wherein one $C(R^b)_2$ of J may be replaced by $-\text{O}-$, $-\text{S}-$ or $-\text{N}(R^e)-$;

(a) W is $NR^2$, X is $CR^cR^d$, and n is an integer from 0-5; or (b) W is $NR^2$, X is O, $NR^e$ or S, and n is an integer from 1-5; or (c) W is

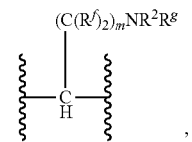

X is $CR^cR^d$, O, $NR^e$, S or absent, m is an integer from 0-5 and n is an integer from 0-5, wherein the sum of m and n is 0-5;

Y is O or S;

Z-$D^1$ is a residue of a therapeutic agent wherein Z is O, $NR^h$ or S;

each G is independently $-OR^{a1}$, $-OR^{a2}$ or $(C_1\text{-}C_6)$alkyl;

$R^{a1}$ is a covalent bond between the oxygen atom of $-OR^{a1}$ and the magnetic nanoparticle;

each $R^{a2}$ is independently H or $(C_1\text{-}C_6)$alkyl; or two $-OR^{a2}$ groups of two adjacent L-D groups together form $-\text{O}-$;

each $R^b$ is independently selected from H and $(C_1\text{-}C_3)$alkyl; or two $R^b$ groups together with the carbon to which they are attached form a $(C_3\text{-}C_7)$carbocycle;

each $R^c$ is independently selected from H and $(C_1\text{-}C_6)$alkyl, and each $R^d$ is independently selected from H and $(C_1\text{-}C_6)$alkyl; or an $R^c$ group and an $R^d$ group together with the carbon to which they are attached form a $(C_3\text{-}C_7)$carbocycle;

each $R^e$ is independently selected from H and $(C_1\text{-}C_6)$alkyl;

each $R^f$ is independently selected from H and $(C_1\text{-}C_6)$alkyl; or two $R^f$ groups together with the carbon to which they are attached form a $(C_3\text{-}C_7)$carbocycle;

$R^g$ is selected from H, $(C_1\text{-}C_6)$alkyl and $R^2$;

$R^h$ is selected from H and $(C_1\text{-}C_6)$alkyl;

each $R^2$ is independently selected from $-C(=O)R^{2a}$, $-C(=O)OR^{2b}$, $-C(=O)N(R^{2c})_2$, $C(=S)R^{2a}$, $-C(=S)OR^{2b}$ or $-C(=S)N(R^{2c})_2$;

each $R^{2a}$ is independently selected from H, $(C_1\text{-}C_{10})$alkyl, aryl or $(C_3\text{-}C_7)$carbocycle wherein $(C_1\text{-}C_{10})$alkyl, aryl or $(C_3\text{-}C_7)$carbocycle is optionally substituted with one or more halogen;

each $R^{2b}$ is independently selected from H, $(C_1\text{-}C_{10})$alkyl, aryl or $(C_3\text{-}C_7)$carbocycle wherein $(C_1\text{-}C_{10})$alkyl, aryl or $(C_3\text{-}C_7)$carbocycle is optionally substituted with one or more halogen;

each $R^{2c}$ is independently selected from H, $(C_1-C_{10})$alkyl, aryl or $(C_3-C_7)$carbocycle wherein $(C_1-C_{10})$alkyl, aryl or $(C_3-C_7)$carbocycle is optionally substituted with one or more halogen; or two $R^{2c}$ groups together with the nitrogen to which they are attached for a 3-7 membered heterocycle.

E25. The therapeutic magnetic nanoparticle of E24, wherein V is $-OSi(G)_2-$, the magnetic nanoparticle is optionally coated with silica, and the dashed line represents a covalent bond between the oxygen atom of $-OSi(G)_2-$ and the magnetic nanoparticle optionally coated with silica; or V is $-S-$, the magnetic nanoparticle is magnetic nanoparticle coated with gold, and the dashed line represents a covalent bond between $-S-$ and the magnetic nanoparticle coated with gold.

E26. The therapeutic magnetic nanoparticle of E24, wherein V is $-OSi(G)_2-$, the magnetic nanoparticle is coated with silica, and the dashed line represents a covalent bond between the oxygen atom of $-OSi(G)_2-$ and the magnetic nanoparticle coated with silica.

E27. The therapeutic magnetic nanoparticle of any one of E24-E26, wherein the magnetic nanoparticle comprises iron.

E28. The therapeutic magnetic nanoparticle of E24, wherein V is $-OSi(G)_2-$, the magnetic nanoparticle is an iron oxide nanoparticle coated with silica, and the dashed line represents a covalent bond between the oxygen atom of $-OSi(G)_2-$ and the iron oxide nanoparticle coated with silica.

E29. The therapeutic magnetic nanoparticle of E24, wherein -L-D has the following formula IIa:

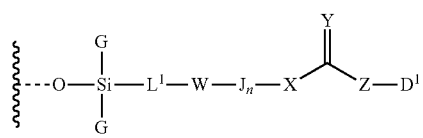

IIa wherein the dashed bond represents a covalent bond to the magnetic nanoparticle.

E30. The therapeutic magnetic nanoparticle of E24, wherein the magnetic nanoparticle is further coated with silica and wherein -L-D has the following formula IIa:

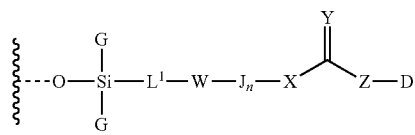

IIa wherein the dashed bond represents a covalent bond to the magnetic nanoparticle further coated with silica.

E31. The therapeutic magnetic nanoparticle of E29 or E30, wherein the magnetic nanoparticle is an iron oxide nanoparticle.

E32. The therapeutic magnetic nanoparticle of any one of E24-E31, wherein each G is $-OR^{a1}$.

E33. The therapeutic magnetic nanoparticle any one of E24-E31, wherein each G is $-OR^{a2}$, wherein each $-OR^{a2}$ together with another $-OR^{a2}$ group on an adjacent L-D group forms an $-O-$.

E34. The therapeutic magnetic nanoparticle any one of E24-E31, wherein each G is $-OR^{a1}$ or $-OR^{a2}$, wherein each $-OR^{a2}$ together with another $-OR^{a2}$ group on an adjacent L-D group form an $-O-$.

E35. The therapeutic magnetic nanoparticle of E24, wherein V is $-S-$, the magnetic nanoparticle is coated in gold, and the dashed line represents a covalent bond between $-S-$ and the magnetic nanoparticle coated in gold.

E36. The therapeutic magnetic nanoparticle of E35, wherein the dashed line represents a covalent bond between $-S-$ and a gold atom of the magnetic nanoparticle coated in gold.

E37. The therapeutic magnetic nanoparticle of E35 or E36, wherein the magnetic nanoparticle is an iron oxide nanoparticle.

E38. The therapeutic magnetic nanoparticle of E24 or any one of E35-E37, wherein -L-D has the following formula IIb:

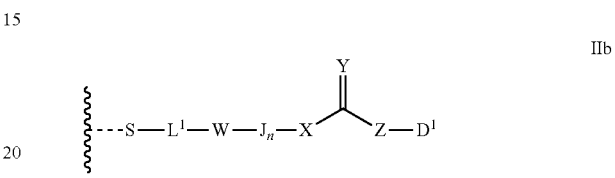

IIb wherein the dashed bonds represent a covalent bond to the magnetic nanoparticle.

E39. The therapeutic magnetic nanoparticle of any one of E24-E38, wherein $L^1$ is $(C_1-C_6)$alkylene optionally substituted with one or more halogen.

E40. The therapeutic magnetic nanoparticle of any one of E24-E38, wherein $L^1$ is $(C_1-C_6)$alkylene.

E41. The therapeutic magnetic nanoparticle of any one of E24-E38, wherein $L^1$ is $(C_2-C_4)$alkylene optionally substituted with one or more halogen.

E42. The therapeutic magnetic nanoparticle of any one of E24-E38, wherein $L^1$ is $(C_2-C_4)$alkylene.

E43. The therapeutic magnetic nanoparticle of any one of E24-E38, wherein $L^1$ is $-(CH_2)_2-$, $-(CH_2)_3-$, or $-(CH_2)_4-$.

E44. The therapeutic magnetic nanoparticle of any one of E24-E38, wherein $L^1$ is $-(CH_2)_3-$.

E45. The therapeutic magnetic nanoparticle of any one of E24-E44, wherein:
(a) W is $-NR^2-$, X is $CR^cR^d$, and n is an integer from 0-5; or
(b) W is $-NR^2-$, X is O, $NR^e$ or S, and n is an integer from 1-5.

E46. The therapeutic magnetic nanoparticle of any one of E24-E44, wherein:
(a) W is $-NR^2-$, X is $CR^cR^d$, and n is an integer from 0-5; or
(b) W is $-NR^2-$, X is O, and n is an integer from 1-5.

E47. The therapeutic magnetic nanoparticle of any one of E24-E44, wherein W is $-NR^2-$, X is $CR^cR^d$ and n is an integer from 0-5.

E48. The therapeutic magnetic nanoparticle of any one of E24-E47, wherein $R^c$ and $R^d$ are each independently selected from H and methyl.

E49. The therapeutic magnetic nanoparticle of any one of E24-E47, wherein $R^c$ and $R^d$ are each H.

E50. The therapeutic magnetic nanoparticle of any one of E24-E47, wherein $R^c$ and $R^d$ are each methyl.

E51. The therapeutic magnetic nanoparticle of any one of E24-E44, wherein W is $-NR^2-$, X is O, and n is an integer from 1-5.

E52. The therapeutic magnetic nanoparticle of any one of E24-E51, wherein n is 2, 3 or 4.

E53. The therapeutic magnetic nanoparticle of any one of E24-E52, wherein each J is $C(R^b)_2$.

E54. The therapeutic magnetic nanoparticle of any one of E24-E53, wherein each $R^b$ is independently H or methyl.
E55. The therapeutic magnetic nanoparticle of any one of E24-E54, wherein each $R^b$ is H.
E56. The therapeutic magnetic nanoparticle of any one of E24-E52, wherein $J_n$ is —(CH$_2$)$_2$—, —(CH$_2$)$_3$—, —(CH$_2$)$_4$— or —CH$_2$CH$_2$C(Me)$_2$CH$_2$—.
E57. The therapeutic magnetic nanoparticle of any one of E24-E56, wherein Y is O.
E58. The therapeutic magnetic nanoparticle of E24, wherein the portion of formula I as shown in the formula below:

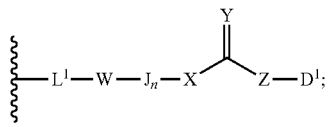

is selected from;

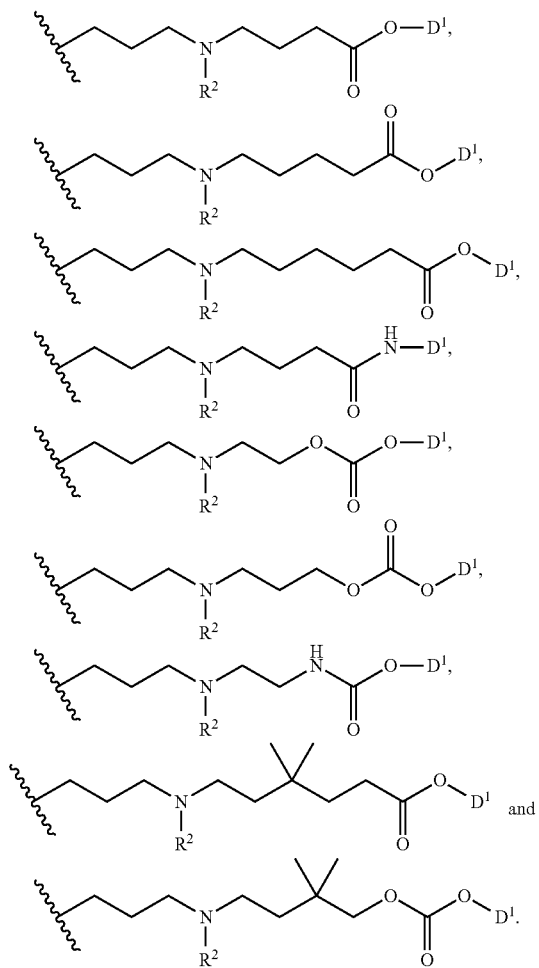

E59. The therapeutic magnetic nanoparticle of any one of E24-E58 wherein $R^2$ is not —C(=O)OC(CH$_3$)$_3$.
E60. The therapeutic magnetic nanoparticle of any one of E24-E58 wherein aryl is phenyl.

Salts

In cases where compounds are sufficiently basic or acidic, a salt of a therapeutic magnetic nanoparticle as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable salt. Alkali metal (for example, sodium, potassium or lithium) or alkaline earth metal (for example calcium) salts of carboxylic acids can also be made.

Administration

The method of administering the therapeutic magnetic nanoparticle to the desired area for treatment and the dosage may depend upon, but is not limited to, the type and location of the disease material. The size range of the nanoparticles may allow for microfiltration for sterilization. Some methods of administration include intravascular injection, intravenous injection, intraperitoneal injection, subcutaneous injection, and intramuscular injection. The nanoparticles may be formulated in an injectable format (e.g, suspension, emulsion) in a medium such as, for example, water, saline, Ringer's solution, dextrose, dimethylsulfoxide, albumin solution, and oils. The nanoparticles may also be administered to the patient through topical application via a salve or lotion, transdermally through a patch, orally ingested as a pill or capsule or suspended in a liquid or rectally inserted in suppository form. Nanoparticles may also be suspended in an aerosol or pre-aerosol formulation suitable for inhalation via the mouth or nose. Once administered to the patient, delivery of the nanoparticles to the target site may be assisted by an applied static magnetic field due to the magnetic nature of the nanoparticles. Assisted delivery may depend on the location of the targeted tissue. The nanoparticles may also be delivered to the patient using other methods. For example, the nanoparticles may be administered to the patient orally, or may be administered rectally. It is to be understood the therapeutic magnetic nanoparticles described herein may also be useful in diagnostics as well as studies in cells, tissues and animals.

The invention will now be illustrated by the following non-limiting Examples.

Example 1

General.

Reagent grade solvents were used for extraction and flash chromatography. Acetonitrile for carbamate synthesis was dried by distillation from CaH$_2$. All other commercial reagents were used as received without additional purification. The progress of reactions was checked by thin-layer chromatography (TLC, silica gel 60 Å F-254 plates). The plates were visualized first with UV illumination followed by staining using iodine, p-anisaldehyde, phosphomolybdic acid hydrate, or ninhydrin. Column chromatography was performed using silica gel (230-400 mesh). NMR spectra were obtained using a Varian/Agilent 400-MR NMR spectrometer equipped with a 5 mm z-axis gradient AutoX probe operating at the nominal $^1$H frequency of 399.66 MHz and $^{13}$C frequency of 100.49 MHz. All spectra are reported in parts per million (ppm) relative to the residual solvent peak in $^1$H NMR and the deuterated solvent peak in $^{13}$C NMR.

High-resolution mass spectra were obtained using a Finnigan LTQ-FT spectrometer (Thermo Electron Corp) in positive detection mode. Fluorescent measurements were taken on a Molecular Devices SpectraMax M5 in fluorescent mode at an excitation of 366 nm and emission wavelength of 408 nm. The fluorescent measurements were taken using a quartz semi-micro VWR Spectrosil spectrophotometer cell with a 10 mm light path. Transmission electron microscopy (TEM) was used to analyze size distribution and morphology of fabricated nanoparticles, including uniformity and thickness of silica coating. For this, ethanol-based nanoparticle dispersions were prepared and drop-casted on commercially available 300 mesh TEM support Cu grids coated with ultra thin carbon films. After ethanol evaporation, samples were transferred to and analyzed using a field emission gun FEI Tecnaci F20 transmission electron microscope operating at the accelerating voltage of 200 kV. DLS and ζ-potential measurements were taken using a Brookhaven Instruments 90Plus Particle Size Analyzer. All measurements were taken using aqueous colloids of the nanoparticles in Millipore water. The alternating magnetic field (AMF) was generated with a Ambrell EasyHeat L1 set at 501.6 amps and 204 kHz using a 5-turn coil.

Synthesis of Linker S4.

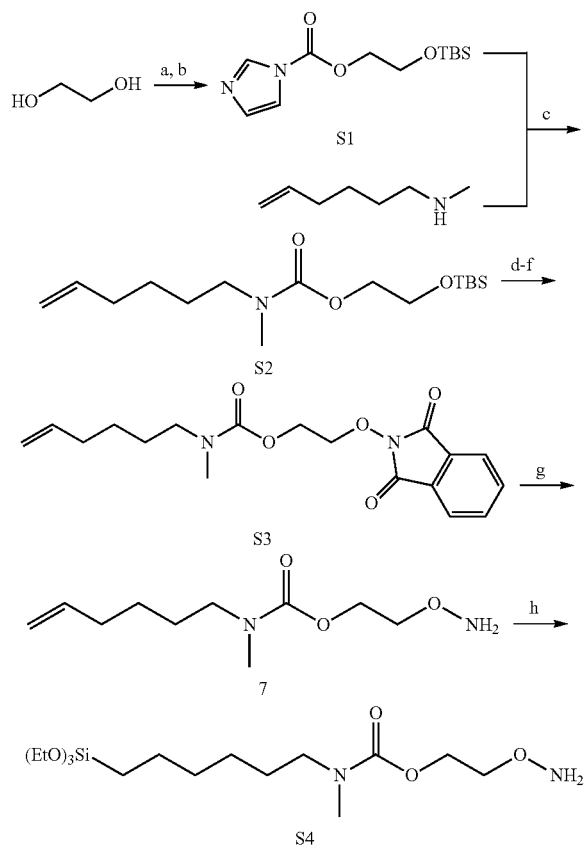

a) TBSCl, Et$_3$N, CH$_2$Cl$_2$, 0° C.;
b) 1,1'-carbonyldiimidazole, (i-Pr)$_2$Net, CH$_2$Cl$_2$, 0° C.;
c) DBU, MeCN, rt, 79% over 3 steps;
d) TBAF, THF, 0° C.;
e) MsCl, Et$_3$N, CH$_2$Cl$_2$, 0° C.;
f) N-hydroxyphthalimide, K$_2$CO$_3$, DMSO, 75° C., 71% over 3 steps;
g) N$_2$H$_4$·H$_2$O, CH$_2$Cl$_2$, 0° C., 96%,
h) (EtO)$_3$SiH, cat. PtO$_2$, 90° C., 48 h.

A solution of TBSCl (2.34 g, 15.5 mmol) in dry CH$_2$Cl$_2$ (20 mL) was added dropwise over 1 h to a solution of ethylene glycol (8 mL, 143 mmol) and Et$_3$N (2.80 mL, 19.9 mmol) in dry CH$_2$Cl$_2$ (25 mL) at 0° C. and was stirred overnight. The solvent was removed in vacuo and the remaining oil was extracted with hexanes (4×) and the combined extractions were washed twice with sat. NH$_4$Cl, once with brine and was dried over Na$_2$SO$_4$, filtered and concentrated in vacuo to afford the mono-TBS protected diol 2-((tert-butyldimethylsilyl)oxy)ethan-1-ol (2.52 g, 92%) as a colorless oil and was used without further purification. R$_f$ 0.59 (1:3, EtOAc:hexanes).

1,1'-Carbonyldiimidazole (3.47 g, 21.4 mmol) was added to a solution of the mono-TBS protected diol (2.52 g, 14.3 mmol) and N,N-diisopropylethylamine (3.70 mL, 21.4 mmol) in dry CH$_2$Cl$_2$ (48 mL) at 0° C. and was stirred for 6 h. The reaction was washed twice with water and the combined aqueous phases were extracted once with CH$_2$Cl$_2$. The combined organic layers were then washed twice with sat. NH$_4$Cl, once with brine and were dried over Na$_2$SO$_4$, filtered and concentrated in vacuo to afford crude S1 as a colorless oil and was used without further purification. R$_f$ 0.36 (1:3, EtOAc:hexanes); $^1$H NMR (400 MHz, CDCl$_3$) δ 0.06 (s, 6H), 0.88, (s, 9H), 3.93 (t, J=4.8 Hz, 2H), 4.71 (t, t=4.8 Hz, 2H), 7.06 (s, 1H), 7.42 (s, 1H), 8.13 (s, 1H); $^{13}$C NMR (100 MHz, CDCl$_3$) δ −5.2, 18.4, 25.9, 61.0, 69.4, 117.3, 130.9, 137.3, 149.0.

The carbamate was synthesized as described in the literature (Heller, S. T.; et al., Angew. Chem., Int. Ed. 2012, 51, 8304-8308). DBU (2.13 mL, 14.3 mmol) was added to a solution of crude S1 (14.3 mmol) in dry MeCN (70 mL) and was stirred for 10 min, then N-methyl-1-aminohex-5-ene (1.60 g, 14.3 mmol) was added and the reaction was stirred overnight. The reaction was then washed twice with sat. NH$_4$Cl and the combined aqueous layers were extracted three times with EtOAc. The combined organic phases were washed with brine, dried over Na$_2$SO$_4$, filtered and concentrated in vacuo. The crude material was purified by column chromatography (SiO$_2$, 1:3, EtOAc:hexanes) to give a colorless oil S2 (3.56 g, 79% over 3 steps). R$_f$ 0.40 (1:3, EtOAc:hexanes); $^1$H NMR (400 MHz, CDCl$_3$) δ 0.06 (s, 6H), 0.89 (s, 9H), 1.38 (quin, J=7.4 Hz, 2H), 1.52, (quin, J=7.6 Hz, 2H), 2.07 (q, J=7.2 Hz, 2H), 2.88 (s, 3H), 3.25 (t, J=7.2 Hz, 2H), 3.80 (t, J=5.0 Hz, 2H), 4.13 (t, J=5.0 Hz, 2H), 4.93-5.02 (m, 2H), 5.73-5.84 (m, 1H); $^{13}$C NMR (100 MHz, CDCl$_3$) δ −5.1, 18.5, 26.1, 27.6, 33.6, 34.1, 49.0, 62.0, 66.8, 114.9, 138.7, 156.7; FT-ICR-MS calcd for C$_{16}$H$_{34}$NO$_3$Si$^+$ [M+H]$^+$ m/z 316.2302, found 316.2307.

TBAF (1 M in THF, 10.6 mL, 10.6 mmol) was added dropwise to a solution of S2 (2.58 g, 8.17 mmol) in dry THF (16 mL) at 0° C. and was stirred overnight. The reaction solution was washed twice with sat. NaHCO$_3$ and the combined aqueous layers were extracted three times with Et$_2$O. The combined organic phases were washed with brine, dried over Na$_2$SO$_4$, filtered and concentrated in vacuo to afford crude 2-hydroxyethyl N-(hex-5-en-1-yl)-N-methylcarbamate as a yellow oil and was used without further purification. R$_f$ 0.12 (1:3, EtOAc:hexanes); $^1$H NMR (400 MHz, CDCl$_3$) δ 1.40 (quin, J=7.8 Hz, 2H), 1.55 (quin, J=7.6 Hz, 2H), 2.08 (q, J=6.8 Hz, 2H), 2.90 (s, 3H), 3.26 (t, J=7.2 Hz, 2H), 3.78-3.82 (q, J=4.4 Hz, 2H), 4.23 (t, J=4.4 Hz, 2H), 4.94-5.02 (m, 2H), 5.74-5.84 (m, 1H); $^{13}$C NMR (100 MHz, CDCl$_3$) δ 25.9, 27.4, 33.6, 34.7, 48.9, 62.6, 67.7, 115.0, 138.6, 157.4.

Methanesulfonyl chloride (728 µL, 9.40 mmol) was added dropwise to a solution of the crude alcohol (8.17 mmol) and triethylamine (1.72 mL, 12.3 mmol) in CH$_2$Cl$_2$ (27 mL) at 0° C. and stirred overnight. The reaction was then washed twice with sat. NH₄Cl and the combined aqueous layers were extracted twice with CH₂Cl₂. The combined organic phases were washed with brine, dried over Na₂SO₄, filtered and concentrated in vacuo to give crude 2-(methanesulfonyloxy)ethyl N-(hex-5-en-yl)-N-methylcarbamate as a light yellow oil (2.15 g). $R_f$ 0.36 (major product) & 0.68 (1:1, EtOAc:hexanes); ¹H NMR (400 MHz, CDCl₃, $R_f$ 0.36) δ 1.37 (quin, J=7.6 Hz, 2H), 1.54 (quin, =7.6 Hz, 2H), 2.07 (q, J=7.2 Hz, 2H), 2.89 (s, 3H), 3.01 (s, 3H), 3.26 (t, J=7.2 Hz, 2H), 4.32-4.34 (m, 2H), 4.39-4.41 (m, 2H), 4.93-5.02 (m, 2H), 5.74-5.81 (m, 1H); ¹³C NMR (100 MHz, CDCl₃, $R_f$ 0.36) δ 26.1, 27.0, 33.5, 34.1, 37.9, 49.2, 62.8, 68.1, 114.9, 138.6, 155.9.

K₂CO₃ (1.17 g, 8.47 mmol) was added to a solution of the combined mesyl carbamate products ($R_f$ 0.36 & 0.68) (2.15 g, 7.70 mmol) in DMSO (26 mL), followed by the addition of N-hydroxyphthalimide (2.39 g, 14.6 mmol) and the dark red solution was heated at 75° C. overnight. The yellow solution was cooled to rt and slowly quenched with water and extracted four times with EtOAc. The combined organic phase was washed three times with water, once with brine, dried over Na₂SO₄, filtered and concentrated in vacuo. The crude material was purified by column chromatography (SiO₂, 1:1, EtOAc:hexanes) to give a yellow oil S3 (2.02 g, 71% over 3 steps). $R_f$ 0.55 (1:1, EtOAc:hexanes); ¹H NMR (400 MHz, CDCl₃) δ 1.35 (quin, J=7.6 Hz, 2H), 1.52 (quin, J=7.6 Hz, 2H), 2.05 (q, J=7.2 Hz, 2H), 2.85 (br s, 3H), 3.24 (t, J=7.2 Hz, 2H), 4.41 (s, 4H), 4.91-5.00 (m, 2H), 5.72-5.82 (m, 1H), 7.72-7.75 (m, 2H), 7.80-7.82 (m, 2H); ¹³C NMR (100 MHz, CDCl₃) δ 26.1, 27.2, 33.5, 34.6, 49.1, 62.8, 76.7, 114.8, 123.7, 129.2, 134.7, 138.7, 156.1, 163.5; FT-ICR-MS calcd for $C_{18}H_{23}N_2O_5^+$ [M+H]⁺ m/z 347.1601, found 347.1606.

Hydrazine monohydrate (34 μL, 0.70 mmol) was added to a solution of S3 (258 mg, 0.74 mmol) in CH₂Cl₂ (4 mL) at 0° C. and was stirred for 1 h. The solids were then filtered off and the filter cake was washed with ample CH₂Cl₂. The filtrate was then concentrated in vacuo to afford 7 (154 mg, 96%) as a colorless oil without further purification. $R_f$ 0.24 (1:1, EtOAc:hexanes); ¹H NMR (400 MHz, CDCl₃) δ 1.36 (quin, J=7.6 Hz, 2H), 1.52 (quin, J=7.6 Hz, 2H), 2.05 (q, J=7.2 Hz, 2H), 2.86 (s, 3H), 3.24 (t, J=7.2 Hz, 2H), 3.80 (t, J=3.6 Hz, 2H), 4.26 (t, J=4.4 Hz, 2H), 4.91-5.00 (m, 2H), 5.42 (br s, 2H), 5.71-5.82 (m, 1H); ¹³C NMR (100 MHz, CDCl₃) δ 26.0, 27.3, 33.5, 34.6, 48.8, 62.9, 74.3, 114.8, 138.7, 156.7; FT-ICR-MS calcd for $C_{10}H_{21}N_2O_3^+$ [M+H]⁺ m/z 217.1547, found 217.1548.

Following a related literature example (Sabourault, N.; et al., *Org. Lett.* 2002, 4, 2117-2119), catalytic PtO₂ and triethoxysilane (131 μL, 0.71 mmol) was added to 7 (153 mg, 0.71 mmol) in a pressure tube. The tube was flushed ti N₂, sealed and heated to 90° C. for 48 h. The reaction solution was cooled to rt and filtered through Celite into a flask flushed with N₂ and the filter cake was washed with ample dry CH₂Cl₂. The filtrate was concentrated in vacuo to afford crude S4 as a light brown oil which was used without further characterization or purification due to its sensitivity to moisture.

Synthesis of Linker S6.

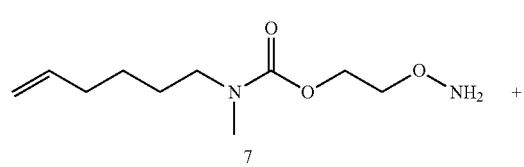

7

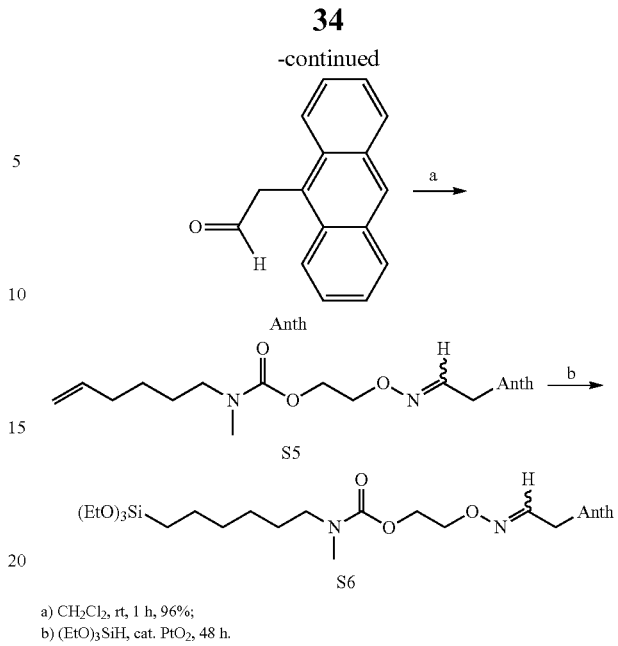

a) CH₂Cl₂, rt, 1 h, 96%;
b) (EtO)₃SiH, cat. PtO₂, 48 h.

2-(Anthracen-9-yl)acetaldehyde (175 mg, 0.79 mmol; (Jiang, H.; et al., *Angew. Chem. Int. Ed.* 2012, 51, 10271-10274)) was added to a solution of 7 (156 mg, 0.72 mmol) in CH₂Cl₂ (4 mL) and stirred for 1 h. The reaction solution was concentrated in vacuo. The crude material was purified by column chromatography (SiO₂, 0:1 to 3:17, EtOAc:CH₂Cl₂ gradient) to give a yellow oil S5 (291 mg, 96%). $R_f$ 0.55 (1:19, EtOAc:CH₂Cl₂); ¹H NMR (400 MHz, CDCl₃) δ 0.78 (br s, 0.25H), 0.87 (br s, 0.25H), 1.26 (br s, 1.44H), 1.35-1.41 (m, 2H), 1.55-1.63 (m, 2H), 1.92-2.07 (m, 2H), 2.78 (br s, 0.68H), 2.95 (s, 1.91H), 3.14 (br s, 0.46H), 3.22 (br s, 0.46H). 3.30-3.34 (m, 1.33H), 4.26 (dd, J=16.8, 5.4 Hz, 1.78H), 4.49-4.52 (m, 3.48H), 4.68 (d, J=4.4 Hz, 1.31H), 4.88-5.02 (m, 2H), 5.69-5.79 (m, 1H), 6.74 (t, J=5.0 Hz, 0.60H), 7.47-7.57 (m, 4.48H), 8.01-8.05 (m, 2H), 8.19 (d, J=8.4 Hz, 1H), 8.30 (d, J=8.8 Hz, 1H), 8.43 (s, 1H); ¹³C NMR (100 MHz, CDCl₃) δ 25.3, 26.6, 28.7, 33.6, 34.8, 48.8, 64.1, 72.9, 114.9, 124.2, 125.3, 126.3, 127.1, 128.7, 129.4, 130.3, 131.7, 138.7, 150.3, 156.6; FT-ICR-MS calcd for $C_{26}H_{31}N_2O_3^+$ [M+H]⁺ m/z 419.2329, found 419.2333.

Linker S6 was synthesized using the procedure described for the synthesis of linker S4.

Synthesis of Linker Precursor 12.3.

2-(Anthracen-9-yl)ethyl pent-4-enoate

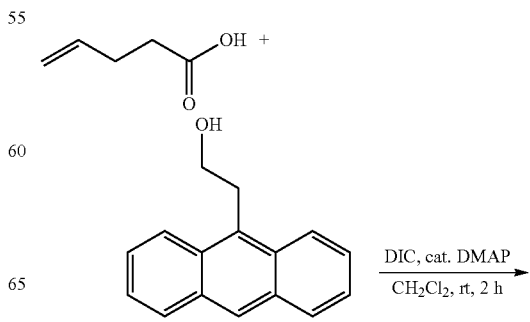

DIC, cat. DMAP
CH₂Cl₂, rt, 2 h

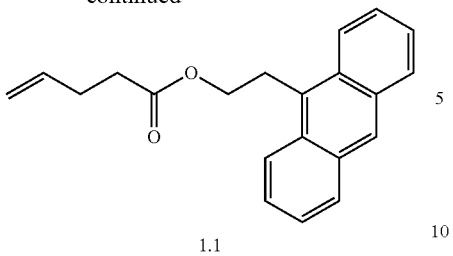

1.1

4-Pentenoic acid (159 μL, 1.56 mmol) and 2-(anthracen-9-yl)ethanol (281 mg, 1.26 mmol) were dissolved in dry CH$_2$Cl$_2$ (15 mL) with stirring. DIC (305 μL, 1.95 mmol) was added to the reaction solution followed by cat. DMAP. After 2 h, the white solids were filtered out and the filter cake was washed with CH$_2$Cl$_2$. The filtrate was condensed in vacuo and the crude material was purified by column chromatography (SiO$_2$, 1:1 hexanes:CH$_2$Cl$_2$) to give 12.1 (359 mg, 93%) as a yellow oil. R$_f$ 0.36 (1:1 hexanes:CH$_2$Cl$_2$); $^1$H NMR (400 MHz, CDCl$_3$) δ 2.35-2.46 (m, 4H), 3.99 (t, J=8.0 Hz, 2H), 4.50 (t, J=7.8 Hz, 2H), 5.00-5.08 (m, 2H), 5.79-5.88 (m, 1H), 7.46-7.50 (m, 2H), 7.54-7.58 (m, 2H), 8.02 (d, J=8.4 Hz, 2H), 8.38 (d, J=8.8 Hz, 2H), 8.40 (s, 1H); $^{13}$C NMR (100 MHz, CDCl$_3$) δ 27.5, 29.0, 33.8, 64.3, 115.7, 124.3, 125.1, 126.2, 127.0, 129.2, 129.4, 130.5, 131.7, 136.8, 173.4.

Allyl 1H-imidazole-1-carboxylate

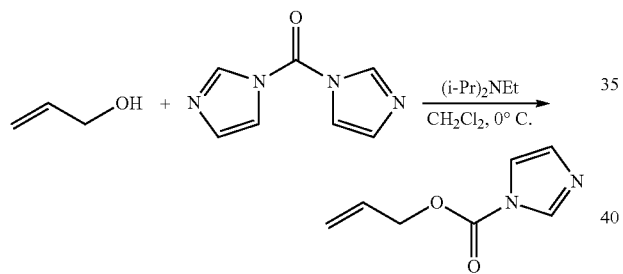

N,N-Diisopropylethylamine (5.37 mL, 30.8 mmol) was added to a solution of allyl alcohol (1.21 g, 20.8 mmol) in dry CH$_2$Cl$_2$ (69 mL). The solution was cooled to 0° C. and 1,1'-carbonyldiimidazole (5.07 g, 31.2 mmol) was added and the reaction was stirred overnight. The reaction was washed with water (2×40 mL), brine (40 mL) and dried over Na$_2$SO$_4$, filtered and concentrated in vacuo. The crude material was purified by column chromatography (SiO$_2$, EtOAc) to give the acyl imidazole intermediate (2.24 g, 71%) as a light yellow oil. R$_f$ 0.51 (EtOAc); $^1$H NMR (400 MHz, CDCl$_3$) δ 4.87 (d, J=5.6 Hz, 2H), 5.37 (d, J=10.0 Hz, 1H), 5.44 (d, J=16.8 Hz, 1H), 5.95-6.03 (m, 1H), 7.05 (s, 1H), 7.42 (s, 1H), 8.13 (s, 1H); $^{13}$C NMR (100 MHz, CDCl$_3$) δ 68.8, 117.3, 120.6, 130.6, 130.9, 137.3, 148.6.

Allyl (2-(anthracen-9-yl)ethyl) carbonate

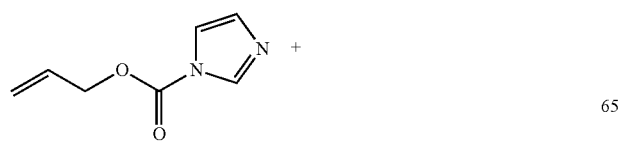

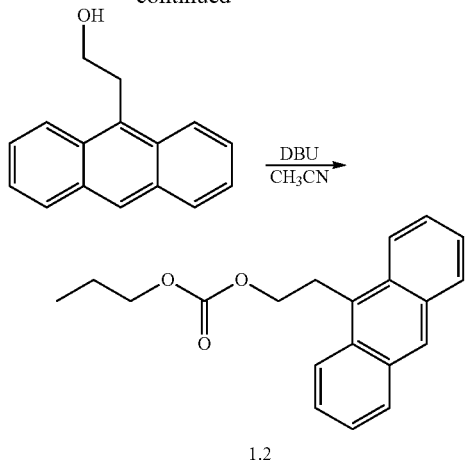

1,8-Diazabicyclo[5.4.0]undec-7-ene (1.68 mL, 11.2 mmol) was added to a solution of the acyl imidazole intermediate (1.71 g, 11.2 mmol) in dry CH$_3$CN (56 mL). The reaction solution was stirred for 10 minutes before adding 2-(anthracen-9-yl)ethanol (2.50 g, 11.2 mmol). The reaction was stirred overnight before quenching with sat. NH$_4$Cl (40 mL). The aqueous phase was extracted with EtOAc (2×40 mL) and the combined organic phases were washed with brine, dried over Na$_2$SO$_4$, filtered and concentrated in vacuo. The crude material was purified by column chromatography (SiO$_2$, 3:1, CH$_2$Cl$_2$:hexanes) to give 1.2 (2.33 g, 68%) as yellow crystals. R$_f$ 0.63 (3:1, CH$_2$Cl$_2$:hexanes); $^1$H NMR (400 MHz, CDCl$_3$) δ 4.06 (t, J=8.0 Hz, 2H), 4.52 (t, J=8.4 Hz, 2H), 4.69 (d, J=5.6 Hz, 2H), 5.31 (dd, J=10.8, 1.8 Hz, 1H), 5.40 (dd, J=17.6, 1.2 Hz, 1H), 5.93-6.03 (m, 1H), 7.47-7.50 (m, 2H), 7.55-7.59 (m, 2H), 8.02 (d J=8.4 Hz, 2H), 8.35 (d, J=8.8 Hz, 2H), 8.40 (s, 1H); $^{13}$C NMR (100 MHz, CDCl$_3$) δ 27.6, 67.4, 68.7, 119.1, 124.1, 125.2, 126.4, 127.2, 128.3, 129.5, 130.5, 131.7, 131.8, 155.3.

2-(Anthracen-9-yl)ethyl 1H-imidazole-1-carboxylate

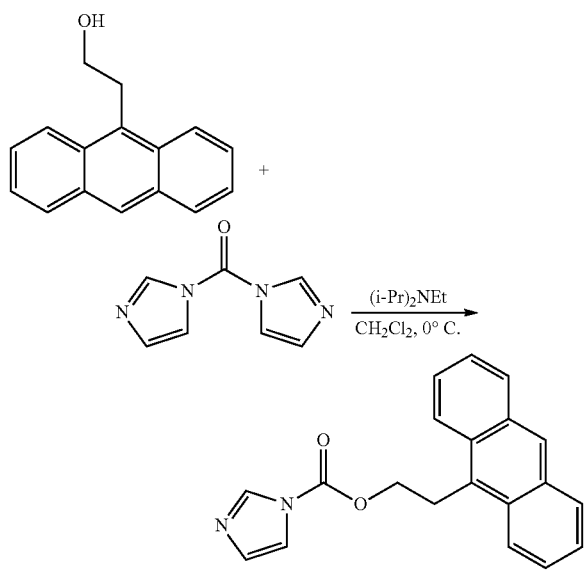

N,N-Diisopropylethylamine (408 μL, 2.34 mmol) was added to a solution of 2-(anthracen-9-yl)ethanol (346 mg, 1.55 mmol) in dry $CH_2Cl_2$ (8 mL), the solution was cooled to 0° C. and 1,1'-carbonyldiimidazole (380 mg, 2.34 mmol) was added. After stirring overnight, the reaction solution was washed with water (2×5 mL), brine, dried over $Na_2SO_4$, filtered and concentrated in vacuo. The crude material was purified by column chromatography ($SiO_2$, $CH_2Cl_2$ to 3:2, EtOAc:$CH_2Cl_2$ gradient) to give the acyl imidazole intermediate (436 mg, 89%) as a pale yellow solid. $R_f$ 0.23 (1:19, EtOAc:$CH_2Cl_2$); $^1H$ NMR (400 MHz, $CDCl_3$) δ 4.16 (t, J=7.4 Hz, 2H), 4.80 (t, J=7.6 Hz, 2H), 7.02 (s, 1H), 7.31 (s, 1H), 7.50 (t, J=7.6 Hz, 2H), 7.58 (t, J=7.4 Hz, 2H), 8.00 (s, 1H), 8.04 (d, J=8.0 Hz, 2H), 8.33 (d, J=8.8 Hz, 2H), 8.44 (s, 1H); $^{13}C$ NMR (100 MHz, $CDCl_3$) δ 27.0, 68.0, 117.3, 123.8, 125.3, 126.6, 127.5, 127.9, 129.7, 130.5, 130.8, 131.7, 137.3, 149.0.

2-(Anthracen-9-yl)ethyl allylcarbamate

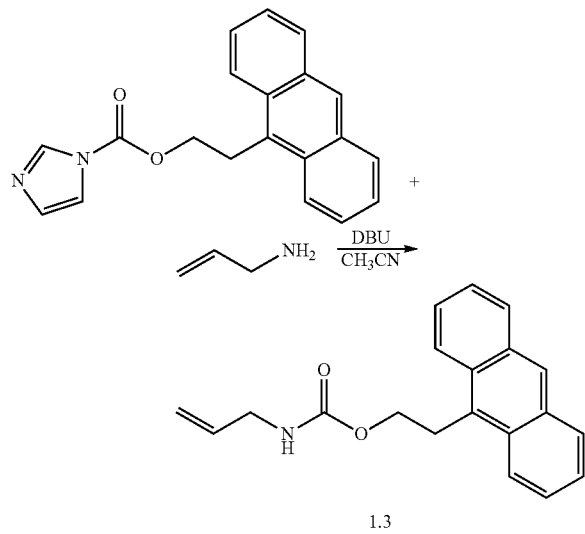

1,8-Diazabicyclo[5.4.0]undec-7-ene (206 μL, 1.38 mmol) was added to a solution of the acyl imidazole intermediate (436 mg, 1.38 mmol) in dry $CH_3CN$ (7 mL). The reaction solution was stirred for 10 minutes before adding allylamine (114 μL, 1.51 mmol). The reaction was stirred overnight before quenching with sat. $NH_4Cl$ (40 mL). The aqueous phase was extracted with EtOAc (2×5 mL) and the combined organic phases were washed with brine, dried over $Na_2SO_4$, filtered and concentrated in vacuo. The crude material was purified by column chromatography ($SiO_2$, $CH_2Cl_2$ to 2:3, EtOAc:$CH_2Cl_2$ gradient) to give 1.3 (356 mg, 85%) as pale yellow crystals. $R_f$ 0.72 (1:19, EtOAc:$CH_2Cl_2$); $^1H$ NMR (400 MHz, $CDCl_3$) δ 3.85 (br s, 2H), 4.00 (t, J=7.8 Hz, 2H), 4.47 (t, J=7.6 Hz, 2H), 4.74 (br s, 1H), 5.13-5.22 (m, 2H), 5.84-5.90 (m, 1H), 7.45-7.49 (m, 2H), 7.53-7.56 (m, 2H), 8.01 (d, J=8.4 Hz, 2H), 8.36 (d, J=8.8 Hz, 2H), 8.39 (s, 1H); $^{13}C$ NMR (100 MHz, $CDCl_3$) δ 28.1, 43.7, 64.9, 116.3, 124.4, 125.1, 126.2, 126.9, 129.4, 130.6, 131.7, 134.7, 156.7.

Synthesis of $SiO_2@Fe_3O_4$ NPs.

Figure 1:
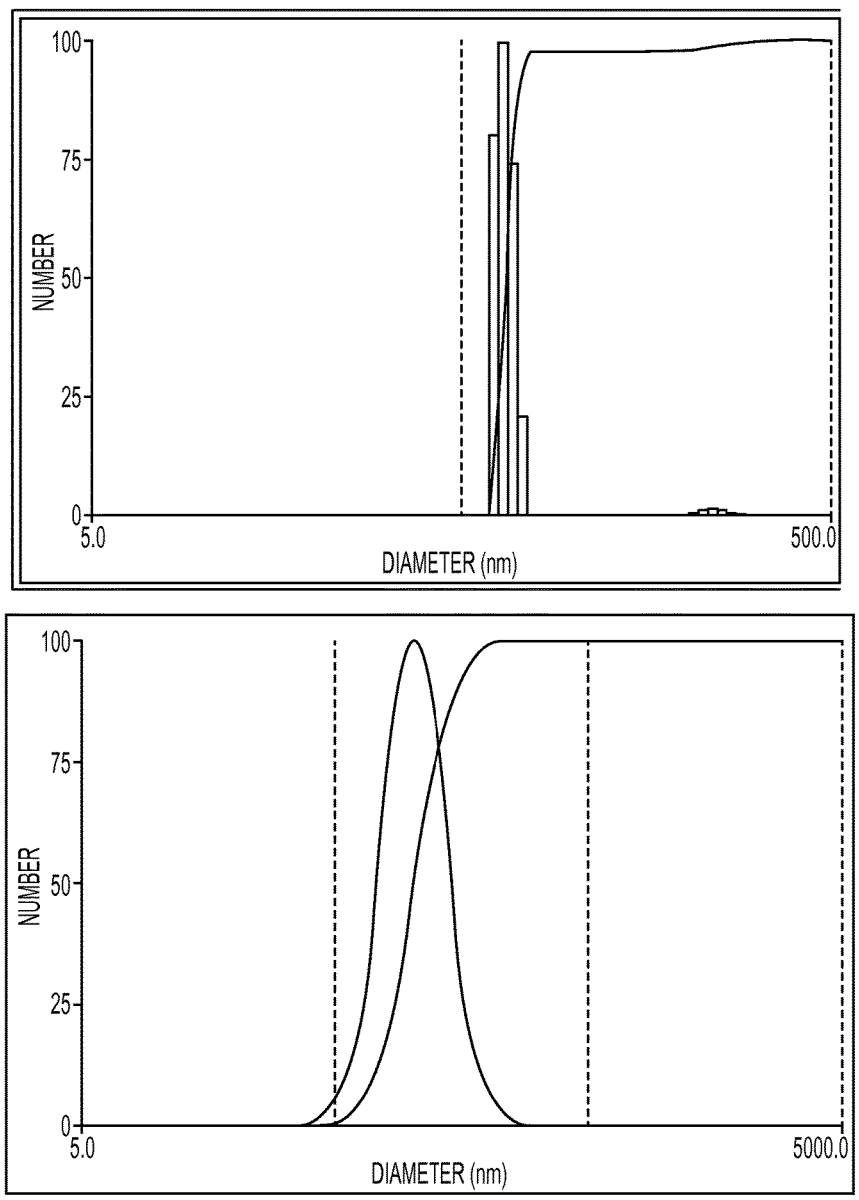
FIG. 1 illustrates the DLS of $SiO_2$@$Fe_3O_4$ NPs in Millipore water.
Figure 2:
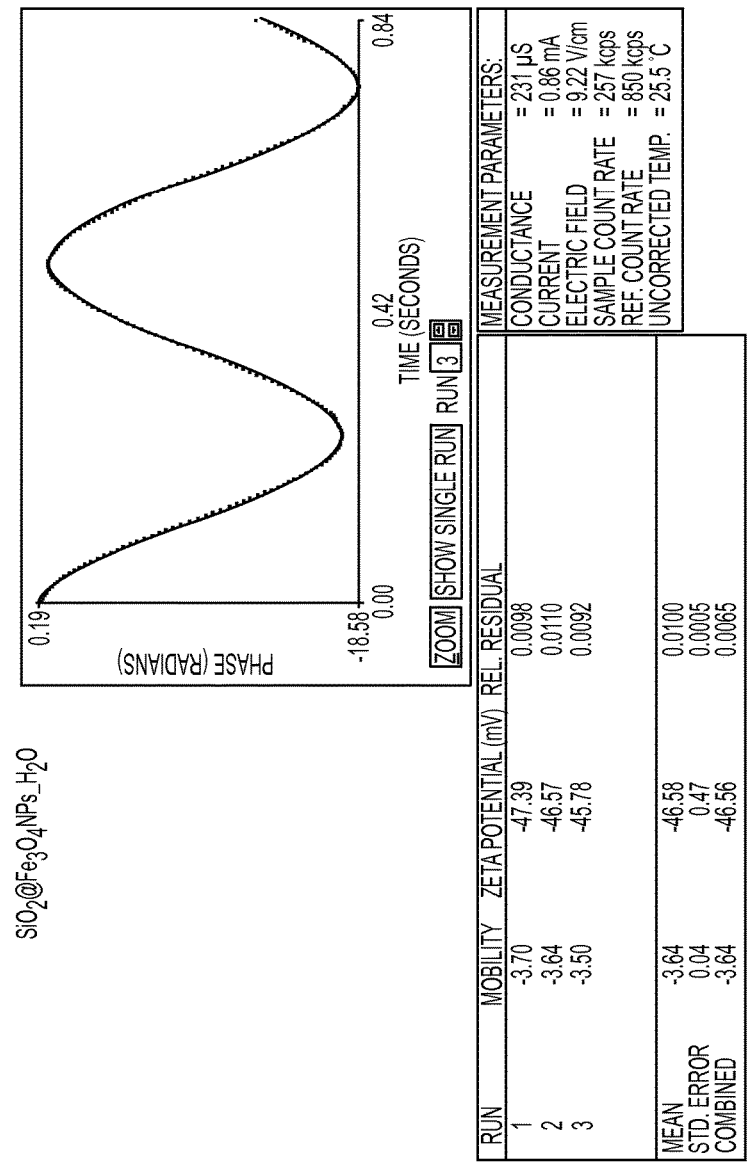
FIG. 2 illustrates the ζ-Potential (−46.58±0.47 mV) and mobility (−3.64±0.04) of $SiO_2$@$Fe_3O_4$ NPs in Millipore water.
Figure 3:
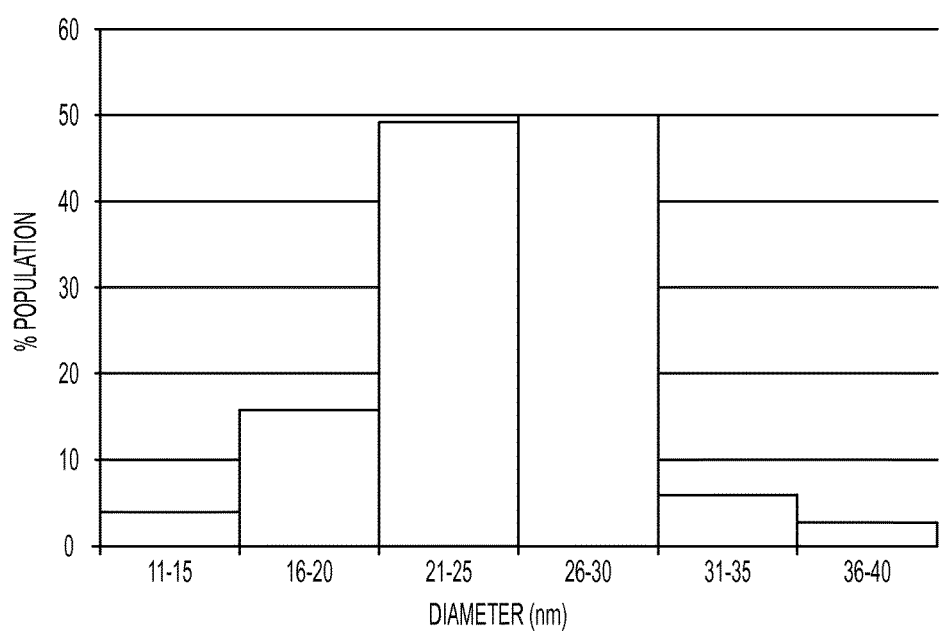
FIG. 3 illustrates the size distribution (24.1±0.6 nm) of $SiO_2$@$Fe_3O_4$ NPs as determined by TEM measurements.

The $Fe_3O_4$ NPs were coated with a thin silica shell using a modified procedure described in the literature (Pinho, S.; et al., *ACS Nano* 2010, 4, 5339-5349). EMG 304 ferrofluid (1 mL, 233 mg NPs, 8.55×10$^{16}$ NPs) was added to Millipore water (98 mL) and was then added to a solution of EtOH (312 mL) and $NH_4OH$ (6.2 mL, 28-30%) with rapid mechanical stirring. Tetraethyl orthosilicate (TEOS) (2.13 mL) was then added to the colloidal suspension and was stirred for 12 h. An aliquot was removed to allow for characterization. The NPs were magnetically separated and the remaining colloidal supernatant was centrifuged at 13,200 RPM for 20 min. The NPs were then washed 5× with EtOH with magnetic separation and centrifugation after each wash. The excess EtOH was then removed by rotary evaporation and the NPs were dried under vacuum for 3 h. The resulting $SiO_2@Fe_3O_4$ NPs were characterized by IR, TGA, DLS (FIG. 1), ζ-potential (FIG. 2), SQUID (FIG. 4) and TEM (FIG. 3).

SQUID Measurements.

Figure 4:
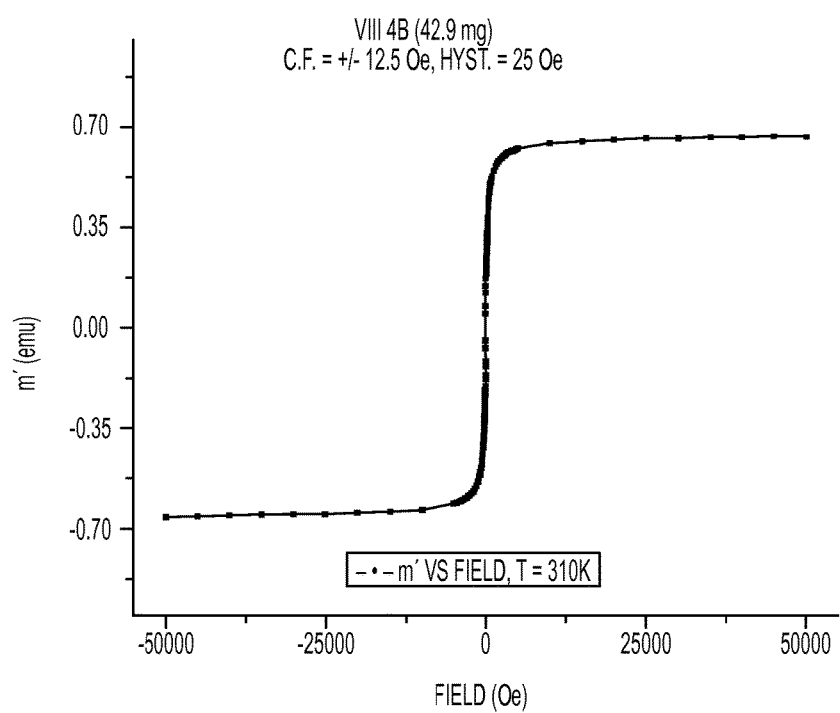
FIG. 4 illustrates SQUID measurement showing the superparamagnetism of $SiO_2$@$Fe_3O_4$ NPs.

The magnetic properties of the MNP were measured using a Quantum Design MPMS-5S superconducting quantum interference device (SQUID) magnetometer (in the temperature range from 2 to 400 K). The samples were loaded in a gel capsule and secured inside a standard drinking straw with small holes punched in both the straw and capsule for equalization of pressure and temperature. M(H) data was taken by starting the sample at saturation, 5 T, and then cycling to −5 T and back to 5 T in different step ranges to see the details of the hysteresis. The data was taken using DC Magnetization as to disturb the MNP as little as possible during the measurement (FIG. 4).

Synthesis of $AO@SiO_2@Fe_3O_4$ and $FL@SiO_2@Fe_3O_4$ NPs.

Figure 5:
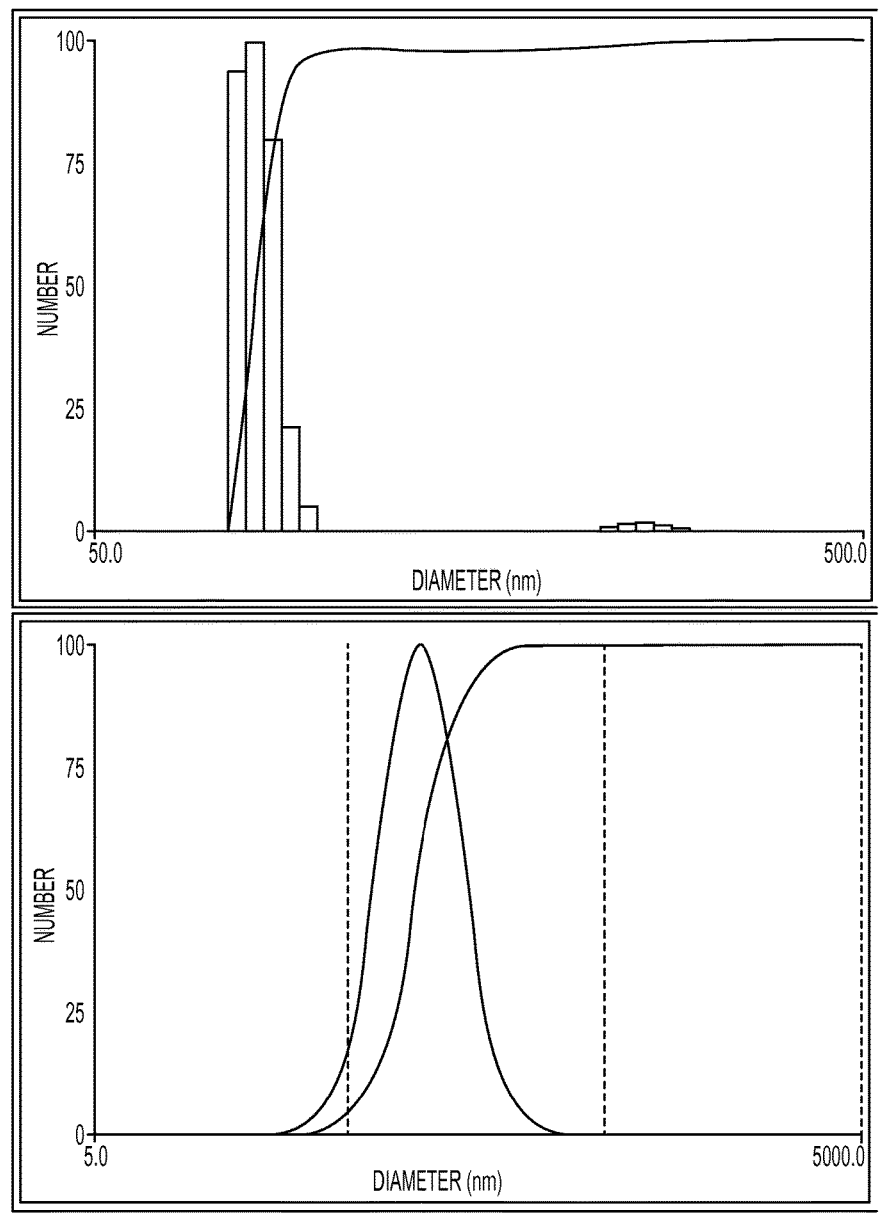
FIG. 5 illustrates the DLS of AO@$SiO_2$@$Fe_3O_4$ NPs in Millipore water.
Figure 6:
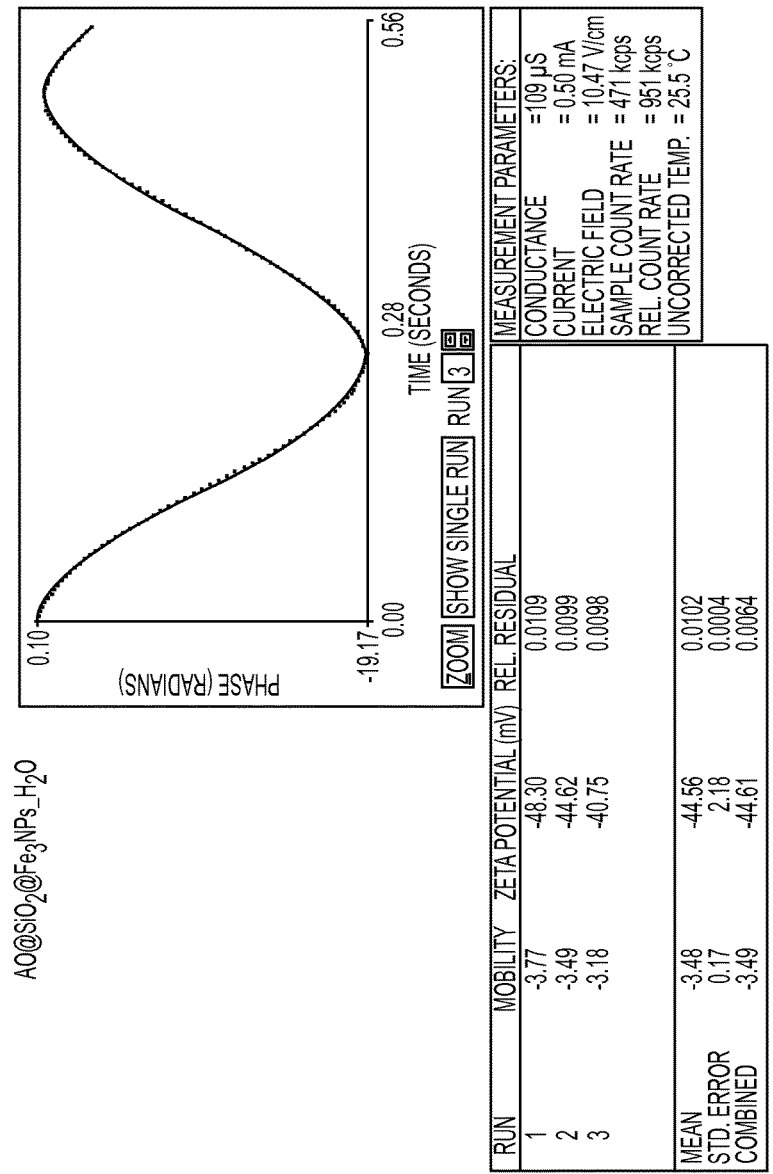
FIG. 6 illustrates the ζ-Potential (−44.56±2.18 mV) and mobility (−3.48±0.17) of AO@$SiO_2$@$Fe_3O_4$ NPs in Millipore water.
Figure 7:
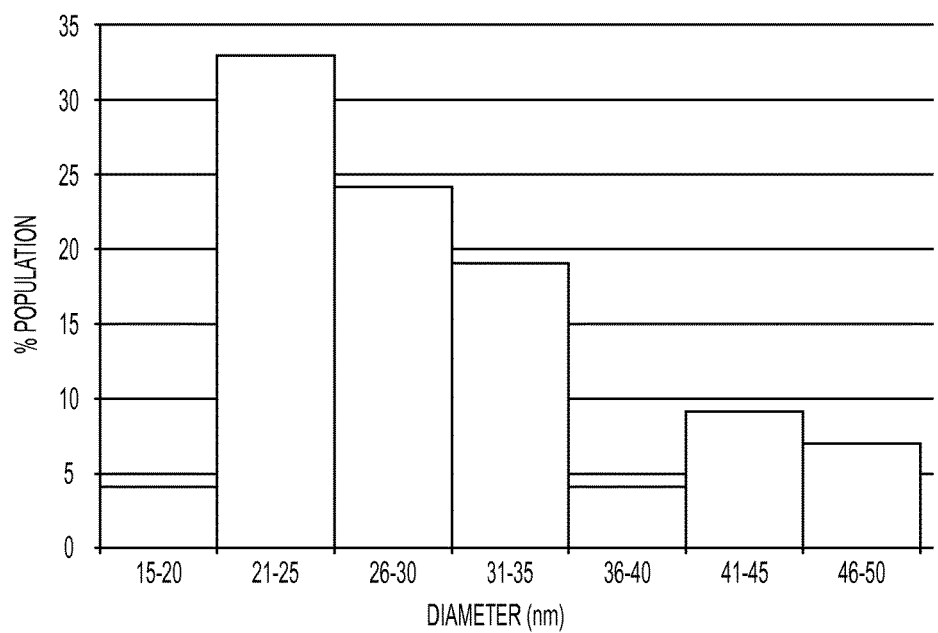
FIG. 7 illustrates the Size distribution (30.4±0.8 nm) of AO@$SiO_2$@$Fe_3O_4$ NPs as determined by TEM measurements.
Figure 8A:
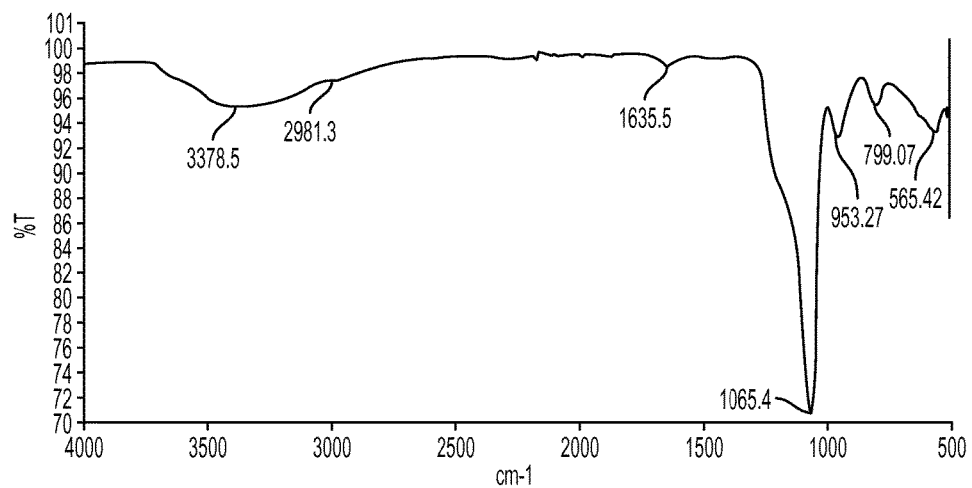
FIGS. 8A and 8B illustrates the FT-IR of $SiO_2$@$Fe_3O_4$NPs.
Figure 8B:
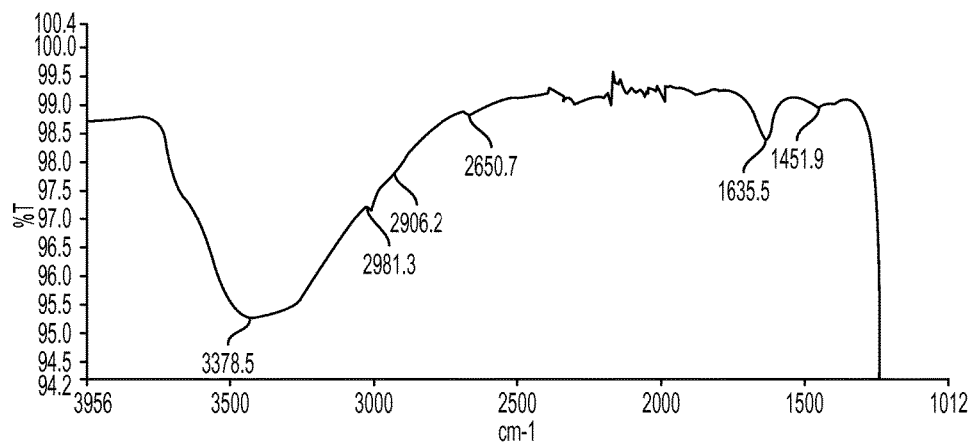
Figure 9A:
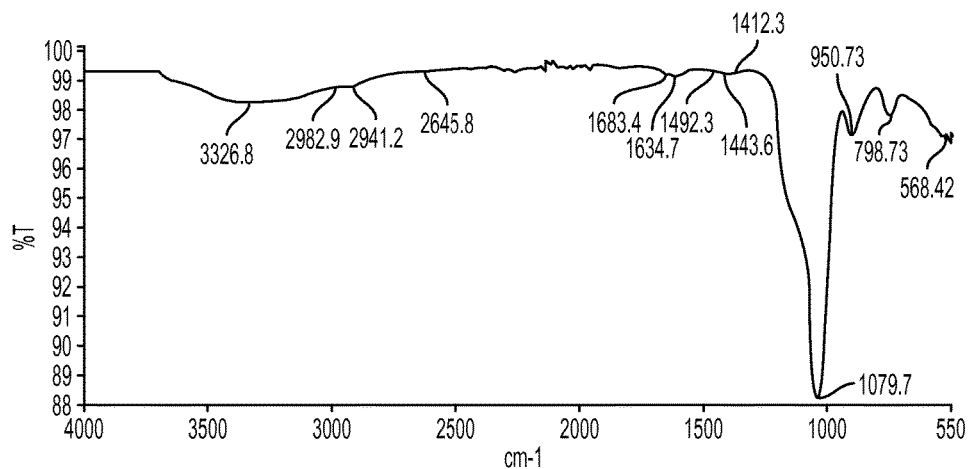
FIGS. 9A and 9B illustrates the FT-IR of AO@$SiO_2$@$Fe_3O_4$NPs (8).
Figure 9B:
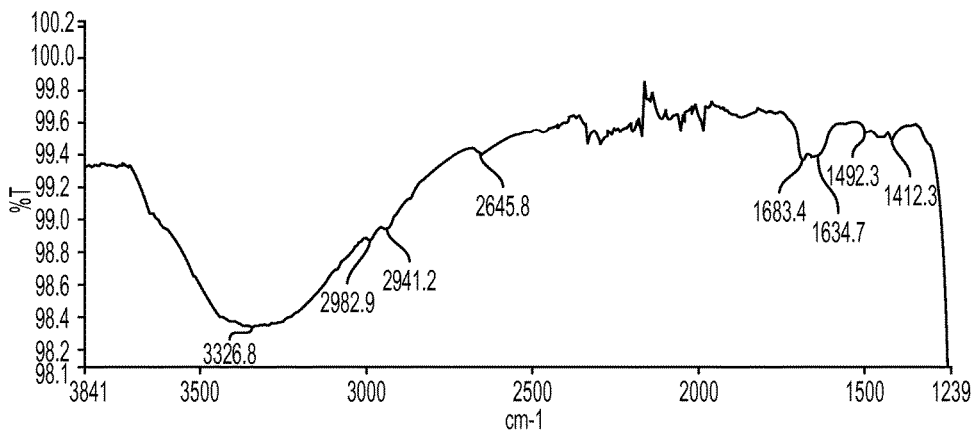

The suspension of $SiO_2@Fe_3O_4$ NPs was placed under mild vacuum and heated to 60° C. for 8 h. This process was used to remove the catalytic ammonia thus increasing the chances of obtaining a thin organic monolayer on the surface of the NPs. The removal of the ammonia decreased the pH of the solution from 11.7 to 8.8. Then, EtOH (5 mL) was added to S4 or S6 (1.454 mmol) and the solution was added to the NP suspension with rapid mechanical stirring. The mixture was stirred for 20 h. The majority of the $AO@SiO_2@Fe_3O_4$ or $FL@SiO_2@Fe_3O_4$ NPs were then magnetically separated and the remaining colloidal supernatant was centrifuged at 13,200 RPM for 20 min. The NPs were then washed 5× with EtOH with magnetic separation and centrifugation after each wash. The excess EtOH was then removed by rotary evaporation and the NPs were dried under vacuum for 3 h. The resulting NPs were characterized by IR, TGA, DLS (FIG. 5), ζ-potential (FIG. 6) and TEM (FIG. 7).

Assay of Percent FL Released.

To determine the percent of 11 released from $FL@SiO_2@Fe_3O_4$ NPs, the residual amount of S6 remaining on the $FL@SiO_2@Fe_3O_4$ NPs post AMF exposure was determined as follows. After recording the fluorescence intensity of the last (eighth) AMF pulse, the NPs were magnetically separated and the AMF supernatant was removed. The isolated NPs then were washed 5× with MeCN followed by magnetic separation to remove any non-covalently bound 11. To the washed NPs was added 1 mL of 5% HF in EtOH. The suspension was stirred until all NPs had dissolved resulting in a light yellow solution. The acidic solution was added to a separatory funnel and then basified using sat. aq. $NaHCO_3$. The basic solution was extracted 3× with $Et_2O$ and the combined extracts were concentrated by rotary evaporation and dried under vacuum. The resulting residue was dissolved in a 2:1 mixture of PBS:MeCN (0.75 mL) at pH 7.4 and the fluorescence was measured. This measured fluorescence intensity was then added to the total fluorescence intensity measured in the supernatant after the final AMF pulse, and the combined intensity was set to 100%. The results from all three experiments were normalized by dividing the fluorescent intensity by the milligrams of FL@SiO$_2$@Fe$_3$O$_4$ NPs used for the experiment.

FT-IR Spectra.

FT-IR measurements were taken on a Perkin-Elmer Spectrum 100 FT-IR with a universal ATR attachment. All IR spectra underwent ATR correction using Perkin-Elmer software (FIGS. 8A, 8B, 9A and 9B).

TGA.

Figure 10:
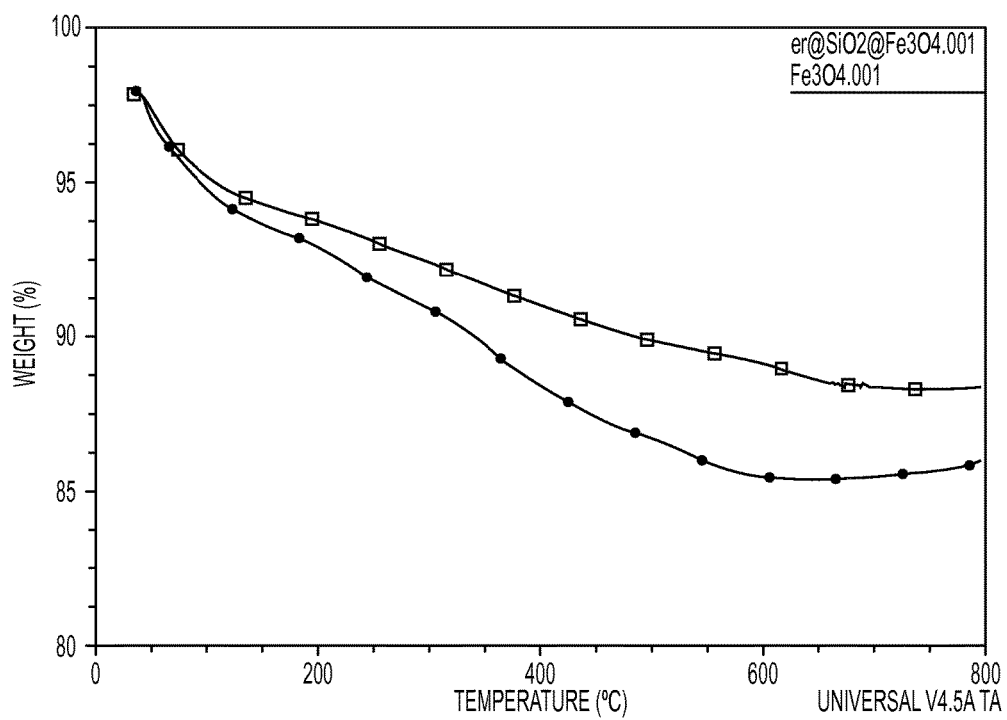
FIG. 10 illustrates the TGA of $SiO_2$@$Fe_3O_4$ NPs (□) and 8 AO@ $SiO_2$@$Fe_3O_4$ NPs (•).

TGA measurements were made on a TA Instruments Hi-Res TGA 2950 Thermogravimetric Analyzer using a Pt basket and maintaining a flow of N$_2$ gas through the oven (FIG. 10). Each TGA experiment was run from 35° C. to 800° C. at a ramp rate of 20° C./min.

AMF Heating of Bulk Solution.

Figure 11:
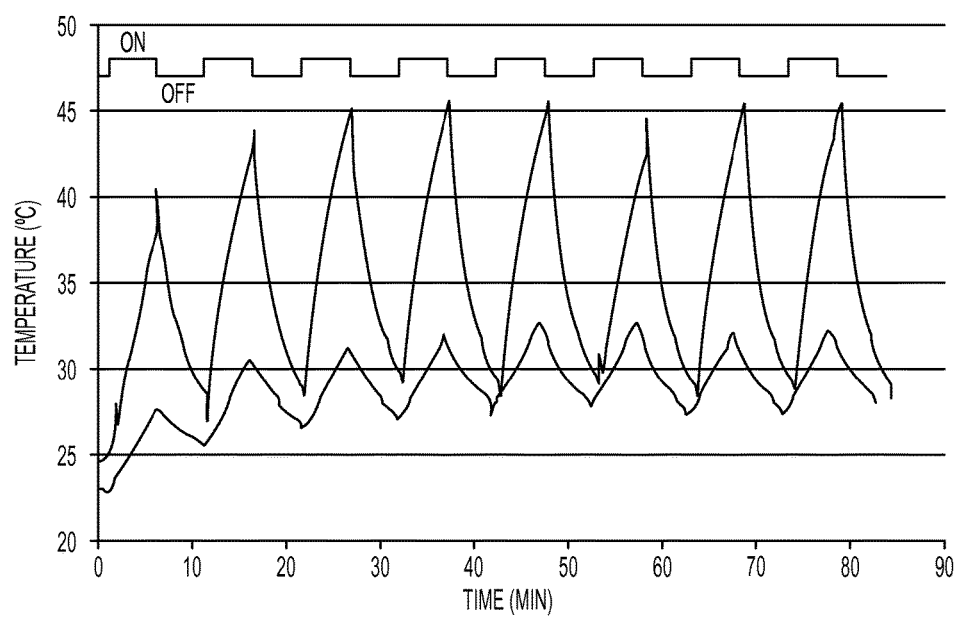
FIG. 11 illustrates the AMF-induced heating/cooling of 2:1 PBS:acetonitrile (bottom line), $SiO_2$@$Fe_3O_4$ NPs (middle line), AMF 5 min on/5 min off sequence (top line).

Temperature measurements were taken with a Neoptix Nomad fitted with a fiber optic temperature sensor. All data was recorded using Neoptix NeoLink software. AMF conditions were set to 501.6 amps and a frequency of 204 kHz. Each AMF pulse lasted for 5 min followed by 5 min of without an AMF for a combined total of 40 min of AMF exposure (FIG. 11). All samples were started at room temperature and were allowed to cool at room temperature; all heating was induced using only an AMF. The control was 0.75 mL of 2:1 PBS:acetonitrile without SiO$_2$@Fe$_3$O$_4$ NPs, which gave a ΔT of 4.8±0.1° C. with a 5 min AMF pulse. The ΔT of a 5 min AMF pulse with 7.0 mg of SiO$_2$@Fe$_3$O$_4$ NPs in 0.75 mL 2:1 PBS:acetonitrile was 16.4±0.3° C.

MALDI-TOF Results.

Figure 12:
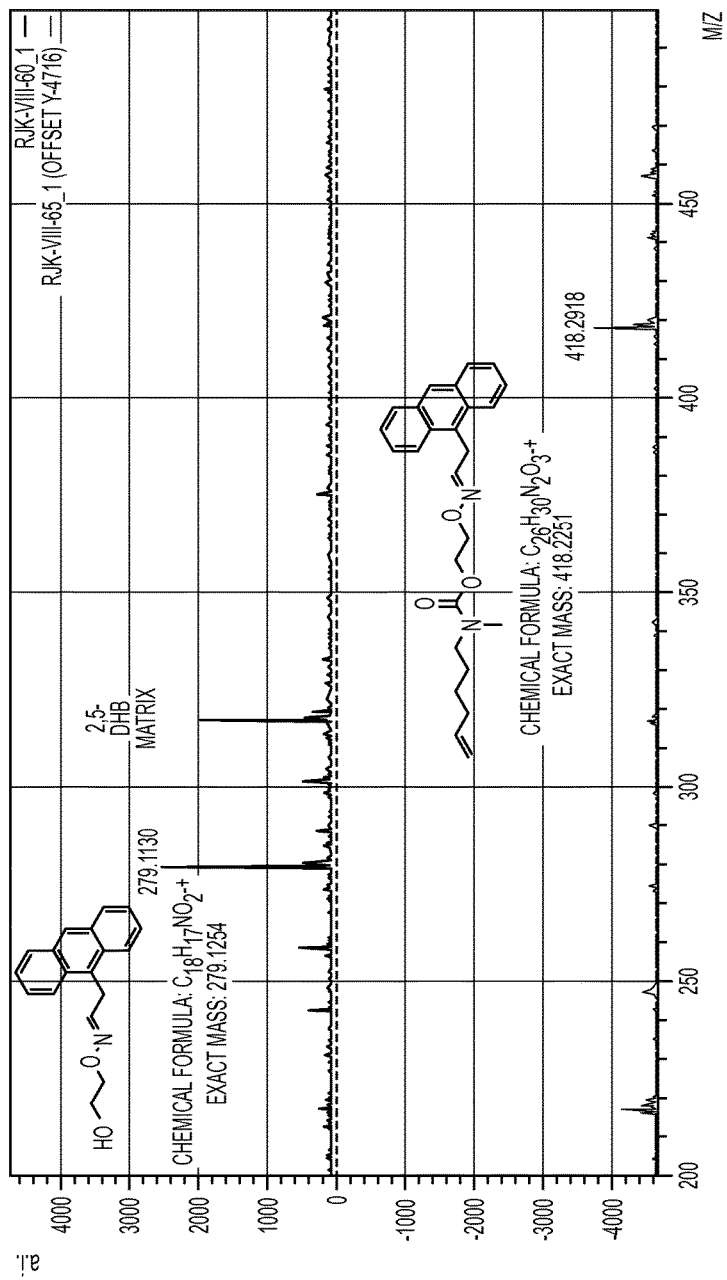
FIG. 12 shows the MALDI-TOF of the radical carbocation (Macha, S. F.; et al., *J. Am. Soc. Mass Spectrom.* 2000, 11, 731-737) of S5 (bottom) and 11 (top) after AMF-induced hydrolysis and release from FL@$SiO_2$@$Fe_3O_4$ NPs (9).

MALDI-TOF analysis was done on a Voyager DE-Pro MALDI-TOF instrument (PE Biosystems). Spectra were acquired in positive reflectron mode and calibration was achieved by using known peaks from the 2,5-dihydroxybenzoic acid (2,5-DHB) matrix (FIG. 12). Data was analyzed with mMASS data analysis software.

Results and Discussion.

Figure 13:
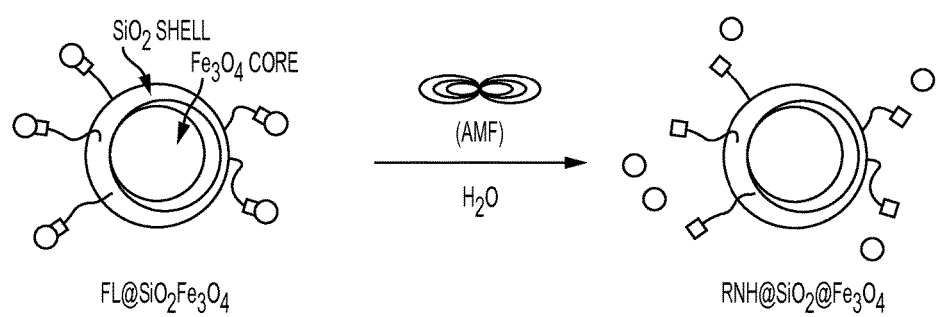
FIG. 13 illustrates the AMF-triggered hydrolysis of pendant functionality (FL=anthracene fluorophore (•); carbamate moiety (darker shaded box in nanoparticle on left); terminal amine residue (lighter shaded box in nanoparticle on right)).

It has been discovered that AMF can cause the rapid hydrolysis of an otherwise robust chemical linkage, an N,N-disubstituted carbamate. As depicted graphically in FIG. 13, a core-shell Fe$_3$O$_4$—SiO$_2$ NP construct fitted with short chains that terminate with a carbamate-bound fluorophore was engineered. Pulsed AMF irradiation of an aqueous, 37° C. suspension of these NPs buffered at pH 7.4 results in carbamate hydrolysis to release the fluorophore at a rate considerably faster than the limited release observed without irradiation.

Scheme 1 illustrates covalently tethering a drug to shell-core SiO$_2$—Fe$_3$O$_4$ NPs via carbonate functionality using a linking chain that contains a secondary amine, such as shown by NP assembly 1. Application of an AMF to raise the surrounding temperature resulted in an intramolecular Cyclization via reaction of the amine with the carbonate moiety, as in WO2014/124329. The resultant formation of oxazolidinone 3 would be accompanied by release of the bound substrate R—OH.

Scheme 1. AMF-mediated intramolecular cyclization results in release or ROH.

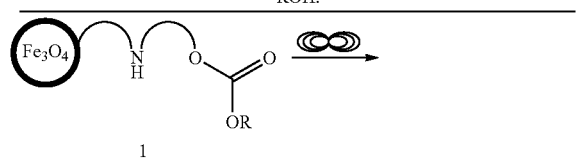

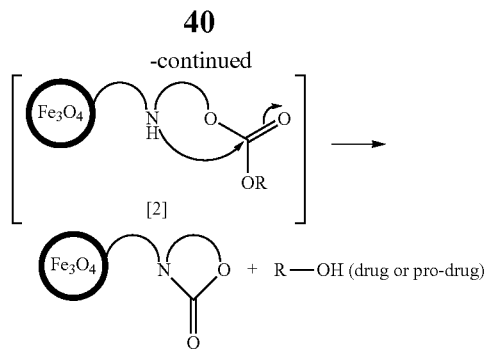

Studies were conducted to evaluate the thermal responsiveness of a panel of homologous ester and carbonate linkers (Knipp, R. J.; Estrada, R.; Sethu, P.; Nantz, M. H. Tetrahedron 2014, 70, 3422-3429). One study involved carbonate 4 (Scheme 2).

Scheme 2. Synthesis of NP-carbonate linker conjugates with anthracenyl fluorophore (Ar = 9-anthracenyl).

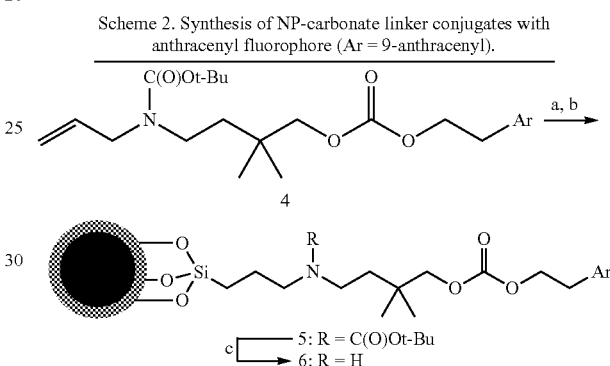

Conditions:
a. (EtO)$_3$SiH, cat. PtO$_2$, 90° C.;
b. SiO$_2$@Fe$_3$O$_4$, EtOH, H$_2$O;
c. i. CF$_3$CO$_2$H:CH$_2$Cl$_2$, 1:1, 0° C., 1 h; ii. Et$_3$N:1:1, rt.

Figure 14A:
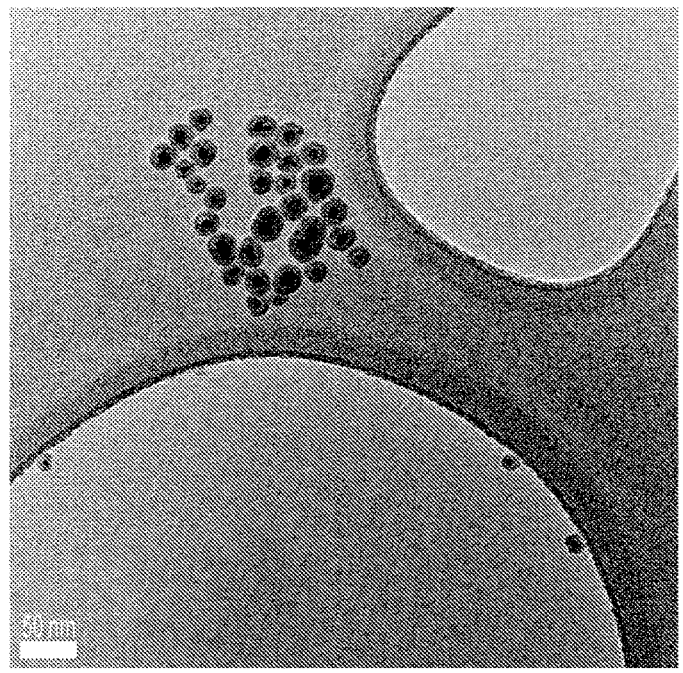
FIGS. 14A and 14B illustrate TEM images of (14A) $SiO_2$@$Fe_3O_4$ NPs used for synthesis of 5 (Scheme 1) and 8 (Scheme 2) and (14B) aminooxy-coated AO@$SiO_2$@$Fe_3O_4$NPs (8).

A shell-core SiO$_2$@Fe$_3$O$_4$ NPs was prepared using a modified version of the Stober process as reported (Pinho, S.; et al., ACS Nano 2010, 4, 5339-5349). Commercial Fe$_3$O$_4$ NPs (EMG 304, FerroTec) with a reported average diameter of 10 nm were silylated to form monodispersed superparamagnetic SiO$_2$@Fe$_3$O$_4$ NPs with a particle size distribution of 24±6 nm and a silica shell thickness of 6-7 nm, as determined by transmission electron microscopy (FIG. 14A). Residual ammonia from the shell application procedure was removed prior to NP functionalization by placing the ethanol/water suspension of SiO$_2$@Fe$_3$O$_4$ NPs under mild vacuum and then heating at 60° C. for 8 h. Removal of the ammonia in this way decreased the pH of the suspension from 11.7 to 8.8. The resultant SiO$_2$@Fe$_3$O$_4$ NPs then were functionalized by adding an ethanolic solution of the triethoxysilane-derived linker obtained from PtO$_2$-catalyzed (Sabourault, N. et al., Org. Lett. 2002, 4, 2117-2119) hydrosilylation of alkene 4 (Knipp, R. J.; Estrada, R.; Sethu, P.; Nantz, M. H. Tetrahedron 2014, 70, 3422-3429) with (EtO)$_3$SiH to obtain Boc-protected NPs 5 (Scheme 2). The Boc group was cleaved by treatment with trifluoroacetic acid followed by neutralization with triethylamine to unmask the nucleophilic amine needed for the AMF-induced intramolecular cyclization. NPs 6 then were screened in a pulsed AMF experiment for release of the bound anthracene fluorophore.

Figure 15:
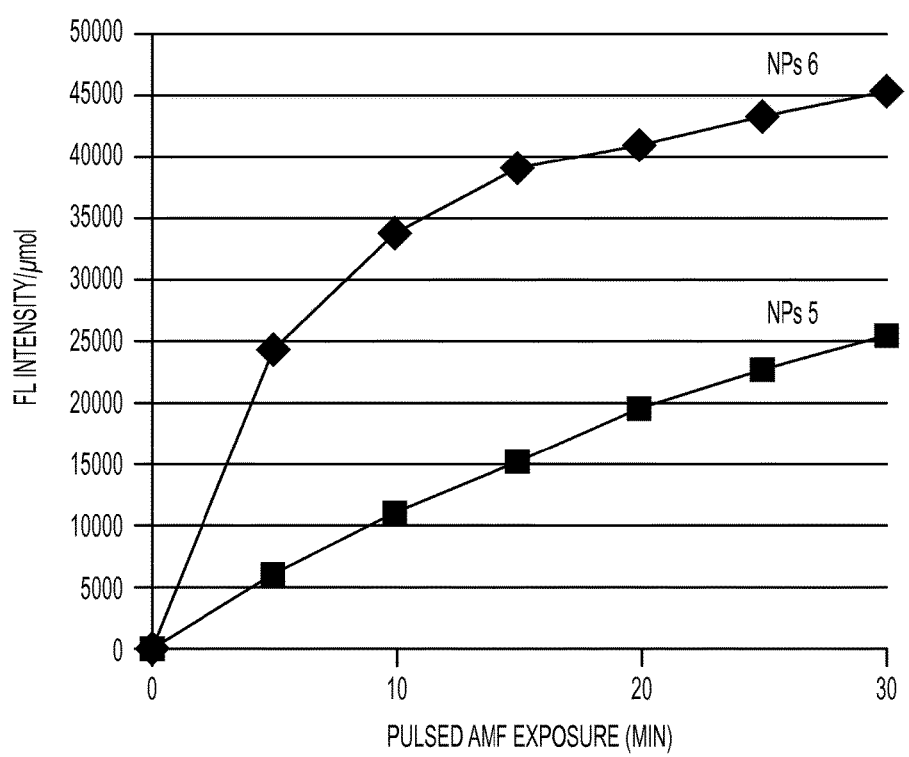
FIG. 15 illustrates AMF-induced release of anthracene fluorophore from NPs 5 and 6. NPs (7 mg) suspended in 2:1

A suspension of the free-amine NPs 6 in a 2:1 mixture of PBS:acetonitrile (pH adjusted to 7.4) at room temperature was sequentially pulsed with an AMF for six 5-minute bursts with a delay time of 5 minutes between pulses. Magnetic-assisted sedimentation of the NPs allowed facile measurement of supernatant fluorescence, imparted by the fluorophore released on intramolecular cyclization, at the end of each pulse (FIG. 15). The data clearly show an AMF-induced release of fluorophore, confirmed by MALDI-TOF analysis as 2-(anthracen-9-yl)ethan-1-ol, presumably as a consequence of amine attack onto the proximal carbonate moiety. To test the proposed mechanism of substrate release, the Boc-protected NPs 5, which would be incapable of undergoing the postulated intramolecular cyclization, under identical conditions was examined. Fluorophore release from 5 also occurred in response to AMF irradiation, albeit at a rate slower than the free amine formulation (FIG. 15). This result suggests carbonate cleavage by a route other than oxazolidinone formation, and points toward enhanced hydrolysis as a function of the energy deposited by AMF irradiation. Significant, rapid heating within nanometers of an iron oxide NP surface is known to occur on application of an AMF (Riedinger, A.; et al., T. Nano Lett. 2013, 13, 2399-2406). Another possible mechanism for release of the fluorophore would involve removal of the Boc group followed by intramolecular cyclization. Pulsed AMF irradiation at this concentration of NPs did not significantly increase the temperature of the suspension, as confirmed by measurements taken using a fiber optic temperature sensor (+16.4±0.3° C. from start of AMF pulse to end of AMF pulse, +4° C. from start of first pulse to start of sixth pulse). On examination of the stability of NPs 5 under the same conditions but without AMF irradiation, it was noted the gradual release of 2-(anthracen-9-yl)ethan-1-ol over an hour at 37° C. to ~50% of the cumulative level achieved by the six 5-minute bursts of AMF irradiation. This finding is noteworthy because dialkylcarbonates are stable to such mild conditions and generally require highly basic conditions for their hydrolysis (e.g., 5M NaOH, MeOH, rt, 3d (Zhang, J.; et al., Macromolecules 2013, 46, 2535-2543). Exposure of carbonate 4 (Scheme 1) to $SiO_2@Fe_3O_4$ NPs in 2:1 phosphate buffer solution (PBS):acetonitrile at 37° C. resulted in no reaction, even after 24 h exposure. It is possible that the close proximity and the tethered relationship of the carbonate linkage in 5 to the iron oxide core and silica shell enhance, possibly through Lewis acid or hydrogen bonding interactions, respectively, the rate of hydrolysis of an otherwise robust chemical linkage.

Based on this study additional NPs for an AMF-responsive delivery system that resists hydrolysis at 37° C. and pH 7.4 were examined. One study modified the linker by removing the nucleophilic element and used an N-methyl carbamate linkage to replace the carbonate moiety. Even unsubstituted carbamates are extremely resistant to hydrolysis and typically require treatment with base at elevated temperatures for cleavage (e.g., KOH, diglyme, 200° C.) (Melamed, J. Y.; et al., Bioorg. Med. Chem. Lett. 2010, 20, 4700-4703). A strategy for convenient attachment of substrate to the simplified carbamate-linked NPs, namely oximation was used. Click chemistry reaction of NP-bound aminooxy groups with aldehydes to form oxime ethers can be used as a convenient means for surface functionalization (Biswas, S.; et al., Biomaterials 2011, 32, 2683-2688; Beaudette, T. T et al., J. Am. Chem. Soc. 2009, 131, 10360-10361; Kolb, H. C.; et al., Angew. Chem. Int. Ed. 2001, 40, 2004-2021). Importantly, any newly formed oxime ether linkage would be sufficiently resistant to hydrolysis and thus decrease the risk of a non-AMF induced release (Kalia, J.; Raines, R. Angew. Chem. Int. Ed. 2008, 47, 7523-7526). The combination of these structural alterations is embodied by NP assembly 9 (Scheme 3) in which the anthracene fluorophore probe has been introduced by oximation using (9-anthracenyl)-acetaldehyde (10) (Jiang, H.; et al., Angew. Chem. Int. Ed. 2012, 51, 10271-10274).

Scheme 3. Synthesis and reaction of aminooxy-coated $SiO_2@Fe_3O_4$ NPs (Ar = 9-anthracenyl).

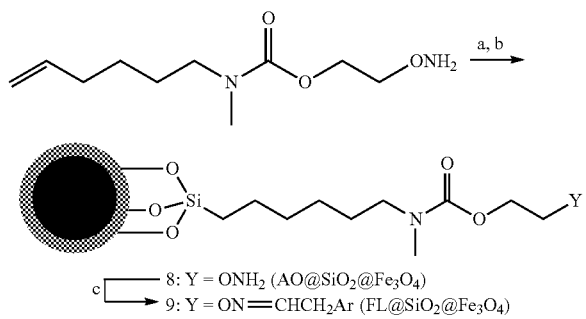

Conditions:
a. $(ETO)_3SiH$, cat. $PtO_2$, 90° C., 48 h;
b. $SiO_2@Fe_3O_4$, EtOH, $H_2O$;
c. (9-anthracenyl)-$CH_2CHO$ (10), EtOH, $H_2O$, rt, 8 h.

Figure 14B:
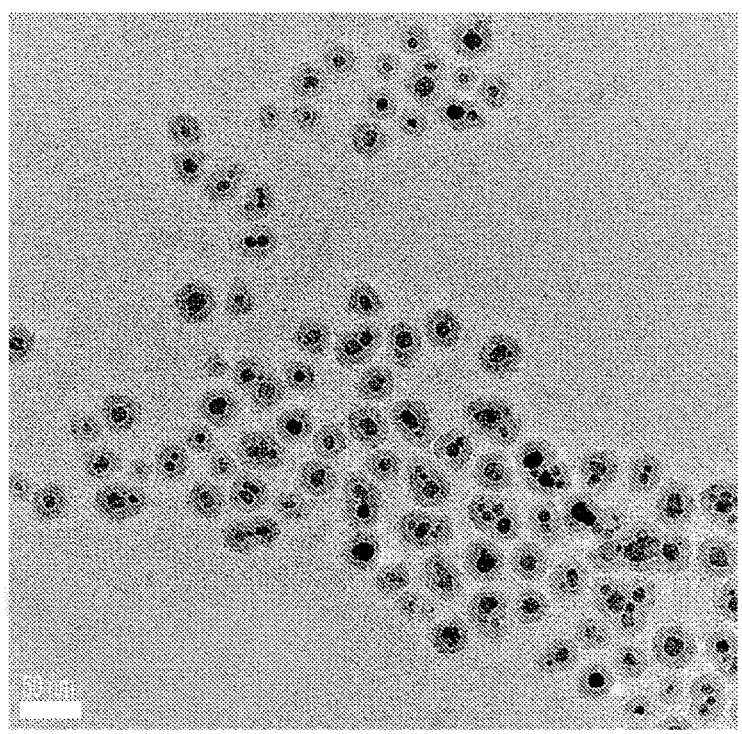

Aminooxy N-methyl-carbamate 7 (Scheme 3) was loaded onto $SiO_2@Fe_3O_4$ NPs using the established methodology (Sabourault, N.; et al., Org. Lett. 2002, 4, 2117-2119) to obtain aminooxy NPs 8 (AO@ $SiO_2@Fe_3O_4$). This functionalization increased the shell thickness by ~3 nm to afford $AO@SiO_2@Fe_3O_4$ NPs with a diameter of 30±8 nm as determined by TEM (FIG. 14B). The hydrodynamic diameter of aqueous $AO@SiO_2@Fe_3O_4$ NPs was measured at 96 nm with a polydispersity of 0.16, roughly similar to the hydrodynamic diameter of the starting $SiO_2@Fe_3O_4$ NPs at 103 nm with a polydispersity of 0.17. Little change was observed in ζ-potential, where both the $SiO_2@Fe_3O_4$ and $AO@SiO_2@Fe_3O_4$ NPs registered ca. −45 mV as aqueous suspensions. Simple mixing of $AO@SiO_2@Fe_3O_4$ with anthracene aldehyde 10 in aqueous ethanol gave NPs 9 ($FL@SiO_2@Fe_3O_4$). In an alternate approach, the oximation step was conducted first by reacting anthracene aldehyde 10 with 7 (Scheme 3) followed by hydrosilylation of the oxime ether adduct and then loading onto $SiO_2@Fe_3O_4$ NPs to obtain 9.

With the $FL@SiO_2@Fe_3O_4$ NPs in hand, the AMF-induced hydrolysis of the carbamate linkage was studied by measuring the release of anthracene oxime ether fragment 11 (Scheme 4).

Scheme 4. AMF-induced carbamate hydrolysis.

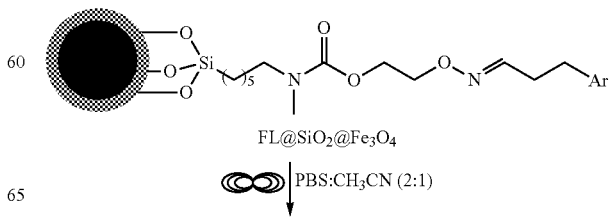

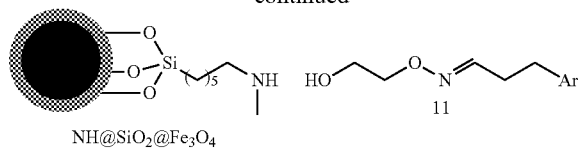

NH@SiO$_2$@Fe$_3$O$_4$

The AMF experiments were conducted as described above (2:1 PBS:acetonitrile solution, pH 7.4). As can be seen in FIG. 16, AMF irradiation stimulated a rapid release of substrate from FL@SiO$_2$@Fe$_3$O$_4$. MALDI-TOF analysis confirmed that the oxime ether-anthracene fragment 11 was liberated from the NP formulation on AMF irradiation. Based on fluorescent measurements, 40 minutes of AMF exposure resulted in 67±3% of payload release; longer exposure times did not release additional 11. The switch from carbonate to carbamate dramatically reduced non-AMF release of substrate (FIG. 16)—less than 10% of the payload was released at 37° C. after 40 minutes. The rapid release of the fluorophore fragment on AMF application is quite remarkable in that N,N-dialkyl carbamates are not expected to cleave under these mild conditions (e.g., a previous kinetic study estimates a typical half-life of >550 years at 25° C. and pH 7) (Dittert, L. W.; Higuchi, T. *J. Pharm. Sci.* 1963, 52, 852-857).

Uncoated Fe$_3$O$_4$ NPs were prepared that incorprotated ester, carbonate and carbamate linkers. Fe$_3$O$_4$ NPs were loaded with the alkoxysilane linker following a literature procedure (Galeotti, F.; et al., *J. Colloid Interface Sci.* 2011, 360, 540-547 and shown in Scheme 5. The alkoxysilane (10 mmol/g NPs) were added to a suspension of Fe$_3$O$_4$ NPs in CHCl$_3$. The mixture was heated to 65° C. for 48 h with mechanical stirring. Upon completion, the functionalized NPs were magnetically separated and the supernatant was decanted. The resulting NPs were washed with CHCl$_3$ (5×) followed by magnetic separation and decantation. After washing, the NPs were heated to 100° C. for 24 h to induce the final condensation and form a covalent bond between the linker and the iron NP. The loading of the functionalized NPs was determined by thermogravimetric analysis. All fluorescence measurements were taken at an excitation of 360 nm and an emission wavelength of 413 nm in a quartz cuvette. FIG. 17 shows the pulsed AMF-hydrolysis testing while FIG. 18 show hydrolysis without AMF.

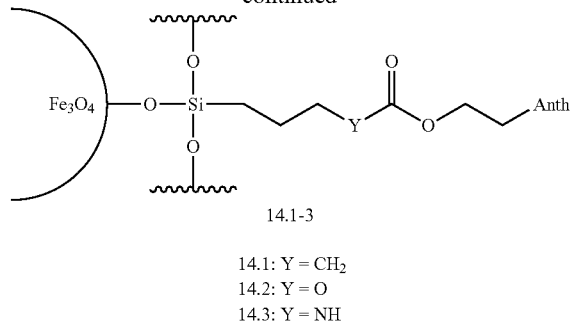

14.1-3

14.1: Y = CH$_2$
14.2: Y = O
14.3: Y = NH

Fe$_3$O$_4$ NPs with different coatings were prepared to test the effect of restricting excess to the Fe$_3$O$_4$ core (FIG. 19). Excess polysaccharide, D-lactose or dextran (6 kD), was added to 3.1 (10 mg) in DMSO (1 mL) and the suspension was mixed for 17 h. The NPs were magnetically separated and the supernatant was decanted. The resulting NPs were washed once with DMSO and twice with MeOH before being dried under vacuum.

Unfunctionalized Fe$_3$O$_4$ NPs were coated with a silica shell using the Stöber process (Hui, C.; et al., *Nanoscale* 2011, 3, 701-705). Briefly, Fe$_3$O$_4$ NPs (115 mg) were suspended in Millipore water with sonication, then NH$_4$OH (25%, 4.4 mL, 28.6 mmol) and EtOH (180 mL) were added to the suspension. With rapid mechanical stirring, tetraethyl orthosilicate (TEOS) (1.76 mL, 7.94 mmol) was added dropwise at rt and reaction was stirred overnight. The SiO$_2$@Fe$_3$O$_4$ NPs were magnetically separated and the supernatant was decanted. The remaining NPs were washed with EtOH (4×) and were dried under vacuum. FIG. 19 shows the hydrolysis of the carbonate linker with these various coatings.

Therapeutic magnetic nanoparticles with therapeutic agents comprising a ketone or aldehyde group can be readily prepared according Scheme 3 above using chemical steps analogous to those described herein.

The ketone or aldehyde of the therapeutic agent has been converted to a prodrug of the therapeutic agent as shown in formula IIIa which prodrug is attached to the linker. Accordingly, one embodiment provides a therapeutic agent which is a prodrug of the therapeutic agent and is represented by formula IIIa:

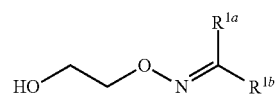

IIIa wherein R$^{1a}$ and R$^{1b}$ together with the remainder of formula IIIa are the prodrug of the therapeutic agent. It is to be understood that the prodrug of formula IIIa represents a therapeutic agent of formula IIIb (wherein R$^{1a}$ and R$^{1b}$ and the carbonyl to which they are attached represent a therapeutic agent):

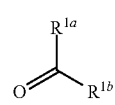

IIIb

Scheme 5. Hydrosilylation and Fe$_3$O$_4$ NP loading with triethoxysilane-ester, -carbonate and -carbamate linkers.

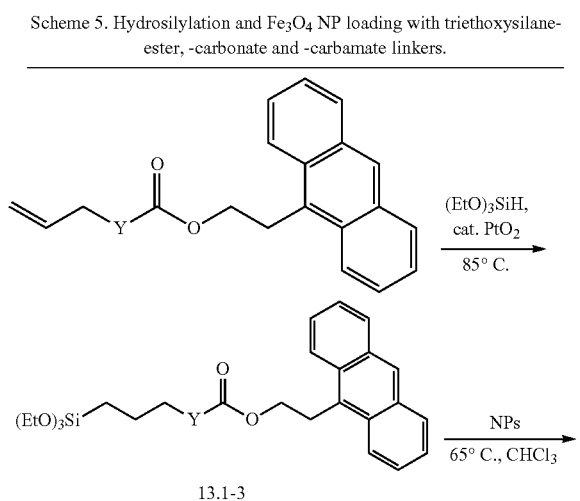

13.1-3 wherein the ketone or aldehyde of the therapeutic agent of formula IIIb has been condensed with the aminooxy moiety of HO—(CH$_2$)$_2$—O—NH$_2$ to arrive at the prodrug of the therapeutic agent of formula IIIa.

In one embodiment a residue of a therapeutic agent (D or —Z-D$^1$) is a represented by formula IIIc:

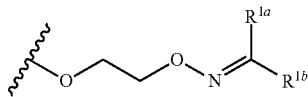

IIc wherein R$^{1a}$ and R$^{1b}$ together with the remainder of formula IIIc are the residue of the therapeutic agent (D or —Z-D$^1$).

Example 2. Preparation of Gold NP Linker

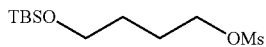 [SMILES: CC(C)(C)[Si](C)(C)OCCCCOS(C)(=O)=O]

4-((tert-Butyldimethylsilyl)oxy)butyl methanesulfonate

Methanesulfonyl chloride (2.87 mL, 37.0 mmol) was added to a solution of crude 4-((tert-butyldimethylsilyl)oxy)butan-1-ol (6.58 g, 32.2 mmol) and Et$_3$N (6.79 mL, 48.3 mmol) in dry CH$_2$Cl$_2$ (107 mL) at 0° C. and was stirred for 2 h. The reaction solution was washed twice with sat. NH$_4$Cl and the combined aqueous layers were extracted twice with CH$_2$Cl$_2$. The combined organic phases were washed once with brine and was dried over Na$_2$SO$_4$, filtered and concentrated in vacuo to afford 4-((tert-butyldimethylsilyl)oxy)butyl methanesulfonate (9.03 g, 99%) as an orange oil and was used without further purification. R$_f$ 0.52 (1:3, EtOAc:hexanes); $^1$H NMR (400 MHz, CDCl$_3$) δ 0.04 (s, 6H), 0.88

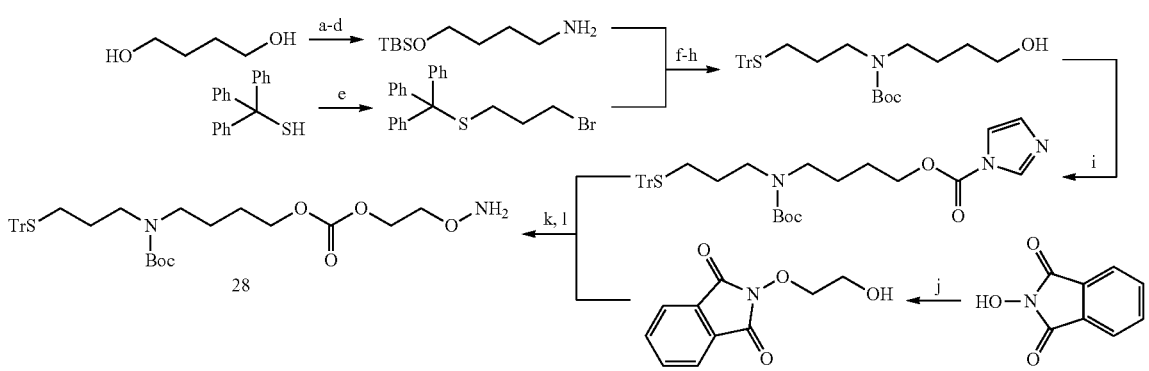

Scheme 6. Synthesis of carbonate linker 28 for attachment to Au@Fe$_3$O$_4$ NPs. Conditions: a. TBSCl, Et$_3$N, CH$_2$Cl$_2$, 0° C., 17 h; b. MsCl, Et$_3$N, CH$_2$Cl$_2$, 0° C., 1.5 h; c. phthalimide, K$_2$CO$_3$, DMSO, 75° C., 18 h; d. N$_2$H$_4$•H$_2$O, 1:2 EtOH:CH$_2$Cl$_2$, 20 h; e. 1,2-dibromoethane, K$_2$CO$_3$, THF, reflux, 24 h, 98%; f. MeCN, 55° C., 24 h, 82%; g. Boc$_2$O, Et$_3$N, CH$_2$Cl$_2$, 0° C., 2 h; h. 1 M TBAF in THF, THF, 0° C., 20 h, 62%; i. 1,1-carbonyldiimidazole, (i-Pr)NEt, CH$_2$Cl$_2$, 0° C., j. 2-bromoethanol, AcONa, DMSO, 70° C., 67%; k. DBU, MeCN, 18 h, 55%; l. N$_2$H$_4$•H$_2$O, CH$_2$Cl$_2$, 0° C., 92%.

Synthesis of Thiol Linker for Loading onto Au@Fe$_3$O$_4$ NPs

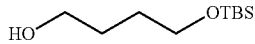

4-((tert-Butyldimethylsilyl)oxy)butan-1-ol

A solution of TBSCl (5.20 g, 34.5 mmol) in dry CH$_2$Cl$_2$ (60 mL) was added dropwise over 1 h to a solution of 1,4-butanediol (14.7 mL, 166 mmol) and Et$_3$N (6.99 mL, 49.8 mmol) in dry CH$_2$Cl$_2$ (50 mL) at 0° C. and was stirred overnight. The solvent was removed in vacuo and the remaining oil was extracted with hexanes (4×) and the combined extractions were washed twice with sat. NH$_4$Cl, once with brine and was dried over Na$_2$SO$_4$, filtered and concentrated in vacuo to afford crude 4-((tert-butyldimethylsilyl)oxy)butan-1-ol (6.58 g, 93%) as a colorless oil and was used without further purification. R$_f$ 0.44 (1:3, EtOAc:hexanes).

(s, 9H), 1.62 (quin, J=6.0 Hz, 2H), 1.83 (quin, J=7.2 Hz, 2H), 2.99 (s, 3H), 3.64 (t, J=6.0 Hz, 2H), 4.26 (t, J=6.6 Hz, 2H); $^{13}$C NMR (100 MHz, CDCl$_3$) δ −5.2, 18.5, 26.1, 28.8, 37.6, 62.4, 70.3.

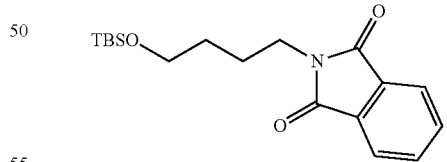

2-(4-((tert-Butyldimethylsdyl)oxy)butyl)-2,3-dihydro-W-isoindole-1,3-dione

Phthalimide (8.55 g, 58.1 mmol) was added to a solution of 4-((tert-butyldimethylsilyl)oxy)butyl methanesulfonate (8.64 g, 30.6 mmol) and K$_2$CO$_3$ (5.07 g, 36.7 mmol) in DMSO (180 mL) and the solution was heated to 75° C. for 17 h. The reaction was then cooled to rt and was quenched with water. The aqueous solution was extracted with EtOAc (4×) and the combined organic phases were washed with water (3×). The organic phase was then washed with brine, dried over Na$_2$SO$_4$, filtered and concentrated in vacuo to afford 2-(4-((tert-butyldimethylsilyl)oxy)butyl)-2,3-dihydro-1H-isoindole-1,3-dione (9.27 g, 91%) as white crystals and was used without further purification. R$_f$ 0.59 (1:3, EtOAc:hexanes); $^1$H NMR (400 MHz, CDCl$_3$) δ 0.03 (s, 6H), 0.87 (s, 9H), 1.55 (quin, J=6.4 Hz, 2H), 1.74 (quin, J=7.4 Hz, 2H), 3.63 (t, J=6.4 Hz, 2H), 3.70 (t, J=7.2 Hz, 2H), 7.65 (dd, J=2.4, 2.8 Hz, 2H), 7.83 (dd, J=1.6, 3.4 Hz, 2H); $^{13}$C NMR (100 MHz, CDCl$_3$) δ −5.1, 18.5, 25.3, 26.1, 30.2, 38.1, 62.7, 123.4, 132.4, 134.0, 168.6.

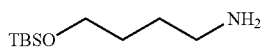

(4-Aminobutoxy)(tert-butyl)dimethylsilane

Hydrazine monohydrate (6.74 mL, 139 mmol) was added to a solution of crude 2-(4-((tert-butyldimethylsilyl)oxy) butyl)-2,3-dihydro-1H-isoindole-1,3-dione (9.27 g, 27.8 mmol) in CH$_2$Cl$_2$ (140 mL) at 0° C. and was stirred overnight, allowing the reaction to come to rt. The white precipitate was filtered and the filter cake was washed with ample CH$_2$Cl$_2$. The crude solution was concentrated in vacuo to afford (4-aminobutoxy)(tert-butyl)dimethylsilane (3.99 g, 71%) as a light yellow oil and was used without further purification. R$_f$ 0.26 (1:9, MeOH:CH$_2$Cl$_2$ with 1% NH$_4$OH); $^1$H NMR (400 MHz, CDCl$_3$) δ 0.03 (s, 6H), 0.87 (s, 9H), 1.44-1.55 (m, 4H), 1.61 (br s, 2H), 2.68 (t, J=6.8 Hz, 2H), 3.60 (t, J=6.2 Hz); $^{13}$C NMR (100 MHz, CDCl$_3$) δ −5.1, 18.5, 26.1, 30.4, 30.5, 42.3, 63.3.

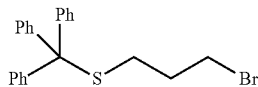

(((3-Bromopropyl)sulfanyl)diphenylmethyl)benzene

K$_2$CO$_3$ (2.28 g, 16.5 mmol) followed by 1,3-dibromopropane (7.61 mL, 75 mmol) was added to a solution of triphenylmethanethiol (4.22 g, 15.3 mmol) in dry THF (75 mL) under N$_2$. The reaction was refluxed for 24 h before cooling to rt. The reaction solution was washed twice with water, extracted twice with Et$_2$O, washed with brine, dried over Na$_2$SO$_4$, filtered and concentrated in vacuo. The excess 1,3-dibromopropane was distilled off to afford (((3-bromopropyl)sulfanyl)diphenylmethyl)benzene (5.94 g, 98%) as white crystals. R$_f$ 0.54 (1:3, CH$_2$Cl$_2$:hexanes); $^1$H NMR (400 MHz, CDCl$_3$) δ 1.81 (quin, J=6.8 Hz, 2H), 2.32 (t, J=6.8 Hz, 2H), 3.32 (t, J=6.8 Hz, 2H), 7.19-7.30 (m, 9H), 7.40-7.44 (m, 6H); $^{13}$C NMR (100 MHz, CDCl$_3$) δ 30.5, 31.8, 32.5, 66.9, 126.9, 128.1, 129.8, 144.9.

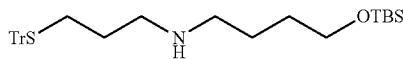

12,12,13,13-Tetramethyl-1,1,1-triphenyl-11-oxa-2-thia-6-aza-12-silatetradecane (((3-bromopropyl)sulfanyl)diphenylmethyl)benzene (800 mg, 2.01 mmol) was added to a solution of (4-aminobutoxy) (tert-butyl)dimethylsilane (1.02 g, 5.03 mmol) in MeCN (20 mL) and the reaction was heated to 55° C. for 24 h. After cooling to rt, the reaction was quenched with sat. NaHCO$_3$ and extracted three times with EtOAc. The combined organic phases were washed with brine, dried over Na$_2$SO$_4$, filtered and concentrated in vacuo. The crude material was purified by column chromatography (SiO$_2$, 0:1 to 1:4, MeOH:CH$_2$Cl$_2$ with 1% NH$_4$OH gradient) to give 12,12, 13,13-tetramethyl-1,1,1-triphenyl-11-oxa-2-thia-6-aza-12-silatetradecane (852 mg, 82%) as an orange oil. R$_f$ 0.33 (1:4, MeOH:CH$_2$Cl$_2$ with 1% NH$_4$OH); $^1$H NMR (400 MHz, CDCl$_3$) δ 0.04 (s, 6H), 0.88 (s, 9H), 1.51-1.52 (m, 4H), 1.60 (quin, J=7.4 Hz, 2H), 2.17 (t, J=7.0 Hz, 2H), 2.57 (t, J=7.2 Hz, 4H), 3.59 (t, J=6.0 Hz, 2H), 7.17-7.28 (m, 9H), 7.39-7.41 (m, 6H); $^{13}$C NMR (100 MHz, CDCl$_3$) δ −5.1, 18.6, 25.9, 26.2, 28.5, 29.9, 30.7, 48.6, 49.5, 63.2, 66.8, 126.8, 128.1, 129.8, 145.1.

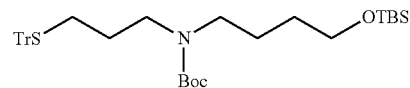

tert-Butyl N-(4((tert-butyldimethylsiyl)oxy)butyl)-N-(3-((triphenylmethyl)sufanyl) propyl)carbamate Boc$_2$O (348 mg, 1.60 mmol) was added to a solution of 12,12,13,13-tetramethyl-1,1,1-triphenyl-11-oxa-2-thia-6-aza-12-silatetradecane (754 mg, 1.45 mmol) and Et$_3$N (224 µL, 1.60 mmol) in CH$_2$Cl$_2$ (5 mL) at 0° C. After 3 h, the reaction solution was washed twice with sat. NH$_4$Cl and the aqueous phase was extracted twice with CH$_2$Cl$_2$. The combined organic phases were washed with brine, dried over Na$_2$SO$_4$, filtered and concentrated in vacuo to afford crude tert-butyl N-(4((tert-butyldimethylsiyl)oxy)butyl)-N-(3-((triphenylmethyl)sufanyl)propyl)carbamate as an orange oil and was used without further purification. R$_f$ 0.81 (1:19, EtOAc:CH$_2$Cl$_2$); $^1$H NMR (400 MHz, CDCl$_3$) δ 0.03 (s, 6H), 0.88 (s, 9H), 1.39 (br s, 4H), 1.45 (br s, 2H), 1.52 (s, 9H), 2.13 (t, J=7.4 Hz, 2H), 3.05 (br s, 4H), 3.58 (t, J=6.0 Hz, 2H), 7.18-7.29 (m, 9H), 7.39-7.41 (m, 6H); $^{13}$C NMR (100 MHz, CDCl$_3$) δ −5.1, 18.5, 25.9, 26.2, 27.6, 28.6, 29.6, 30.3, 46.5, 47.1, 63.1, 66.8, 79.3, 126.8, 128.1, 129.8, 145.1, 155.6.

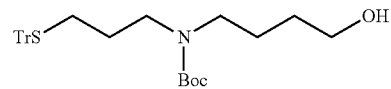

tert-Butyl N-(4-hydroxybutyl)-N-(3-((triphenylmethyl)sulfanyl)propyl)carbamate

TBAF (1.89 mL of 1 M solution in THF, 1.89 mmol) was added to a solution of crude tert-butyl N-(4((tert-butyldimethylsiyl)oxy)butyl)-N-(3-((triphenylmethyl)sufanyl) propyl)carbamate (1.45 mmol) in dry THF (3 mL) at 0° C. and the reaction was stirred overnight, allowing the reaction to warm to rt. Upon completion, the reaction was washed twice with sat. NaHCO$_3$ and the combined aqueous phases were extracted three times with Et$_2$O. The combined organic layers were washed with brine, dried over Na$_2$SO$_4$, filtered and concentrated in vacuo. The crude material was purified by column chromatography (SiO$_2$, 3:7, EtOAc:CH$_2$Cl$_2$) to give tert-butyl N-(4-hydroxybutyl)-N-(3-((triphenylmethyl)sulfanyl)propyl)carbamate (453 mg, 62% over 2 steps) as a light yellow oil. $R_f$ 0.52 (3:7, EtOAc:CH$_2$Cl$_2$); $^1$H NMR (400 MHz, CDCl$_3$) δ 1.40 (s, 9H), 1.47-1.51 (m, 4H), 1.58 (quin, J=7.6 Hz, 2H), 3.08 (br s, 4H), 3.63 (t, J=6.0 Hz, 2H), 7.19-7.30 (m, 9H), 7.41-7.43 (m, 6H); $^{13}$C NMR (100 MHz, CDCl$_3$) δ 24.8, 28.2, 28.6, 29.5, 29.7, 46.6, 46.9, 62.6, 66.8, 79.5, 126.8, 128.0, 129.7, 145.0, 155.7.

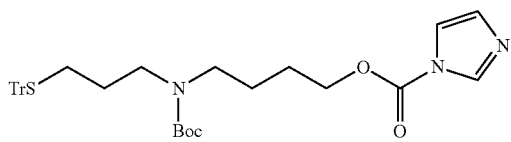

4-(((tert-Butoxy)carbonyl)((3-((triphenylmethyl)sulfanyl)propyl))amino) butyl 1H-imidazole-1-carboxylate 1,1'-Carbonyldiimidazole (214 mg, 1.32 mmol) was added to a solution of tert-butyl N-(4-hydroxybutyl)-N-(3-((triphenylmethyl)sulfanyl)propyl) carbamate (444 mg, 0.88 mmol) and (i-Pr)$_2$NEt (228 μL, 1.32 mmol) in dry CH$_2$Cl$_2$ (3 mL) at 0° C. and was stirred overnight. The reaction solution was washed twice with water and extracted once with CH$_2$Cl$_2$. The combined organic layers were washed twice with sat. NH$_4$Cl, once with brine, were dried over Na$_2$SO$_4$, filtered and concentrated in vacuo to afford crude 4-(((tert-butoxy)carbonyl)((3-((triphenylmethyl)sulfanyl)propyl)) amino) butyl 1H-imidazole-1-carboxylate (517 mg, 98%) as a light yellow oil and was used without further purification. $R_f$ 0.50 (3:7, EtOAc:CH$_2$Cl$_2$); $^1$H NMR (400 MHz, CDCl$_3$) δ 1.42 (s, 9H), 1.59 (br s, 4H), 1.76 (quin, J=6.8 Hz, 2H), 2.18 (t, J=7.4 Hz, 2H), 3.11 (br s, 4H), 4.42 (t, =6.6 Hz, 2H), 7.08 (s, 1H), 7.20-7.31 (m, 9H), 7.42-7.44 (m, 7H), 8.15 (s, 1H); $^{13}$C NMR (100 MHz, CDCl$_3$) δ 24.6, 25.9, 28.2, 28.5, 29.4, 46.5 (2 C's), 66.8, 68.1, 79.6, 117.2, 126.7, 128.0, 129.7, 130.8, 137.2, 144.9, 148.8, 155.5.

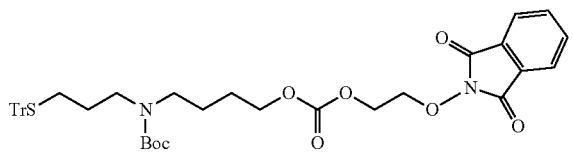

2-(2-(((4-(((tert-Butoxy)carbonyl)((3-((triphenylmethyl)sulfanyl)propyl))amino) butoxy)carbonyl)oxy) ethoxy)-2,3-dihydro-1H-isoindole-1,3-dione DBU (129 μL, 0.86 mmol) was added to a solution of crude tert-butyl N-(4-hydroxybutyl)-N-(3-((triphenylmethyl)sulfanyl)propyl)carbamate (517 mg, 0.86 mmol) in dry MeCN (4 mL). After stirring for 10 min, 2-(2-hydroxyethoxy)-2,3-dihydro-1H-isoindole-1,3-dione (178 mg, 0.86 mmol) was added and the reaction was stirred overnight. Upon completion, the reaction was washed twice with sat. NH$_4$Cl and the combined aqueous layers were extracted three times with EtOAc. The combined organic layers were washed with brine, dried over Na$_2$SO$_4$, filtered and concentrated in vacuo. The crude material was purified by column chromatography (SiO$_2$, 3:17, EtOAc:CH$_2$Cl$_2$) to give 2-(2-(((4-(((tert-butoxy)carbonyl)((3-((triphenylmethyl)sulfanyl)propyl))amino)butoxy)carbonyl)oxy) ethoxy)-2,3-dihydro-1H-isoindole-1,3-dione (350 mg, 55% over 2 steps) as a colorless oil. $R_f$ 0.75 (3:17, EtOAc:CH$_2$Cl$_2$); NMR (400 MHz, CDCl$_3$) δ 1.40 (s, 9H), 1.46-1.64 (m, 6H), 2.15 (t, J=7.4 Hz, 2H), 3.06 (br s, 4H), 4.14 (t, J=6.4 Hz, 2H), 4.43-4.48 (m, 4H), 7.18-7.29 (m, 9H), 7.39-7.42 (m, 6H), 7.73-7.76 (m, 2H), 7.81-7.85 (m, 2H); $^{13}$C NMR (100 MHz, CDCl$_3$) δ 24.6, 26.1, 28.2, 28.6, 29.5, 46.5, 46.6, 65.2, 68.1, 75.6, 79.5, 123.8, 126.8, 128.0, 129.0, 129.7, 134.7, 145.0, 155.1, 155.5, 163.5.

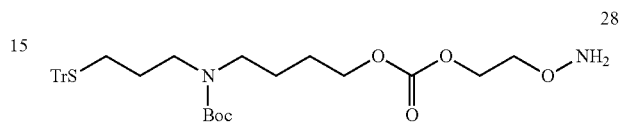

N-(4-(((2-(aminooxy)ethoxy)carbonyl)oxy)butyl)-N-((tert-butoxy)carbonyl)-3-((triphenylmethyl)sulfanyl)propan-1-amine Hydrazine monohydrate (51 μL, 1.04 mmol) was added to a solution of 2-(2-(((4-(((tert-butoxy)carbonyl)((3-((triphenylmethyl)sulfanyl)propyl))amino)butoxy)carbonyl) oxy) ethoxy)-2,3-dihydro-1H-isoindole-1,3-dione (154 mg. 0.21 mmol) in CH$_2$Cl$_2$ at 0° C. and stirred for 2 h. When complete, the white precipitate was removed by filtration and the filter cake was washed with ample CH$_2$Cl$_2$. The filtrate was concentrated in vacuo to afford 28 (127 mg, 100%) as a colorless oil and did not require further purification. $R_f$ 0.52 (1:3, EtOAc:CH$_2$Cl$_2$); $^1$H NMR (400 MHz, CDCl$_3$) δ 1.38 (s, 9H), 1.48-1.62 (m, 6H), 2.14 (t, J=7.4 Hz, 2H), 3.05 (br s, 4H), 3.85 (t, J=4.6 Hz, 2H), 4.12 (t, =6.4 Hz, 2H), 4.33 (t, J=4.4 Hz, 2H), 5.51 (br s, 2H), 7.18-7.21 (m, 3H), 7.25-7.29 (m, 6H), 7.39-7.41 (m, 6H); $^{13}$C NMR (100 MHz, CDCl$_3$) δ 24.7, 26.2, 27.5, 28.6, 29.5, 46.7 (2 C's), 65.5, 66.8, 68.0, 73.4, 79.5, 126.8, 128.0, 129.7, 145.0, 155.5, 155.6.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g, "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A therapeutic magnetic nanoparticle, or a salt thereof, comprising a magnetic nanoparticle covalently bonded to one or more -L-D groups wherein;

L is a linker $-L^1-L^2-$;
wherein:
$L^2$ is:

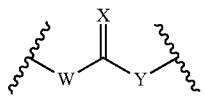

W is absent, —O—, —S— or $-NR^b-$;
X is O, S or $NR^c$;
Y is absent, —O—, —S— or $-NR^d-$;
$R^b$ is H, $(C_1-C_6)$alkyl, $(C_2-C_6)$alkenyl or $(C_2-C_6)$alkynyl;
$R^c$ is H, $(C_1-C_6)$alkyl, $(C_2-C_6)$alkenyl or $(C_2-C_6)$alkynyl;
$R^d$ is H, $(C_1-C_6)$alkyl, $(C_2-C_6)$alkenyl or $(C_2-C_6)$alkynyl; and
wherein D together with Y of $L^2$ or D together with W—C(=X)—Y of $L^2$ is the moiety:

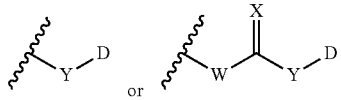

wherein the moiety is a residue of a therapeutic agent;
each $L^1$ is covalently bonded to the magnetic nanoparticle and is independently a branched or unbranched chain or cyclic group or a combination of chain and cyclic groups that comprises 1-200 atoms; and wherein the atoms of $L^1$ are selected from hydrogen, carbon, oxygen, nitrogen, sulfur and silicon and wherein $L^1$ does not include an —NH—, —NH$_2$ or —NHR group wherein R is $(C_1-C_6)$alkyl;
each $L^2$ is independently a group capable of releasing a therapeutic agent; and
wherein L is not capable of undergoing intramolecular cyclization to release the therapeutic agent.

2. The therapeutic magnetic nanoparticle of claim 1, or a salt thereof, comprising a magnetic nanoparticle covalently bonded to one or more -L-D groups wherein D is a residue of a therapeutic agent and L is a linker, wherein:

L is $-L^1-L^2-$;
each $L^1$ is covalently bonded to the magnetic nanoparticle and is independently a branched or unbranched chain or cyclic group or a combination of chain and cyclic groups that comprises 1-50 atoms; and
each $L^2$ is independently a group capable of releasing a therapeutic agent.

3. The therapeutic magnetic nanoparticle of claim 1, wherein $L^1$ does not include a hydrazone group.

4. The therapeutic magnetic nanoparticle of claim 1, wherein $L^1$ comprises a $(C_1-C_{15})$alkylene, $(C_1-C_{15})$heteroalkylene, $(C_2-C_{15})$alkenylene, $(C_2-C_{15})$alkynylene, wherein any $(C_1-C_{15})$alkylene, $(C_1-C_{15})$heteroalkylene, $(C_2-C_{15})$alkenylene or $(C_2-C_{15})$alkynylene of $L^1$ is optionally substituted with one or more halogen.

5. The therapeutic magnetic nanoparticle of claim 1, wherein $L^1$ comprises a $(C_1-C_{15})$alkylene, $(C_2-C_{15})$alkenylene, or $(C_2-C_{15})$alkynylene, wherein any $(C_1-C_{15})$alkylene, $(C_2-C_{15})$alkenylene or $(C_2-C_{15})$alkynylene of $L^1$ is optionally substituted with one or more halogen.

6. A therapeutic magnetic nanoparticle or a salt thereof, comprising a magnetic nanoparticle covalently bonded to one or more -L-D groups, wherein each -L-D independently has the following formula I:

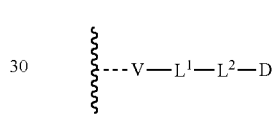

wherein:
V is $-OSi(G)_2-$, and the dashed line represents a covalent bond between the oxygen atom of $-OSi(G)_2-$ and the magnetic nanoparticle; or V is —S—, and the dashed line represents a covalent bond between —S— and the magnetic nanoparticle;
$L^1$ is $(C_1-C_{15})$alkylene, $(C_1-C_{15})$heteroalkylene, $(C_2-C_{15})$alkenylene or $(C_2-C_{15})$alkynylene, wherein any $(C_1-C_{15})$alkylene, $(C_1-C_{15})$heteroalkylene, $(C_2-C_{15})$alkenylene or $(C_2-C_{15})$alkynylene of $L^1$ is optionally substituted with one or more halogen and wherein the $(C_1-C_{15})$heteroalkylene does not include nitrogen;
$L^2$ is:

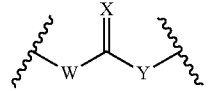

W is absent, —O—, —S— or $-NR^b-$;
X is O, S or $NR^c$;
Y is absent, —O—, —S— or $-NR^d-$;
each G is independently $-OR^{a1}$, $-OR^{a2}$ or $(C_1-C_6)$alkyl;
$R^{a1}$ is a covalent bond between the oxygen atom of $-OR^{a1}$ and the magnetic nanoparticle;
each $R^{a2}$ is independently H or $(C_1-C_6)$alkyl; or two $-OR^{a2}$ groups of two adjacent L-D groups together form —O—;
$R^b$ is H, $(C_1-C_6)$alkyl, $(C_2-C_6)$alkenyl or $(C_2-C_6)$alkynyl;
$R^c$ is H, $(C_1-C_6)$alkyl, $(C_2-C_6)$alkenyl or $(C_2-C_6)$alkynyl;
$R^d$ is H, $(C_1-C_6)$alkyl, $(C_2-C_6)$alkenyl or $(C_2-C_6)$alkynyl; and wherein D together with Y of $L^2$ or D together with W—C(=Z)—Y of $L^2$ is a residue of a therapeutic agent.

7. The therapeutic magnetic nanoparticle of claim 6, wherein V is —OSi(G)$_2$-, the magnetic nanoparticle is optionally coated with silica, and the dashed line represents a covalent bond between the oxygen atom of —OSi(G)$_2$- and the magnetic nanoparticle optionally coated with silica; or V is —S—, the magnetic nanoparticle is magnetic nanoparticle coated with gold, and the dashed line represents a covalent bond between —S— and the magnetic nanoparticle coated with gold.

8. The therapeutic magnetic nanoparticle of claim 6, wherein V is —OSi(G)$_2$-, the magnetic nanoparticle is an iron oxide nanoparticle coated with silica, and the dashed line represents a covalent bond between the oxygen atom of —OSi(G)$_2$- and the iron oxide nanoparticle coated with silica.

9. The therapeutic magnetic nanoparticle of claim 6, wherein -L-D has the following formula Ia:

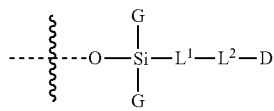

Ia wherein the dashed bond represents a covalent bond to the magnetic nanoparticle.

10. The therapeutic magnetic nanoparticle of claim 6, wherein V is —S—, the magnetic nanoparticle is coated in gold, and the dashed line represents a covalent bond between —S— and the magnetic nanoparticle coated in gold.

11. The therapeutic magnetic nanoparticle of claim 6, wherein -L-D has the following formula Ib:

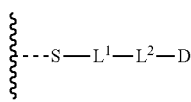

Ib wherein the dashed bonds represent a covalent bond to the magnetic nanoparticle.

12. The therapeutic magnetic nanoparticle of claim 6, wherein $L^1$ is $(C_1-C_{15})$alkylene, $(C_2-C_{15})$alkenylene or $(C_2-C_{15})$alkynylene, wherein any $(C_1-C_{15})$alkylene, $(C_2-C_{15})$alkenylene or $(C_2-C_{15})$alkynylene of $L^1$ is optionally substituted with one or more halogen.

13. The therapeutic magnetic nanoparticle of claim 1, wherein $L^2$ is:

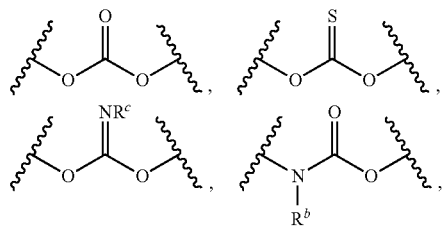

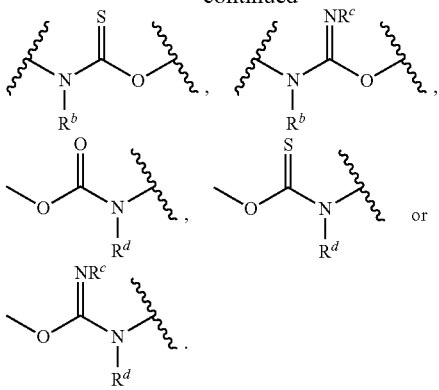

14. The therapeutic magnetic nanoparticle of claim 1, wherein the residue of a therapeutic is a residue of a prodrug of a therapeutic agent represented by formula IIIe:

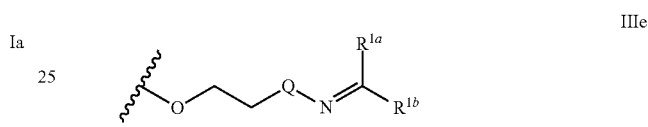

IIIe wherein Q is —O— or —NH— and $R^{1a}$ and $R^{1b}$ together with the remainder of formula IIIe are the residue of the prodrug of the therapeutic agent.

15. The therapeutic magnetic nanoparticle of claim 1, wherein the residue of a therapeutic agent or prodrug thereof is a residue of Cladribine, Azacitidine, Abraxane, Adcetris, Doxorubicin, Afinitor, Vinblastine, Amifostine, Amifostine, Arabinosylcytosine, Cytarabine, Pamidronic Acid, Nelarabine, Bicalutamide, Blemycin, Bortezomib, Cabazitaxel, Irinotecan, Camptothecin, Capecitabine, Temsirolimus, Daunorubicin, Cortisone, Decitabine, Dasatinib, Dexamethasone, Prednisolone, Dexamethasone Acetate, Mitoxantrone, Docetaxel, Hydroxycarbamide, Methylprednisolone, Epirubicin, Curcumin, Estramustine, Eribulin, Etoposide, Everolimus, Raloxifene, Fulvestrant, Floxuridine, Fludarabine, Fluoxymesterone, Gemcitabine, Goserelin, Topotecan, Hydrocortisone, Hydrocortone Phosphate, Idarubicin, Ixabepilone, Vincristine, Leuprolide (Leuprorelin), Megestrol, Vinorelbine, Nelarabine, Pentostatin, Octreotide, Paclitaxel, Streptozotocin, Teniposide, Valrubicin, Vorinostat, Zoledronic Acid Cladribine, Azacitidine, Mecaptopurine, Tioguanine, Actinomycin D, Doxorubicin, Anagrelide, Pemetrexed, Vinblastine, Melphalan, Methotrexate, Amifostine, Aminoglutethimide, Arabinosylcytosine, Cytarabine, Pamidronic Acid, Nelarabine, Axitinib, Bleomycin, Bosutinib, Folinic Acid (Na or Ca), Leucovorin, Vandetanib, Lenalidomide, Daunorubicin, Crizotinib, Dacarbazine, Decitabine, Dasatinib, Mitoxantrone, Eribulin, Erlotinib, Fludarabine, Pralatrexate, Gefitinib, Gemcitabine, Imatinib, Goserelin, Idarubicin, Lapatinib, Vincristine, Leuprolide, Procarbazine, Methotrexate, Mitomycin, Vinorebine, Nelarabine, Nilotinib, Pentostatin, Octreotide, Pazopanib, Sunitinib, Abraxane, Actinomycin D, Doxorubicin, Afinitor, Exemestane, Carfilzomib, Daunorubicin, Cortisone, Prednisolone, Prednisone, Dexamethasone Acetate, Docetaxel, Methylprednisolone, Epirubicin, Curcumin, Everolimus, Fluoxymesterone, Hydrocortisone, Hydrocortone Phosphate, Idarubicin, Ixabepilone, Vincristine, Megestrol, Valrubicin, Mesna, 13-cis-Retinoic Acid, Isotretinoin, Alitretinoin, Melphalan, Tretinoin, Methotrexate, Anastrozole, Bendamustine, Bexarotene, Carmustine, Lomustine, Chlorambucil and Ibritumomab Tiuxetan.

16. A pharmaceutical composition comprising a therapeutic magnetic nanoparticle as described in claim 1, or a pharmaceutically acceptable salt thereof and a pharmaceutically acceptable carrier.

17. A method for administering a therapeutic agent to an animal comprising administering the therapeutic magnetic nanoparticle as described in claim 1, or a pharmaceutically acceptable salt thereof, to the animal.

18. A method for treating cancer, a bacterial infection, a fungal infection, a parasitic infection or an antiviral infection in an animal in need thereof that has been administered an effective amount of a therapeutic magnetic nanoparticle as described in claim 1, or a pharmaceutically acceptable salt thereof, comprising providing conditions to release the therapeutic agent from the therapeutic magnetic nanoparticle.

19. The therapeutic magnetic nanoparticle of claim 6, wherein $L^2$ is:

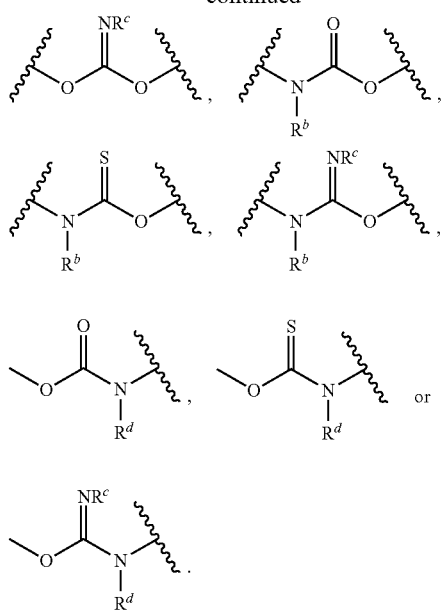

* * * * *

UNITED STATES PATENT AND TRADEMARK OFFICE
CERTIFICATE OF CORRECTION

PATENT NO. : 10,342,870 B2
APPLICATION NO. : 15/502131
DATED : July 9, 2019
INVENTOR(S) : Michael H. Nantz and Ralph Knipp It is certified that error appears in the above-identified patent and that said Letters Patent is hereby corrected as shown below:

In the Claims

Column 52, Lines 41-43, Claim 6, please delete "(Ci-$C_{15}$)alkylene, ($C_{1-15}$)heteroalkyl ene, ($C_{2-15}$)alkenyl ene," and insert -- ($C_1$-$C_{15}$)alkylene, ($C_{1-15}$)heteroalkylene, ($C_{2-15}$)alkenylene, -- therefor.

Signed and Sealed this
Nineteenth Day of November, 2019

Andrei Iancu
*Director of the United States Patent and Trademark Office*